US009624272B2

(12) United States Patent
Baker et al.

(10) Patent No.: US 9,624,272 B2
(45) Date of Patent: Apr. 18, 2017

(54) POLYPEPTIDES FOR TREATING AND/OR LIMITING INFLUENZA INFECTION

(71) Applicant: UNIVERSITY OF WASHINGTON THROUGH ITS CENTER FOR COMMERCIALIZATION, Seattle, WA (US)

(72) Inventors: David Baker, Seattle, WA (US); Eva-Maria Strauch, Seattle, WA (US); David La, Seattle, WA (US)

(73) Assignee: University of Washington Through its Center for Commercialization, Seattle, WA (US)

(*) Notice: Subject to any disclaimer, the term of this patent is extended or adjusted under 35 U.S.C. 154(b) by 0 days.

(21) Appl. No.: 14/766,375

(22) PCT Filed: Mar. 14, 2014

(86) PCT No.: PCT/US2014/028358
§ 371 (c)(1),
(2) Date: Aug. 6, 2015

(87) PCT Pub. No.: WO2014/152946
PCT Pub. Date: Sep. 25, 2014

(65) Prior Publication Data
US 2015/0376238 A1 Dec. 31, 2015

Related U.S. Application Data

(60) Provisional application No. 61/783,355, filed on Mar. 14, 2013.

(51) Int. Cl.
*A61K 38/00* (2006.01)
*C07K 14/00* (2006.01)
*C07K 14/11* (2006.01)
*C07K 7/08* (2006.01)
*G01N 33/569* (2006.01)

(52) U.S. Cl.
CPC .............. *C07K 14/001* (2013.01); *C07K 7/08* (2013.01); *C07K 14/11* (2013.01); *G01N 33/56983* (2013.01); *A61K 38/00* (2013.01); *C12N 2760/16134* (2013.01); *G01N 2333/11* (2013.01); *G01N 2500/02* (2013.01)

(58) Field of Classification Search
CPC ...... A61K 38/00; C07K 14/00; C07K 14/001; C07K 14/11; C07K 7/08
USPC ................................. 514/21.3; 530/324, 326
See application file for complete search history.

(56) References Cited

U.S. PATENT DOCUMENTS

| | | | |
|---|---|---|---|
| 5,571,836 A | 11/1996 | Bovin et al. | |
| 8,192,927 B2 | 6/2012 | Van Den Brink et al. | |
| 8,470,327 B2 | 6/2013 | Throsby et al. | |
| 8,637,456 B2 | 1/2014 | Sasisekharan et al. | |
| 2009/0074666 A1 | 3/2009 | Angstrom et al. | |
| 2010/0074920 A1 | 3/2010 | Natunen et al. | |
| 2011/0182897 A1 | 7/2011 | Hultberg et al. | |
| 2011/0191867 A1 | 8/2011 | Natunen et al. | |
| 2012/0219580 A1 | 8/2012 | Hwang et al. | |
| 2013/0143794 A1 | 6/2013 | Baker et al. | |
| 2013/0243792 A1 | 9/2013 | Vogels et al. | |
| 2013/0302349 A1 | 11/2013 | Shriver et al. | |
| 2013/0309248 A1 | 11/2013 | Throsby et al. | |

FOREIGN PATENT DOCUMENTS

| | | | |
|---|---|---|---|
| WO | 9412520 A1 | | 6/1994 |
| WO | 9728802 A1 | | 8/1997 |
| WO | 9821243 A1 | | 5/1998 |
| WO | WO 2007/095300 | * | 8/2007 |
| WO | 2011094445 A1 | | 8/2011 |
| WO | 2012018907 A2 | | 2/2012 |
| WO | 2012099566 A1 | | 7/2012 |
| WO | 2013044203 A2 | | 3/2013 |
| WO | 2013138259 A2 | | 9/2013 |
| WO | 2014080983 A1 | | 5/2014 |
| WO | 2014152946 | | 9/2014 |
| WO | 2016033168 | | 3/2016 |

OTHER PUBLICATIONS

Water from http://www.biology-online.org/dictionary/Water, pp. 1-3. Accessed Apr. 24, 2014.*
Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of *Escherichia coli* maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
Database Geneseq [Online] "Potato cystatin protein #4," (Nov. 1, 2007).
Database UniProt [Online] "RecName: Full=Uncharacterized protein MJ0327;" (Nov. 1, 1996).
Fleishman, et al., "Hotspot-centric de novo design of protein binders," Journal of Molecular Biology, vol. 413, No. 5, pp. 1047-1062, 2011.
Fleishman, et. al., "Computational design of proteins targeting the conserved stem region of influenza hemagglutinin," Science, vol. 332, No. 6031, pp. 816-821, 2011.

(Continued)

*Primary Examiner* — Julie Ha
(74) *Attorney, Agent, or Firm* — McDonnell Boehnen Hulbert & Berghoff LLP

(57) ABSTRACT

Disclosed herein are polypeptides that bind to the hemagglutinin protein of influenza virus, and which can be used for treating and diagnosing influenza infection.

20 Claims, 6 Drawing Sheets

(56) References Cited

OTHER PUBLICATIONS

Henne, et al., "The Genome Sequence of the Extreme Thermophile Thermus thermophilies," Nature Biotechnology, vol. 22, pp. 547-553, 2004.
International Search Report and Written Opinion for PCT/US2015/046920, 13 pages, 2016.
International Search Report and Written Opinion for PCT/US2014/028358, 2014.
Krause, et al., "Human Monoclonal Antibodies to Pandemic 1957 H2N2 and Pandemic 1968 H3N2 Influenza Viruses," Journal of Virology, vol. 86, No. 11, pp. 6334-6340, 2012.
Matsui, et al., "Enhanced binding of trigonal DNA-carbohydrate conjugates to lectin," Bioorganic & Medicinal Chemistry Letters, vol. 22, No. 19, pp. 6139-6143, 2012.
Murugapiran, et al., "Whole Genome Sequencing of Thermus Oshimai JL-2 and Thermus Thermophilus JL-18, Incomplete Denitrifiers from the United States Great Basin," Genome Announcements, vol. 1, No. 1, e00106-12, 2 pages, 2013.
Whitehead, et al., "Optimization of affinity, specificity and function of designed influenza inhibitors using deep sequencing," Nature Biotechnology, vol. 30, No. 6, pp. 543-548, 2012.

\* cited by examiner

From top to bottom SEQ ID NOs: 107, 108, 109, 110, 111, 112, 113, 114, 115, 116

POLYPEPTIDES FOR TREATING AND/OR LIMITING INFLUENZA INFECTION

This application is a U.S. national phase of International Application No. PCT/US2014/028358, filed on Mar. 14, 2014, which claims priority to U.S. Provisional Application No. 61/783,355, filed Mar. 14, 2013, both of which are incorporated by reference herein in their entirety.

FEDERAL FUNDING STATEMENT

This invention was made with government support under HDTRA1-10-1-0040 awarded by the Defense Threat Reduction Agency. The government has certain rights in the invention.

BACKGROUND

Influenza virus is a member of Orthomyxoviridac family. There are three subtypes of influenza viruses designated A, B, and C. The influenza virion contains a segmented negative-sense RNA genome, encoding, among other proteins, hemagglutinin (HA) and neuraminidase (NA). Influenza virus infection is initiated by the attachment of the virion surface HA protein to a sialic acid-containing cellular receptor (glycoproteins and glycolipids). The NA protein mediates processing of the sialic acid receptor, and virus penetration into the cell depends on HA-dependent receptor-mediated endocytosis. In the acidic confines of internalized endosomes containing an influenza virion, the HA2 protein undergoes conformational changes that lead to fusion of viral and cell membranes and virus uncoating and M2-mediated release of M1 proteins from nucleocapsid-associated ribonucleoproteins (RNPs), which migrate into the cell nucleus for viral RNA synthesis. Its surface protein hemagglutinin (HA) attaches to the sialic acid moieties on the host cell surface and mediates entry into the cell. So far, chemical analogs of the receptor have not been successful as viral-entry blockers. Current treatment options include therapeutic antibodies, small-molecules drugs and vaccination. These therapies allow protection against circulating subtypes, but may not protect against newly emerging strains. Hence, general or quickly adaptable solutions for cheap treatment options represent a constant need. Additionally, in order to rapidly diagnose early whether a patient indeed suffers from Influenza, sensitive diagnostics are desirable, as treatment at the onset of the infection have been shown to be more efficient.

Influenza presents a serious public-health challenge and new therapies are needed to combat viruses that are resistant to existing antivirals or escape neutralization by the immune system.

SUMMARY OF THE INVENTION

In one aspect, the invention provides isolated polypeptides comprising a polypeptide at least 70% identical over the full length of the amino acid sequence of SEQ ID NO: 1, wherein the polypeptide does not comprise the amino acid sequence of SEQ ID NO: 129. In various embodiments, the polypeptide comprises a polypeptide at least 70% identical over the full length of the amino acid sequence of SEQ ID NO:2 or 3. In various other embodiments, the polypeptide comprises an amino acid sequence selected from the group consisting of SEQ ID NOs: 11-39, 95-97, 126, and 130-134.

In another aspect, the invention provides isolated polypeptides comprising a polypeptide at least 70% identical over the full length of the amino acid sequence of SEQ ID NO:4, wherein the polypeptide does not comprise the amino acid sequence of SEQ ID NO: 130. In another embodiment, the polypeptide comprises a polypeptide at least 70% identical over the full length of the amino acid sequence of SEQ ID NO:5. In various other embodiments, the polypeptide comprises an amino acid sequence selected from the group consisting of SEQ ID NOs:40-47, 126, and 130-134.

In a further aspect, the invention provides isolated polypeptides comprising the amino acid sequence of SEQ ID NO:6. In various embodiments, the isolated polypeptide comprises the amino acid sequence of SEQ ID NOS: 7-8 or 48-54. In various further embodiments, the isolated polypeptide comprises the amino acid sequence of SEQ ID NOS 9 or 55-64. In other embodiments, the isolated polypeptide comprises the amino acid sequence of SEQ ID NOS:10 or 65-76 or 80-82.

In another aspect, the invention provides isolated polypeptides comprising a polypeptide selected from the group consisting of SEQ ID NOS: 85-89.

The invention also provides pharmaceutical compositions, comprising one or more polypeptides of the invention and a pharmaceutically acceptable carrier. The invention further provides isolated nucleic acids encoding the polypeptides of the invention, recombinant expression vectors comprising the isolated nucleic acids of the invention operatively linked to a control sequence, and recombinant host cell comprising the recombinant expression vectors of the invention.

In a further aspect, the invention provides methods for treating and/or limiting an influenza infection, comprising administering to a subject in need thereof a therapeutically effective amount of one or more polypeptides or pharmaceutical compositions of the invention, to treat and/or limit the influenza infection.

In another aspect, the invention provides methods for diagnosing an influenza infection, or monitoring progression of an influenza infection, comprising (a) contacting a biological sample from a subject suspected of having an influenza infection with a diagnostically effective amount of one or more polypeptides or pharmaceutical compositions of the invention, under conditions suitable for binding of the polypeptide to a viral HA protein present in the sample;

(b) removing unbound polypeptide and/or sample; and (c) detecting polypeptide-viral HA binding complexes, where the presence of such binding complexes indicates that the subject has an influenza infection, or provides a measure of progression of an influenza infection.

In a still further aspect, the invention provides methods for identifying candidate influenza vaccines, comprising (a) contacting test compounds with one or more polypeptides of the invention, under conditions suitable for polypeptide binding; and (b) identifying those test compounds that bind to the polypeptide of the invention, wherein such test compounds are candidate influenza vaccines.

In another aspect, the invention provides methods for identifying candidate compounds for treating, limiting, and/or diagnosing influenza infection, comprising (a) contacting an influenza HA protein with (i) test compounds and (ii) one or more polypeptides of the invention, under conditions suitable for binding of the HA protein to one or more the polypeptide; and (b) identifying those test compounds that out compete the polypeptide for binding to the HA protein, wherein such test compounds are candidate compounds for treating, limiting, and/or diagnosing influenza infection.

Figure 1:
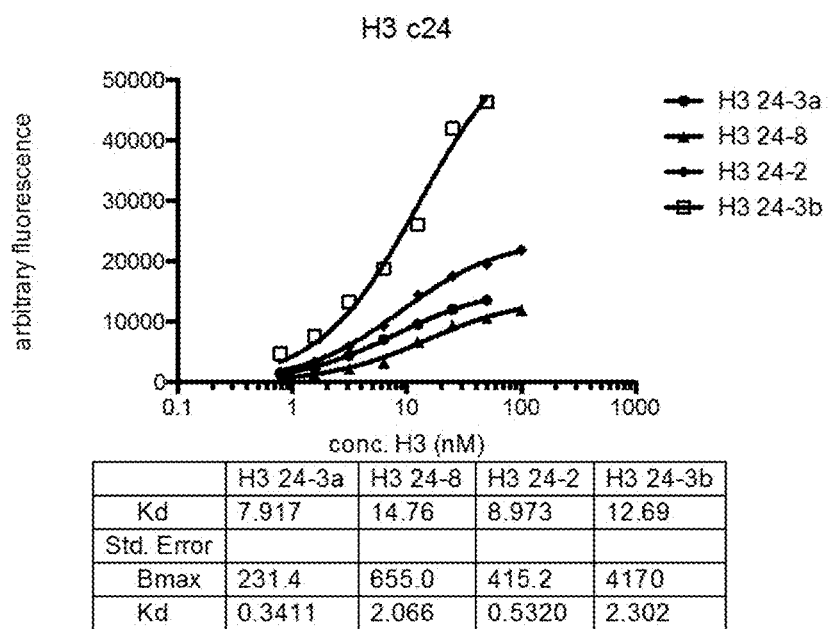
FIG. 1. Binding behaviors of exemplary SB24 variants that were isolated from the first generation library and after 3 rounds of selections. The library was sorted by flow cytometry after introduced 1-2 random nucleotide substitutions via error prone PCR. Titrations were performed by using yeast surface display.

| Residue | AAs |
|---|---|
| 36 | E |
| 37 | N |
| 38 | L, M |
| 39 | N |
| 40 | V, C |
| 41 | K |
| 42 | E, D |
| 43 | Q |
| 44 | Any amino acid |
| 45 | Any amino acid |
| 46 | G (Position 46 and 47 are set so that one of them is glycine and the other is any of the following 17 amino acids; N, H, D, S, K, Y, H, A, V, T, I, Q, D, E, M, L, F) |
| 47 | G (Position 46 and 47 are set so that one of them is glycine and the other is any of the following 17 amino acids; N, H, D, S, K, Y, H, A, V, T, I, Q, D, E, M, L, F) |
| 48 | Any amino acid |
| 49 | M |
| 50 | Y |
| 51 | Y |
| 52 | I |
| 53 | T |
| 54 | L |
| 55 | A |
| 56 | A |
| 57 | T |
| 58 | D |
| 59 | D |
| 60 | A |
| 61 | G |
| 62 | K |
| 63 | K |
| 64 | K |
| 65 | I |
| 66 | Y |
| 67 | K |
| 68 | A |
| 69 | K |
| 70 | I, V |
| 71 | A, G |
| 72 | V |
| 73 | V or is absent |
| 74 | D, E |
| 75 | S |
| 76 | A |
| 77 | G |
| 78 | W |
| 79 | E, V, I, K, A, T |
| 80 | G, V, A |
| 81 | V |
| 82 | Any amino acid |
| 83 | E |
| 84 | F |
| 85 | K |
| 86 | L |
| 87 | V |

The polypeptides of all aspects/embodiments of the invention bind to the sialic acid binding or receptor site of influenza hemagglutinin (HA) protein and can thus be used, for example, to treat or detect/diagnose influenza infection. The polypeptides of the invention provide a cheaper, more selective alternative to currently used hemagglutinin binding antibodies, which are costly to produce. The polypeptides of the invention can also be used for in vivo biosensing applications, whereas the antibodies cannot because of their structurally necessary disulfide bonds and difficulty to express robustly.

The polypeptides of the invention are at least 70% identical with the amino acid sequence of SEQ ID NO:1 (Table 1), over its full length. As disclosed in detail in the examples that follow, numerous HA-binding polypeptides of this embodiment have been identified, and the inventors have discovered that residues 18-27, 44-48, and 70-82 primarily make up the interface for HA protein binding; these regions have been subjected to extensive further analysis to identify variability within these regions. The remaining residues (1-17, 28-43, 49-69, and 83-87) can be modified, as these residues are not involved in the HA protein interface. Such modifications may comprise, for example, conservative amino acid substitutions. Thus, in one preferred embodiment, the polypeptides are at least 70% identical with the amino acid sequence of SEQ ID NO:1, wherein variability is within residues 18-27, 44-48, and/or 70-82. In various embodiments, the polypeptides of the invention are at least 75%, 80%, 85%, 90%, 91%, 92%, 93%, 94%, 95%, 96%, 97%, 98%, 99%, or completely identical with to the amino acid sequence of SEQ ID NO:1 (Table 1), over its full length. In various preferred embodiments, the polypeptides are at least 75%, 80%, 85%, 90%/o, 91%, 92%, 93%, 94%, 95%, 96%, 97%, 98%, 99%, or completely identical with the amino acid sequence of SEQ ID NO:1, wherein variability is within residues 18-27, 44-48, and/or 70-82.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

In one embodiment, the isolated polypeptides comprise or consist of a polypeptide at least 70% identical the amino acid sequence in Table 2.

TABLE 2

(SEQ ID NO: 2)

| Residue | AAs |
|---|---|
| 1 | G, D |
| 2 | I |
| 3 | V |
| 4 | N |
| 5 | V |
| 6 | P |
| 7 | N |
| 8 | P, C |
| 9 | N |
| 10 | N, T |
| 11 | T |
| 12 | K |
| 13 | F, Y |
| 14 | Q |
| 15 | Q |
| 16 | L |
| 17 | A |
| 18 | R |
| 19 | N, R, S, I, Y |
| 20 | A |
| 21 | I |
| 22 | A |
| 23 | N, I, V |
| 24 | Y |
| 25 | N |
| 26 | D, Y, N, H |
| 27 | N, H, Y, Q |
| 28 | Q |
| 29 | N |
| 30 | A |
| 31 | H |
| 32 | L |
| 33 | E |

TABLE 2-continued (SEQ ID NO: 2)

| Residue | AAs |
|---|---|
| 34 | F |
| 35 | V |
| 36 | E |
| 37 | N |
| 38 | L |
| 39 | N |
| 40 | V, C |
| 41 | K |
| 42 | E, D |
| 43 | Q |
| 44 | V, L, I, T, A, S, W, |
| 45 | T, S, D, G, A, N, Y |
| 46 | G, Y, F, A, L, S, E (wherein one of residue 46 or 47 is G) |
| 47 | M, K, G, L, H, Q, E, D, V, S (wherein one of residue 46 or 47 is G) |
| 48 | N, T, V, A, I, D, G, V, S |
| 49 | M |
| 50 | Y |
| 51 | Y |
| 52 | I |
| 53 | T |
| 54 | L |
| 55 | A |
| 56 | A |
| 57 | T |
| 58 | D |
| 59 | D |
| 60 | A |
| 61 | G |
| 62 | K |
| 63 | K |
| 64 | K |
| 65 | I |
| 66 | Y |
| 67 | K |
| 68 | A |
| 69 | K |
| 70 | I, V |
| 71 | A, G |
| 72 | V |
| 73 | V or is absent |
| 74 | D, E |
| 75 | S |
| 76 | A |
| 77 | G |
| 78 | W |
| 79 | E, V, I, K, A, T |
| 80 | G, V, A, E |
| 81 | V |
| 82 | T, E, K, R, D, A, S, N |
| 83 | E |
| 84 | F |
| 85 | K |
| 86 | L |
| 87 | V |

The polypeptides of the invention are at least 70% identical with the amino acid sequence of SEQ ID NO:2 (Table 2), over its full length. In one preferred embodiment, the polypeptides are at least 70% identical with the amino acid sequence of SEQ ID NO:2, wherein variability is within residues 18-27, 44-48, and/or 70-82. In various embodiments, the polypeptides of the invention are at least 75%, 80%, 85%, 90%, 91%, 92%, 93%, 94%, 95%, 96%, 97%, 98%, 99%, or completely identical with to the amino acid sequence of SEQ ID NO:2, over its full length. In various preferred embodiments, the polypeptides are at least 75%, 80%, 85%, 90%, 91%, 92%, 93%, 94%, 95%, 96%, 97%, 98%, 99%, or completely identical with the amino acid sequence of SEQ ID NO:2, wherein variability is within residues 18-27, 44-48, and/or 70-82.

In another embodiment, the isolated polypeptides comprise or consist of a polypeptide at least 70% identical to the amino acid sequence in Table 3.

TABLE 3

(SEQ ID NO: 3)

| Residue | AAs |
|---|---|
| 1 | G |
| 2 | I |
| 3 | V |
| 4 | N |
| 5 | V |
| 6 | P |
| 7 | N |
| 8 | P, C |
| 9 | N |
| 10 | T |
| 11 | T |
| 12 | K |
| 13 | Y |
| 14 | Q |
| 15 | Q |
| 16 | L |
| 17 | A |
| 18 | R |
| 19 | N, R, S, I, Y |
| 20 | A |
| 21 | I |
| 22 | A |
| 23 | I, V, N |
| 24 | Y |
| 25 | N |
| 26 | Y, N, D, H |
| 27 | N, H, Y, Q |
| 28 | Q |
| 29 | N |
| 30 | A |
| 31 | H |
| 32 | L |
| 33 | E |
| 34 | F |
| 35 | V |
| 36 | E |
| 37 | N |
| 38 | L, M |
| 39 | N |
| 40 | V, C |
| 41 | K |
| 42 | E, D |
| 43 | Q |
| 44 | V, L, I, T, A, S, W |
| 45 | T, S, D, G, A |
| 46 | G, Y, L, H, V, S, E (wherein one of residue 46 or 47 is G) |
| 47 | M, K, G, L, H, Q, E, Y, D, S (wherein one of residue 46 or 47 is G) |
| 48 | N, T, V, A, I, D, G, V, S |
| 49 | M |
| 50 | Y |
| 51 | Y |
| 52 | I |
| 53 | T |
| 54 | L |
| 55 | A |
| 56 | A |
| 57 | T |
| 58 | D |
| 59 | D |
| 60 | A |
| 61 | G |
| 62 | K |
| 63 | K |
| 64 | K |
| 65 | I |
| 66 | Y |
| 67 | K |
| 68 | A |
| 69 | K |

TABLE 3-continued (SEQ ID NO: 3)

| Residue | AAs |
| --- | --- |
| 70 | I, V |
| 71 | A, G |
| 72 | V |
| 73 | V or is absent |
| 74 | E |
| 75 | S |
| 76 | A |
| 77 | G, |
| 78 | W |
| 79 | E, V, I, K, A, T |
| 80 | G, A, V, E |
| 81 | V |
| 82 | T, E, S, R, K, N, A |
| 83 | E |
| 84 | F |
| 85 | K |
| 86 | L |
| 87 | V |

The polypeptides of the invention are at least 70% identical with the amino acid sequence of SEQ ID NO:3 (Table 3), over its full length. In one preferred embodiment, the polypeptides are at least 70% identical with the amino acid sequence of SEQ ID NO:3, wherein variability is within residues 18-27, 44-48, and/or 70-82. In various embodiments, the polypeptides of the invention are at least 75%, 80%, 85%, 90%, 91%, 92%, 93%, 94%, 95%, 96%, 97%, 98%, 99%, or completely identical with to the amino acid sequence of SEQ ID NO:3, over its full length. In various preferred embodiments, the polypeptides are at least 75%, 80%, 85%, 90%, 91%, 92%, 93%, 94%, 95%, 96%, 97%, 98%, 99%, or completely identical with the amino acid sequence of SEQ ID NO:3, wherein variability is within residues 18-27, 44-48, and/or 70-82.

In various further embodiments, the SB52 polypeptide comprises or consists of a peptide with an amino acid sequence selected from the group consisting of

```
SB52
                                       (SEQ ID NO: 11)
GIVNVPN(P/C)NNTKFQQLARNAIANYNDNQNAHLEFVENLN(V/C)
KEQVTGGIMYYITLAATDDAGKKKIYKAKIAVVDSAGWEGVTEFKLV;

Variant SB52-3 (G47D, N27Y)
                                       (SEQ ID NO: 12)
GIVNVPN(P/C)NNTKFQQLARNAIANYNDYQNAHLEFVENLN(V/C)
KEQVTGDIMYYITLAATDDAGKKKIYKAKIAVVDSAGWEGVTEFKLV;

Variant H2 SB52-4 (N19Y, E79V)
                                       (SEQ ID NO: 13)
GIVNVPN(P/C)NNTKFQQLARYAIANYNDNQNAHLEFVENLN(V/C)
KEQVTGGIMYYITLAATDDAGKKKIYKAKIAVVDSAGWVGVTEFKLV;

Variant H2 SB52-13 (N7K, N19Y, E79V)
                                       (SEQ ID NO: 14)
GIVNVPK(P/C)NNTKFQQLARYAIANYNDNQNAHLEFVENLN(V/C)
KEQVTGGIMYYITLAATDDAGKKKIYKAKIAVVDSAGAWVGVTEFKLV;

52solo1
                                       (SEQ ID NO: 15)
GIVNVPN(P/C)NTTKYQQLARSAIAIYNYHQNAHLEFVENLN(V/C)
KEQVGGMNMYYITLAATDDAGKKKIYKAKVGVVESAGWKGVEEFKLV;

52solo2
                                       (SEQ ID NO: 16)
GIVNVPN(P/C)NTTKYQQLARSAIAVYNYHQNAHLEFVENLN(V/C)
KEQIAGKTMYYITLAATDDAGKKKIYKAKVGVVESAGWEGVEEFKLV;

52solo3
                                       (SEQ ID NO: 17)
GIVNVPN(P/C)NTTKYQQLARIAIAVYNNYQNAHLEFVENLN(V/C)
KEQSGGKVMYYITLAATDDAGKKKIYKAKVGVVESAGWIGVEEFKLV;

52solo8
                                       (SEQ ID NO: 18)
GIVNVPN(P/C)NTTKYQQLARSAIAVYNNHQNAHLEFVENLN(V/C)
KEQAGGKAMYYITLAATDDAGKKKIYKAKIGVVESAGWEGVEEFKLV;

52sing2
                                       (SEQ ID NO: 19)
GIVNVPN(P/C)NTTKYQQLARRAIAIYNNNQNAHLEFVENLN(V/C)
KEQTGLGIMYYITLAATDDAGKKKIYKAKIAVVESAGWVAVSEFKLV;

52solo8a
                                       (SEQ ID NO: 20)
GIVNVPN(P/C)NTTKYQQLARSAIAVYNNHQNAHLEFVENLN(V/C)
KEQAGGKAMYYITLAATDDAGKKKIYKAKIGVVESAGWEGVEEFKLV;

52solo8b
                                       (SEQ ID NO: 21)
GIVNVPN(P/C)NTTKYQQLARSAIAVYNYHQNAHLEFVENLN(V/C)
KEQIAGKTMYYITLAATDDAGKKKIYKAKVGVVESAGWEGVEEFKLV;

52soloc
                                       (SEQ ID NO: 22)
GIVNVPN(P/C)NTTKYQQLARSAIAVYNNHQNAHLEFVENLN(V/C)
KEQAGGKAMYYITLAATDDAGKKKIYKAKIGVVESAGWEGVEEFKLV;

52sing2
                                       (SEQ ID NO: 23)
GIVNVPN(P/C)NTTKYQQLARRAIAIYNNNQNAHLEFVENLN(V/C)
KEQTGLGIMYYITLAATDDAGKKKIYKAKIAVVESAGWVAVSEFKLV;

52sing2W
                                       (SEQ ID NO: 24)
GIVNVPN(P/C)NTTKYQQLARRAIAIYNNNQNAHLEFVENLN(V/C)
KEQWGLGIMYYITLAATDDAGKKKIYKAKIAVVESAGWVAVSEFKLV;

52sing2D
                                       (SEQ ID NO: 25)
GIVNVPN(P/C)NTTKYQQLARRAIAIYNNNQNAHLEFVENLN(V/C)
KDQTGLGIMYYITLAATDDAGKKKIYKAKIAVVESAGWVAVSEFKLV;

52alt1-3
                                       (SEQ ID NO: 26)
GIVNVPN(P/C)NTTKYQQLARSAIAIYNNHQNAHLEFVENLN(V/C)
KEQVSYGAMYYITLAATDDAGKKKIYKAKVGVVESAGWVGVEEFKLV;

52alt1-4
                                       (SEQ ID NO: 27)
GIVNVPN(P/C)NTTKYQQLARSAIAVYNYHQNAHLEFVENLN(V/C)
KEQIDYGAMYYITLAATDDAGKKKIYKAKIGVVESAGWIGVEEFKLV;

52vic5-2
                                       (SEQ ID NO: 28)
GIVNVPN(P/C)NTTKYQQLARRAIAIYNNNQNAHLEFVENLN(V/C)
KEQWGLGIMYYITLAATDDAGKKKIYKAKIAVVESAGWVAVSEFKLV;
```

52vic5-3
(SEQ ID NO: 29)
GIVNVPN(P/C)NTTKYQQLARSAIAIYNNNQNAHLEFVENLN(V/C)
KEQLNGYDMYYITLAATDDAGKKKIYKAKIGVVESAGWTGVNEFKLV;

52vic5-4
(SEQ ID NO: 30)
GIVNVPN(P/C)NTTKYQQLARSAIAIYNHYQNAHLEFVENLN(V/C)
KEQITGYDMYYITLAATDDAGKKKIYKAKVAVVESAGWEVVAEFKLV;

52del1
(SEQ ID NO: 31)
GIVNVPN(P/C)NTTKYQQLARRAIAVYNYYQNAHLEFVENLN(V/C)
KEQSSGLDMYYITLAATDDAGKKKIYKAKIAVESAGWIVVTEFKLV;

52del4
(SEQ ID NO: 32)
GIVNVPN(P/C)NTTKYQQLARRAIAVYNYYQNAHLEFVENLN(V/C)
KEQLTGHGMYYITLAATDDAGKKKIYKAKVAVESAGWIVVTEFKLV;

52del2
(SEQ ID NO: 33)
GIVNVPN(P/C)NTTKYQQLARRAIAVYNYYQNAHLEFVENLN(V/C)
KEQAGGQVMYYITLAATDDAGKKKIYKAKVAVESAGWIVVTEFKLV;

52del3
(SEQ ID NO: 34)
GIVNVPN(P/C)NTTKYQQLARRAIAVYNYYQNAHLEFVENLN(V/C)
KEQAAGEIMYYITLAATDDAGKKKIYKAKIAVESAGWIVVREFKLV;

52del5
(SEQ ID NO: 35)
GIVNVPN(P/C)NTTKYQQLARRAIAVYNYYQNAHLEFVENLN(V/C)
KEQAAGEIMYYITLAATDDAGKKKIYKAKIAVESAGWIVVREFKLV;

52del6
(SEQ ID NO: 36)
GIVNVPN(P/C)NTTKYQQLARIAIAIYNYHQNAHLEFVENLN(V/C)
KEQSGHGTMYYITLAATDDAGKKKIYKAKVGVVESAGWIGVTEFKLV;

52del7
(SEQ ID NO: 37)
GIVNVPN(P/C)NTTKYQQLARIAIAVYNHHQNAHLEFVENLN(V/C)
KEQISVGTMYYITLAATDDAGKKKIYKAKVGVVESAGWIEVEEFKLV;

52del8
(SEQ ID NO: 38)
GIVNVPN(P/C)NTTKYQQLARRAIAVYNYYQNAHLEFVENLN(V/C)
KEQLTLGVMYYITLAATDDAGKKKIYKAKVAV-ESAGWIVVTEFKLV;

52del9
(SEQ ID NO: 39)
GIVNVPN(P/C)NTTKYQQLARRAIAVYNYYQNAHLEFVENLN(V/C)
KEQSSSGNMYYITLAATDDAGKKKIYKAKIAV-ESAGWIVVKEFKLV;

52-N19S
(SEQ ID NO: 131)
GIVNVPN(P/C)NNTKFQQLARSAIANYNDYQNAHLEFVENLN(V/C)
KEQVTGDIMYYITLAATDDAGKKKIYKAKIAVVDSAGWEGVTEFKLV

52-N19Y
(SEQ ID NO: 132)
GIVNVPN(P/C)NNTKFQQLARYAIANYNDYQNAHLEFVENLN(V/C)
KEQVTGDIMYYITLAATDDAGKKKIYKAKIAVVDSAGWEGVTEFKLV

52-L38M
(SEQ ID NO: 133)
GIVNVPN(P/C)NNTKFQQLARNAIANYNDYQNAHLEFVENMN(V/C)
KEQVTGDIMYYITLAATDDAGKKKIYKAKIAVVDSAGWEGVTEFKLV

52-G47D
(SEQ ID NO: 134)
GIVNVPN(P/C)NNTKFQQLARNAIANYNDYQNAHLEFVENLN(V/C)
KEQVTDDIMYYITLAATDDAGKKKIYKAKIAVVDSAGWEGVTEFKLV

52NC-1
(SEQ ID NO: 95)
GIVNVPN(P/C)NTTKYQQLARIAIAVYNHHQNAHLEFVENLN(V/C)
KEQLGEGDMYYITLAATDDAGKKKIYKAKVGVVESAGWTGVEEFKLV;

52NC-2
(SEQ ID NO: 96)
GIVNVPN(P/C)NTTKYQQLARSAIAIYNHQNAHLEFVENLN(V/C)
KEQLGEGDMYYITLAATDDAGKKKIYKAKIGVVESAGWTGVEEFKLV;

52NC-8
(SEQ ID NO: 97)
GIVNVPN(P/C)NTTKYQQLARSAIAIYNYHQNAHLEFVENLN(V/C)
KEQIGEGSMYYITLAATDDAGKKKIYKAKVGVVESAGWEGVEEFKLV;
and 52solo6
(SEQ ID NO: 126)
GIVNVPN(P/C)NTTKYQQLARRAIAIYNHNQNAHLEFVENLN(V/C)
KEQIDYGSMYYITLAATDDAGKKKIYKAKVGVVESSGWTGVEEFKLV.

In a second aspect, the invention provides isolated polypeptides comprising or consisting of a polypeptide at least 70% identical over the full length of the amino acid sequence in Table 4, wherein the polypeptide does not comprise the amino acid sequence of (SEQ ID NO: 130)
MINMKVAISMDVDKISNSFEDCKYFLIVRIDDNEVKSTKVIFNDESGKK

SIVKENVNAIICKNISEENYKKFSKKIEIYHAEGDDVDKNISLFIEGEL

SKISNP:

TABLE 4

| SB24 Genus (SEQ ID NO: 4) | |
|---|---|
| Residue | AAs |
| 1 | G, A |
| 2 | I, S, T |
| 3 | G |
| 4 | M |
| 5 | V, L |
| 6 | A |
| 7 | I |
| 8 | S |
| 9 | M |
| 10 | D |
| 11 | T |
| 12 | D |
| 13 | K |
| 14 | I |
| 15 | S |
| 16 | N |
| 17 | S |
| 18 | F |
| 19 | E |
| 20 | D |

TABLE 4-continued

SB24 Genus (SEQ ID NO: 4)

| Residue | AAs |
|---|---|
| 21 | C |
| 22 | K |
| 23 | Y |
| 24 | F |
| 25 | Any amino acid |
| 26 | M, L, F, I, E |
| 27 | Any amino acid |
| 28 | V, M, I, L |
| 29 | V, A, S, P, E, D, Q, N, V, T, K |
| 30 | S |
| 31 | A |
| 32 | G |
| 33 | W, G |
| 34 | T, I, V, D, E |
| 35 | N |
| 36 | T |
| 37 | I |
| 38 | F, I, L, T, S |
| 39 | N |
| 40 | D |
| 41 | E |
| 42 | S |
| 43 | G |
| 44 | K |
| 45 | K, E |
| 46 | E |
| 47 | I, L |
| 48 | V |
| 49 | K, E, M, N |
| 50 | M |
| 51 | N, D, E, S, G |
| 52 | V |
| 53 | D |
| 54 | A |
| 55 | I |
| 56 | I |
| 57 | C |
| 58 | K |
| 59 | N |
| 60 | I |
| 61 | S |
| 62 | E |
| 63 | E |
| 64 | N |
| 65 | Y |
| 66 | K |
| 67 | K, E, R |
| 68 | F |
| 69 | S |
| 70 | K |
| 71 | K, E |
| 72 | I |
| 73 | E |
| 74 | I |
| 75 | Y |
| 76 | H |
| 77 | A |
| 78 | E |
| 79 | G |
| 80 | D |
| 81 | D |
| 82 | V |
| 83 | D, N, K, E |
| 84 | K |
| 85 | N |
| 86 | I |
| 87 | S |
| 88 | L |
| 89 | F, I, L |
| 90 | I, L, M, T, V, A |
| 91 | E, D, K, R, G |
| 92 | G |
| 93 | E |
| 94 | L |
| 95 | S |
| 96 | K |

TABLE 4-continued

SB24 Genus (SEQ ID NO: 4)

| Residue | AAs |
|---|---|
| 97 | I |
| 98 | S |
| 99 | N |
| 100 | P |

As disclosed in detail in the examples that follow, numerous HA-binding polypeptides of this embodiment have been identified, and the inventors have discovered that residues 1-3, 25-38, 45-51, and position 83 primarily make up the interface for HA protein binding; these regions have been subjected to extensive further analysis to identify variability within these regions. The remaining residues (4-24, 39-44, 52-82, and 84 to 100) can be modified, as these residues are not involved in the HA protein interface. Such modifications may comprise, for example, conservative amino acid substitutions. Thus, in one preferred embodiment, the polypeptides are at least 70% identical with the amino acid sequence of SEQ ID NO:4, wherein variability is within residues 4-24, 39-44, 52-82, and 84 to 100. In various embodiments, the polypeptides of the invention are at least 75%, 80%, 85%, 90%, 91%, 92%, 93%, 94%, 95%, 96%, 97%, 98%, 99%, or completely identical with to the amino acid sequence of SEQ ID NO:4 (Table 4), over its full length. In various preferred embodiments, the polypeptides are at least 75%, 80%, 85%, 90%, 91%, 92%, 93%, 94%, 95%, 96%, 97%, 98%, 99%, or completely identical with the amino acid sequence of SEQ ID NO:4, wherein variability is within residues 4-24, 39-44, 52-82, and 84 to 100.

In one embodiment, the isolated polypeptides comprise or consist of a polypeptide at least 70% identical to the amino acid sequence in Table 5.

TABLE 5

(SEQ ID NO: 5)

| Residue | AAs |
|---|---|
| 1 | G, A |
| 2 | I, S, T |
| 3 | G |
| 4 | M |
| 5 | V, L |
| 6 | A |
| 7 | I |
| 8 | S |
| 9 | M |
| 10 | D |
| 11 | T |
| 12 | D |
| 13 | K |
| 14 | I |
| 15 | S |
| 16 | N |
| 17 | S |
| 18 | F |
| 19 | E |
| 20 | D |
| 21 | C |
| 22 | K |
| 23 | Y |
| 24 | F |
| 25 | L, Q |
| 26 | L, I, E |
| 27 | M, V, E, Y |
| 28 | V, M, L |
| 29 | V, P, E, K, L, A |
| 30 | S |

TABLE 5-continued (SEQ ID NO: 5)

| Residue | AAs |
|---|---|
| 31 | A |
| 32 | G |
| 33 | W |
| 34 | T |
| 35 | N |
| 36 | T |
| 37 | I |
| 38 | F, S |
| 39 | N |
| 40 | D |
| 41 | E |
| 42 | S |
| 43 | G |
| 44 | K |
| 45 | K, E |
| 46 | E |
| 47 | I |
| 48 | V |
| 49 | K, E |
| 50 | M |
| 51 | N, G, S |
| 52 | V |
| 53 | D |
| 54 | A |
| 55 | I |
| 56 | I |
| 57 | C |
| 58 | K |
| 59 | N |
| 60 | I |
| 61 | S |
| 62 | E |
| 63 | E |
| 64 | N |
| 65 | Y |
| 66 | K |
| 67 | K |
| 68 | F |
| 69 | S |
| 70 | K |
| 71 | K |
| 72 | I |
| 73 | E |
| 74 | I |
| 75 | Y |
| 76 | H |
| 77 | A |
| 78 | E |
| 79 | G |
| 80 | D |
| 81 | D |
| 82 | V |
| 83 | D, N, K, E |
| 84 | K |
| 85 | N |
| 86 | I |
| 87 | S |
| 88 | L |
| 89 | F |
| 90 | I, L, A |
| 91 | E |
| 92 | G |
| 93 | E |
| 94 | L |
| 95 | S |
| 96 | K |
| 97 | I |
| 98 | S |
| 99 | N |
| 100 | P |

In one preferred embodiment, the polypeptides are at least 70% identical with the amino acid sequence of SEQ ID NO:5, wherein variability is within residues 4-24, 39-44, 52-82, and 84 to 100. In various embodiments, the polypeptides of the invention are at least 75%, 80%, 85%, 90%, 91%, 92%, 93%, 94%, 95%, 96%, 97%, 98%, 99%, or completely identical with to the amino acid sequence of SEQ ID NO:5 over its full length. In various preferred embodiments, the polypeptides are at least 75%, 80%, 85%, 90%, 91%, 92%, 93%, 94%, 95%, 96%, 97%, 98%, 99%, or completely identical with the amino acid sequence of SEQ ID NO:5, wherein variability is within residues 1-24, 39-44, 52-82, and 84 to 100.

In various further embodiments, the SB24 polypeptide comprises or consists of a polypeptide with an amino acid sequence selected from the group consisting of

SB24
(SEQ ID NO: 40)
GIGMVAISMDTDKISNSFEDCKYFLIVVVSAGWTNTIFNDESGKKEIVK

MNVDAIICKNISEENYKKFSKKIEIYHAEGDDVDKNISLFIEGELSKIS

NP;

Variant H3 24-2 (V27M, F38S, K49E)
(SEQ ID NO: 41)
GIGMVAISMDTDKISNSFEDCKYFLIMVVSAGWTNTISNDESGKKEIVE

MNVDAIICKNISEENYKKFSKKIEIYHAEGDDVDKNISLFIEGELSKIS

NP;

Variant H3 24-3a (I2T, V29E)
(SEQ ID NO: 42)
GIGMVAISMDTDKISNSFEDCKYFLIVVESAGWTNTIFNDESGKKEIVK

MNVDAIICKNISEENYKKFSKKIEIYHAEGDDVDKNISLFIEGELSKIS

NP;

Variant H3 24-3b (V28M)
(SEQ ID NO: 43)
GTGMVAISMDTDKISNSFEDCKYFLIVMVSAGWTNTIFNDESGKKEIVK

MNVDAIICKNISEENYKKFSKKIEIYHAEGDDVDKNISLFIEGELSKIS

NP;

Variant H3 24-8 (V27M, K49E)
(SEQ ID NO: 44)
GTGMVAISMDTDKISNSFEDCKYFLIMVVSAGWTNTIFNDESGKKEIVE

MNVDAIICKNISEENYKKFSKKIEIYHAEGDDVDKNISLFIEGELSKIS

NP;

SB24solo2
(SEQ ID NO: 45)
ASGMLAISMDTDKISNSFEDCKYFLIELKSAGWTNTIFNDESGKEEIV

MGVDAIICKNISEENYKKFSKKIEIYHAEGDDVNKNISLFLEGELSKIS

NP;

SB24solo6
(SEQ ID NO: 46)
ASGMLAISMDTDKISNSFEDCKYFQLELPSAGWTNTIFNDESGKEEIVK

MNVDAIICKNISEENYKKFSKKIEIYHAEGDDVKKNISLFLEGELSKIS

NP;

SB24NC1
(SEQ ID NO: 47)
ASGMLAISMDTDKISNSFEDCKYFQIELPSAGGTNTIFNDESGKEEIVK

MGVDAIICKNISEENYKKFSKKIEIYHAEGDDVKKNISLFIEGELSKIS

NP;

-continued

SB24alt1-1
(SEQ ID NO: 125)
ASGMLAISMDTDKISNSFEDCKYFQLYVLSAGWTNTIFNDESGKEEIVK

MSVDAIICKNISEENYKKFSKKIEIYHAEGDDVDKNISLFLEGELSKIS

NP;

SB24SingNC1
(SEQ ID NO: 127)
ASGMLAISMDTDKISNSFEDCKYFQIELPSAGWTNTIFNDESGKEEIVK

MGVDAIICKNISEENYKKFSKKIEIYHAEGDDVEKNISLFLEGELSKIS

NP;
and

SB24SingNC3
(SEQ ID NO: 128)
ASGMLAISMDTDKISNSFEDCKYFQLVLASAGWTNTIFNDESGKEEIVK

MGVDAIICKNISEENYKKFSKKIEIYHAEGDDVDKNISLFAEGELSKIS

NP.

In a further aspect, the invention provides isolated polypeptides comprising or consisting of the amino acid sequence in Table 6:

TABLE 6

| Disulfide genus (SEQ ID NO: 6) | |
|---|---|
| Residue # | Amino acids |
| 1 | G |
| 2 | Any amino acid |
| 3 | C |
| 4 | Any amino acid |
| 5 | Any amino acid |
| 6 | V, M |
| 7 | P, A, T, I, L, V |
| 8 | S |
| 9 | A |
| 10 | G |
| 11 | W |
| 12 | E, V, T, I, A, K |
| 13 | Any amino acid |
| 14 | C |
| 15 | Any amino acid or is absent |

The polypeptides of this aspect of the invention can assume a hairpin-like structure that can be stabilized through a disulfide bridge by the cysteine residues at a non-hydrogen bonding beta strand pair. In one embodiment, the polypeptides comprise or consist of the amino acid sequence in Table 7:

TABLE 7

| (SEQ ID NO: 7) | |
|---|---|
| Residue # | Amino acids |
| 1 | G |
| 2 | G, W, R, H, D, Y, E, Q, C |
| 3 | C |
| 4 | I, L, M, F |
| 5 | G |
| 6 | V |
| 7 | P, A |
| 8 | S |
| 9 | A |
| 10 | G |
| 11 | W |
| 12 | E, V, T, I, A, K |

TABLE 7-continued

| (SEQ ID NO: 7) | |
|---|---|
| Residue # | Amino acids |
| 13 | W, I, V, R, M, G, L, V |
| 14 | C |
| 15 | P, W, D, R, S, A, E, Y, H, Q, C, G |

In a further embodiment, the polypeptides comprise or consist of the amino acid sequence in Table 8:

TABLE 8

| (SEQ ID NO: 8) | |
|---|---|
| Residue # | Amino acids |
| 1 | G |
| 2 | G, W, R, H, |
| 3 | C |
| 4 | I, L, M |
| 5 | G |
| 6 | V |
| 7 | P, A |
| 8 | S |
| 9 | A |
| 10 | G |
| 11 | W |
| 12 | E, V, T, I |
| 13 | W, I, V, R |
| 14 | C |
| 15 | P, W, D, R, |

In various further embodiments, the polypeptides comprise or consist of a polypeptide selected from the group consisting of:

(SEQ ID NO: 48)
GXCIGVPSAGWEXCW;

(SEQ ID NO: 49)
GGCIGVPSAGWEWCP;

(SEQ ID NO: 50)
GGCLGVPSAGWEICW;

(SEQ ID NO: 51)
GWCIGVPSAGWEICW;

(SEQ ID NO: 52)
GRCIGVPSAGWEVCW;

(SEQ ID NO: 53)
GHCMGVASAGWEICW;
and (SEQ ID NO: 54)
GDCIGVASAGWEWCP.

In another embodiment, the polypeptides comprise or consist of the amino acid sequence in Table 9.

TABLE 9

| (SEQ ID NO: 9) | |
|---|---|
| Residue | Options |
| 1 | G |
| 2 | G, W, R, H, D, Y |
| 3 | C |
| 4 | I, L, M |
| 5 | G |
| 6 | V |
| 7 | P, A |

TABLE 9-continued (SEQ ID NO: 9)

| Residue | Options |
|---|---|
| 8 | S |
| 9 | A |
| 10 | G |
| 11 | W |
| 12 | E |
| 13 | W, I, V |
| 14 | C |
| 15 | W, P |

In various further embodiments, the polypeptides comprise or consist of a polypeptide selected from the group consisting of:

```
                                    (SEQ ID NO: 55)
GGCIGVPSAGWEWCP;

(SEQ ID NO: 56)
GGCLGVPSAGWEWCP;

(SEQ ID NO: 57)
GWCIGVPSAGWEICW;

(SEQ ID NO: 58)
GWCIGVPSAGWEICW;

(SEQ ID NO: 59)
GRCIGVPSAGWEVCW;

(SEQ ID NO: 60)
GHCMGVASAGWEICW;

(SEQ ID NO: 61)
GDCIGVASAGWEWCP;

(SEQ ID NO: 62)
GYCIGVPSAGWEVCW;

(SEQ ID NO: 63)
GYCIGVPSAGWEICW;
and
                                    (SEQ ID NO: 64)
GWCMGVPSAGWEICW.
```

In another embodiment, the polypeptides comprise or consist of the amino acid sequence in Table 10.

TABLE 10

(SEQ ID NO: 10)

| Residue | Options |
|---|---|
| 1 | G |
| 2 | S, F, D, C, M, N, K, G, T, R, W, V |
| 3 | C |
| 4 | P, C, T, G, F, R, A, Y, I, W, V |
| 5 | F, L, C, Y, H, A, W, R, V, P, G, K |
| 6 | V, M, A |
| 7 | T, I, L, V, A |
| 8 | S |
| 9 | A |
| 10 | G |
| 11 | W |
| 12 | E |
| 13 | K, E, P, M, V, I, T, A, G |
| 14 | C |
| 15 | L, Y, E, S, K, A, N, R, V, or is absent |

In various further embodiments, the polypeptides comprise or consist of a polypeptide selected from the group consisting of:

```
                                    (SEQ ID NO: 65)
GSCYRVVSAGWETC;

(SEQ ID NO: 65)
GSCYRVVSAGWETC;

(SEQ ID NO: 67)
GGCARVASAGWEICN;

(SEQ ID NO: 68)
GKCRWVASAGWEVCA;

(SEQ ID NO: 69)
GNCFAVVSAGWEKCK;

(SEQ ID NO: 70)
GMCTHVLSAGWEPCL;

(SEQ ID NO: 71)
GMCTHVLSAGWEPCL;

(SEQ ID NO: 72)
GCCGYVISAGWEMCS;

(SEQ ID NO: 73)
GDCTCMISAGWEPCE;

(SEQ ID NO: 74)
GFCCLVTSAGWEECY;

(SEQ ID NO: 75)
GFCCLVTSAGWEECY;

(SEQ ID NO: 76)
GSCPFVTSAGWEKCL;

(SEQ ID NO: 78)
GDCIVVASAGWEACR;

(SEQ ID NO: 80)
GRCICALSAGWETCA;

(SEQ ID NO: 81)
GWCWGVISAGWEGCR;
and
                                    (SEQ ID NO: 82)
GVCVKVASAGWEECV.
```

In a further aspect, the polypeptides of the invention comprise or consist of a polypeptide selected from the group consisting of the following, each of which is shown in the examples that follow to strongly bind the HA protein:

SB53
```
                                    (SEQ ID NO: 85)
GIVNVPNPNNTKFQQLARNAIQNYNDNQNAHLEFVENLNVKEQVTGGIMY

YITLAATDDAGKKKIYKAKIAVVDSAGWEGITEFKLV;
```

SB55
```
                                    (SEQ ID NO: 86)
GIVNVPNPNNTKFQQLARSAIQNYNDNQNAHLEFVENLNVKEQVTGGIMY

YITLAATDDAGKKKIYKAKIAVVDSAGWEGITEFKLV;
```

SB41
```
                                    (SEQ ID NO: 87)
KEITNALETWGALGQDINLDIPSFQMSDDIADIKWEKTQDNKMIVVFSAG

WIAKDTYDLYENGTLKIAHLTTDDQAIYKVSITDTKGKNVLEKIFDLKIQ

ERVSKPKISWTCINTTLTCEVMNGTDPELNLYQDGKHLKLSQRVITHKWT

TSLSAKFKCTAGNKVSKESSVEPVSCPEK
```

SB60
(SEQ ID NO: 88)
KIIITGEPGVGKTTLYKKIVERLGKRAIGFWTEEVTDPETKKRTGFRIIT

TEGKKKVFSVVSAGWESKQNFEELAIPILERAYREAKKDRRKVIIIDEIG

DALGSSKFRDLVRQIHDPNVNVVATIPIRDDAPLIKEIRRLPGAVLIELT

PENRDVILEDILSLLER;
and

SB23
(SEQ ID NO: 89)
GHPTLKTPESVTGTWKGDVKIQCIYDPLRGYEQTEVKWLVRHGSDSVTIF

ERVSSAGWDGISQDKYNGRLQVSDSVPGDVSLQINTLQMDDRNHYTCEVT

WQTPDGNQVIRDKIIELRVRK.

As used throughout the present application, the term "polypeptide" is used in its broadest sense to refer to a sequence of subunit amino acids. The polypeptides of the invention may comprise L-amino acids, D-amino acids (which are resistant to L-amino acid-specific proteases in vivo), or a combination of D- and L-amino acids. The polypeptides described herein may be chemically synthesized or recombinantly expressed. The polypeptides may be linked to other compounds to promote an increased half-life in vivo, such as by PEGylation, HESylation, PASylation, glycosylation, etc. Such linkage can be covalent or non-covalent as is understood by those of skill in the art.

In a further embodiment, the polypeptides of any embodiment of any aspect of the invention may further comprise a tag, such as a detectable moiety or therapeutic agent. The tag(s) can be linked to the polypeptide through covalent bonding, including, but not limited to, disulfide bonding, hydrogen bonding, electrostatic bonding, recombinant fusion and conformational bonding. Alternatively, the tag(s) can be linked to the polypeptide by means of one or more linking compounds. Techniques for conjugating tags to polypeptides are well known to the skilled artisan. Polypeptides comprising a detectable tag can be used diagnostically to, for example, assess if a subject has been infected with influenza virus or monitor the development or progression of an influenza virus infection as part of a clinical testing procedure to, e.g., determine the efficacy of a given treatment regimen. However, they may also be used for other detection and/or analytical and/or diagnostic purposes. Any suitable detection tag can be used, including but not limited to enzymes, prosthetic groups, fluorescent materials, luminescent materials, bioluminescent materials, radioactive materials, positron emitting metals, and nonradioactive paramagnetic metal ions. The tag used will depend on the specific detection/analysis/diagnosis techniques and/or methods used such as immunohistochemical staining of (tissue) samples, flow cytometric detection, scanning laser cytometric detection, fluorescent immunoassays, enzyme-linked immunosorbent assays (ELISAs), radioimmunoassays (RIAs), bioassays (e.g., neutralization assays), Western blotting applications, etc. For immunohistochemical staining of tissue samples preferred tags are enzymes that catalyze production and local deposition of a detectable product. Enzymes typically conjugated to polypeptides to permit their immunohistochemical visualization are well known and include, but are not limited to, acetylcholinesterase, alkaline phosphatase, beta-galactosidase, glucose oxidase, horseradish peroxidase, and urease. Typical substrates for production and deposition of visually detectable products are also well known to the skilled person in the art. The polypeptides can be labeled using colloidal gold or they can be labeled with radioisotopes, such When the polypeptides of the invention are used for flow cytometric detections, scanning laser cytometric detections, or fluorescent immunoassays, the tag may comprise, for example, a fluorophore. A wide variety of fluorophores useful for fluorescently labeling the polypeptides of the invention are known to the skilled artisan. When the polypeptides are used for in vivo diagnostic use, the tag can comprise, for example, magnetic resonance imaging (MRI) contrast agents, such as gadolinium diethylenetriaminepentaacetic acid, to ultrasound contrast agents or to X-ray contrast agents, or by radioisotopic labeling.

The polypeptides of the invention can also be attached to solid supports, which are particularly useful for in vitro assays or purification of influenza virus or HA protein. Such solid supports might be porous or nonporous, planar or nonplanar and include, but are not limited to, glass, cellulose, polyacrylamide, nylon, polystyrene, polyvinyl chloride or polypropylene supports. The polypeptides can also, for example, usefully be conjugated to filtration media, such as NHS-activated Sepharose or CNBr-activated Sepharose for purposes of affinity chromatography. They can also usefully be attached to paramagnetic microspheres, typically by biotin-streptavidin interaction. The microspheres can be used for isolation of influenza virus or HA protein from a sample containing influenza virus or HA protein. As another example, the polypeptides of the invention can usefully be attached to the surface of a microtiter plate for ELISA.

The polypeptides of the invention can be fused to marker sequences to facilitate purification. Examples include, but are not limited to, the hexa-histidine tag, the myc tag or the flag tag.

The polypeptides of the invention can be conjugated to an antigen recognized by the immune system of a subject to which the polypeptide is administered. Conjugation methods for attaching the antigens and polypeptide are well known in the art and include, but are not limited to, the use of cross-linking agents. The polypeptide will bind to the influenza virus HA protein and the antigen will initiate a T-cell attack on the conjugate that will facilitate destruction of the influenza virus.

In another embodiment of any aspect herein, the present invention provides retro-inverso polypeptides corresponding to the polypeptides of the invention. Retro-inverso polypeptides of the invention comprise or consist of D-amino acids assembled in a reverse order from that of L-sequence polypeptide versions of the polypeptides disclosed above, thus maintaining the overall topology of the polypeptide, and maintaining HA binding.

In another aspect, the present invention provides antibodies that selectively bind to the polypeptides of the invention. The antibodies can be polyclonal, monoclonal antibodies, humanized antibodies, and fragments thereof, and can be made using techniques known to those of skill in the art. As used herein, "selectively bind" means preferential binding of the antibody to the polypeptide of the invention, as opposed to one or more other biological molecules, structures, cells, tissues, etc., as is well understood by those of skill in the art.

In a further aspect, the present invention provides pharmaceutical compositions, comprising one or more polypeptides of the invention and a pharmaceutically acceptable carrier. In this embodiment, the polypeptides of the invention may be used, for example, in any of the methods of the present invention. The pharmaceutical composition may comprise in addition to the polypeptide of the invention (a)

a lyoprotectant; (b) a surfactant; (c) a bulking agent: (d) a tonicity adjusting agent; (e) a stabilizer, (f) a preservative and/or (g) a buffer.

In some embodiments, the buffer in the pharmaceutical composition is a Tris buffer, a histidine buffer, a phosphate buffer, a citrate buffer or an acetate buffer. The pharmaceutical composition may also include a lyoprotectant, e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the pharmaceutical composition includes a bulking agent, like glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The polypeptides may be the sole active agent in the pharmaceutical composition, or the composition may further comprise one or more other active agents suitable for an intended use, including but not limited to anti-HA and anti-NA antibodies.

In a further aspect, the present invention provides isolated nucleic acids encoding a polypeptide of the present invention. The isolated nucleic acid sequence may comprise RNA or DNA. As used herein, "isolated nucleic acids" are those that have been removed from their normal surrounding nucleic acid sequences in the genome or in cDNA sequences. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the polypeptides of the invention.

In another aspect, the present invention provides recombinant expression vectors comprising the isolated nucleic acid of any aspect of the invention operatively linked to a suitable control sequence. "Recombinant expression vector" includes vectors that operatively link a nucleic acid coding region or gene to any control sequences capable of effecting expression of the gene product. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors.

In a still further aspect, the present invention provides host cells that have been transfected with the recombinant expression vectors disclosed herein, wherein the host cells can be either prokaryotic (such as bacteria) or eukaryotic. The cells can be transiently or stably transfected. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique*. $2^{nd}$ Ed. (R. I. Freshney. 1987. Liss, Inc. New York, N.Y.).

A method of producing a polypeptide according to the invention is an additional part of the invention. The method comprises the steps of (a) culturing a host according to this aspect of the invention under conditions conducive to the expression of the polypeptide, and (b) optionally, recovering the expressed polypeptide.

In another aspect, the present invention provides methods for treating and/or limiting an influenza infection, comprising administering to a subject in need thereof a therapeutically effective amount of one or more polypeptides of the invention, salts thereof, conjugates thereof, or pharmaceutical compositions thereof, to treat and/or limit the influenza infection. When the method comprises treating an influenza infection, the one or more polypeptides are administered to a subject that has already been infected with the influenza virus, and/or who is suffering from symptoms (including but not limited to chills, fever, sore throat, muscle pains, coughing, weakness, fatigue, and general discomfort) indicating that the subject is likely to have been infected with the influenza virus. As used herein, "treat" or "treating" means accomplishing one or more of the following: (a) reducing influenza viral titer in the subject; (b) limiting any increase of influenza viral titer in the subject; (c) reducing the severity of flu symptoms; (d) limiting or preventing development of flu symptoms after infection; (e) inhibiting worsening of flu symptoms; (f) limiting or preventing recurrence of flu symptoms in subjects that were previously symptomatic for influenza infection.

When the method comprises limiting an influenza infection, the one or more polypeptides are administered prophylactically to a subject that is not known to have been infected, but may be at risk of exposure to the influenza virus. As used herein, "limiting" means to limit influenza infection in subjects at risk of influenza infection. Given the nature of seasonal influenza outbreaks, virtually all subjects are at risk of exposure, at least at certain times of the year.

Groups at particularly high risk include children under age 18, adults over the age of 65, and individuals suffering from one or more of asthma, diabetes, heart disease, or any type of immunodeficiency.

As used herein, a "therapeutically effective amount" refers to an amount of the polypeptide that is effective for treating and/or limiting influenza infection. The polypeptides are typically formulated as a pharmaceutical composition, such as those disclosed above, and can be administered via any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques or intraperitoneally. Dosage regimens can be adjusted to provide the optimum desired response (e.g., a therapeutic or prophylactic response). A suitable dosage range may, for instance, be 0.1 ug/kg-100 mg/kg body weight; alternatively, it may be 0.5 ug/kg to 50 mg/kg; 1 ug/kg to 25 mg/kg, or 5 ug/kg to 10 mg/kg body weight. The polypeptides can be delivered in a single bolus, or may be administered more than once (e.g., 2, 3, 4, 5, or more times) as determined by an attending physician.

In certain embodiments, the polypeptides of the invention neutralize influenza virus infectivity. While not being limited by any mechanism of action, neutralizing activity may be achieved by preventing the influenza virus from interacting with its target cell. The polypeptides of the invention target an HA epitope that blocks the receptor binding site of HA. Since the HA protein conformational change leads to fusion of the viral and cell membrane, polypeptide binding to the HA protein in its pre-fusion form may prevent fusion. In various embodiments, the polypeptides of the invention prevent influenza virus from infecting host cells by at least 99%, at least 95%, at least 90%, at least 85%, at least 80%, at least 75%, at least 70%, at least 60%, at least 50%/0, at least 45%, at least 40%, at least 45%, at least 35%, at least 30%, at least 25%, at least 20%, or at least 10% relative to infection of host cells by influenza virus in the absence of the polypeptides. Neutralization can, for instance, be measured as described in "Laboratory techniques in influenza," edited by F.-X. Meslin, M. M. Kaplan and H. Koprowski (1996), 4th edition, Chapters 15-17, World Health Organization, Geneva.

The polypeptides according to the invention can bind to the HA protein with any suitable affinity constant ($K_d$ value) that provides therapeutic or prophylactic benefit. In various embodiments, the $K_d$ value is lower than $0.2*10^{-4}$ M, $1.0*10^{-5}$ M, $1.0*10^{-6}$ M, $1.0*10^{-7}$ M, $1.0*10^{-8}$ M, $1.0*10^{-9}$ M, $1.0*10^{-10}$ M, $1.0*10^{-11}$ M, or $1.0*10^{-12}$ M. Affinity constants can for instance be measured using surface plasmon resonance, i.e., an optical phenomenon that allows for the analysis of real-time biospecific interactions by detection of alterations in protein concentrations within a biosensor matrix, for example, using the BIACORE system (Pharmacia Biosensor AB, Uppsala, Sweden).

In another aspect, the present invention provides methods for diagnosing an influenza infection, or monitoring progression of an influenza infection, comprising (a) contacting a biological sample from a subject suspected of having an influenza infection with a diagnostically effective amount of one or more polypeptides of the invention under conditions suitable for binding of the polypeptide to a viral HA protein present in the sample, (b) removing unbound polypeptide and/or sample; and (c) detecting polypeptide-viral HA binding complexes, where the presence of such binding complexes indicates that the subject has an influenza infection, or provides a measure of progression of an influenza infection.

The methods of this aspect of the invention can be used to more accurately identify patients that may be suffering from an influenza infection and to thus provide more informed determination of treatment options by an attending caregiver. Individuals at risk of an influenza infection are as described above. The methods can also be used to monitor progression of an influenza infection; in this embodiment, the subject is known to be infected, and the methods can be used, for example, as a data point for an attending caregiver to determine whether to initiate, modify, or continue a particular course of therapy, such as treatment with neuraminidase or M2 protein inhibitors.

The biological sample may be any suitable biological sample including, but not limited to blood, serum, nasal secretions, tissue or other biological material from a subject at risk of infection.

The sample may first be manipulated to make it more suitable for the method of detection. "Manipulation" includes, but is not limited to treating the sample in such a way that any influenza virus in the sample will disintegrate into antigenic components such as proteins, polypeptides or other antigenic fragments. The polypeptides of the invention are contacted with the sample under conditions which allow the formation of a complex between the human polypeptides and influenza virus or antigenic components thereof that may be present in the sample. The formation of such complexes, if any, indicating the presence of influenza virus in the sample, is then detected and measured by suitable means. Such methods include, but are not limited to homogeneous and heterogeneous binding immunoassays, such as radioimmunoassays (RIA), ELISA, immunofluorescence, immunohistochemistry, FACS, BIACORE, biolayer interferometry and Western blot analyses. Suitable conditions to promote binding of the test compounds to one or more polypeptide of the invention can be determined by those of skill in the art, based on the teachings herein.

The polypeptides of the invention for use in this aspect may comprise a conjugate as disclosed above, to provide a tag useful for any detection technique suitable for a given assay. The tag used will depend on the specific detection/analysis/diagnosis techniques and/or methods used. The methods may be carried in solution, or the polypeptide(s) of the invention may be bound or attached to a carrier or substrate, e.g., microtiter plates (ex: for ELISA), membranes and beads, etc. Carriers or substrates may be made of glass, plastic (e.g., polystyrene), polysaccharides, nylon, nitrocellulose, or teflon, etc. The surface of such supports may be solid or porous and of any convenient shape.

In another aspect, the present invention provides methods for identifying candidate influenza vaccines, comprising (a) contacting test compounds with a polypeptide of the present invention under conditions suitable for polypeptide binding; and (b) identifying those test compounds that bind to the polypeptide of the invention, wherein such test compounds are candidate influenza vaccines.

As discussed above, the polypeptides of the present invention target an HA epitope that is absent in HA post-conformational change. Thus, the polypeptides of the invention can be viewed as specific binders to an HA epitope, similar to antibody binding to a specific epitope. Vaccines can be produced, for example, by selecting small molecules (ie: mimotopes) that bind to an antibody specific to a viral epitope. Thus, the present methods involve substituting one or more polypeptides of the present invention for the antibody in such assay to identify candidate influenza vaccines.

Suitable conditions to promote binding of the test compounds to one or more polypeptide of the invention can be determined by those of skill in the art, based on the teachings herein. The polypeptides of the invention for use in this aspect may comprise a conjugate as disclosed above, to provide a tag useful for any detection technique suitable for a given assay. The tag used will depend on the specific detection/analysis/diagnosis techniques and/or methods used, as discussed above. The methods may be carried in solution, or the polypeptide(s) of the invention may be bound or attached to a carrier or substrate, as discussed above. Based on the teachings herein, it is within the level of skill in the art to determine specific conditions for the various types of diagnostic assays disclosed in this aspect of the invention.

When the test compounds comprise polypeptide sequences, such polypeptides may be chemically synthesized or recombinantly expressed. Recombinant expression can be accomplished using standard methods in the art, as disclosed above. Such expression vectors can comprise bacterial or viral expression vectors, and such host cells can be prokaryotic or eukaryotic. Synthetic polypeptides, prepared using the well-known techniques of solid phase, liquid phase, or peptide condensation techniques, or any combination thereof, can include natural and unnatural amino acids. Amino acids used for peptide synthesis may be standard Boc (Na-amino protected Na-t-butyloxycarbonyl) amino acid resin with standard deprotecting, neutralization, coupling and wash protocols, or standard base-labile Na-amino protected 9-fluorenylmethoxycarbonyl (Fmoc) amino acids. Both Fmoc and Boc Na-amino protected amino acids can be obtained from Sigma, Cambridge Research Biochemical, or other chemical companies familiar to those skilled in the art. In addition, the polypeptides can be synthesized with other Na-protecting groups that are familiar to those skilled in this art. Solid phase peptide synthesis may be accomplished by techniques familiar to those in the art and provided, such as by using automated synthesizers.

When the test compounds comprise antibodies, such antibodies can be polyclonal or monoclonal. The antibodies can be humanized, fully human, or murine forms of the antibodies. Such antibodies can be made by well-known methods, such as described in Harlow and Lane, Antibodies; A Laboratory Manual, Cold Spring Harbor Laboratory, Cold Spring Harbor, N.Y., (1988).

When the test compounds comprise nucleic acid sequences, such nucleic acids may be produced by any suitable means, such as chemical synthesis. The nucleic acids may be DNA or RNA, and may be single stranded or double. Similarly, such nucleic acids can be chemically or enzymatically synthesized by manual or automated reactions, using standard techniques in the art. If synthesized chemically or by in vitro enzymatic synthesis, the nucleic acid may be purified prior to introduction into the cell. For example, the nucleic acids can be purified from a mixture by extraction with a solvent or resin, precipitation, electrophoresis, chromatography, or a combination thereof. Alternatively, the nucleic acids may be used with no or a minimum of purification to avoid losses due to sample processing.

When the test compounds comprise compounds other than polypeptides, antibodies, or nucleic acids, such compounds can be made by any of the variety of methods in the art for conducting organic chemical synthesis.

In another aspect, the present invention provides methods for identifying candidate compounds for treating, limiting, and/or diagnosing influenza infection, comprising (a) contacting an influenza HA protein with (i) test compounds and (ii) a polypeptide of the present invention, under conditions suitable for binding of the HA protein to the polypeptide of the present invention; and (b) identifying those test compounds that out compete the polypeptide for binding to the HA protein, wherein such test compounds are candidate compounds for treating, limiting, and/or diagnosing influenza infection.

In this aspect, the methods identify test compounds that compete with the polypeptides of the invention for binding to HA, and thus such candidate compounds may be useful in any of the other methods of the invention disclosed herein. Any suitable test compound can be used, as disclosed above in the aspect of the invention. In general, competitive inhibition is measured by means of an assay, wherein an HA composition is admixed with the polypeptide(s) of the invention and the test compounds to be screened. In one embodiment, the test compounds to be screened are present in excess. Protocols based upon ELISAs are suitable for use in such competition studies. In certain embodiments, one may pre-mix the polypeptide(s) of the invention with varying amounts of test compounds to be screened (e.g., 1:10, 1:20, 1:30, 1:40, 1:50, 1:60, 1:70, 1:80, 1:90 or 1:100) for a period of time prior to applying to the HA composition. In other embodiments, the polypeptide(s) of the invention and varying amounts of test compounds to be screened are admixed during exposure to the HA composition. Any suitable detection means can be used binding. In one embodiment, the polypeptide(s) of the invention are tagged for detection, as discussed above. In this embodiment, the detectable label will decrease in the presence of competitive test compounds. The reactivity of the (labeled) polypeptide of the invention in the absence of test compound could serve as one suitable control. Preferably, competitive test compounds will, when present in excess, inhibit specific binding of the polypeptide(s) of the invention to HA by at least 10%, preferably by at least 25%, more preferably by at least 50%, and most preferably by at least 75% to 90% or even greater.

All of these aspects/embodiments disclosed herein can be combined with any other aspect/embodiment, unless the context clearly dictates otherwise.

EXAMPLES

Computational Design of New Sialic-Acid Site Binders

A pre-selected list of 1718 high resolution monomeric crystal structures from the PDB, was searched for proteins that could harvest any fragments between Ser97 and Leu100K(Ala100I) of the heavy chain CDR3 of the c05 antibody(pdb 4fp8), resulting in grafted fragments of 6-15 residues. Variations of the loop were matched, allowing both endpoint matching as well as superposition. The shortest fragment contained only the tip of the hairpin and the few residues of the beta-strand-like conformation that hydrogen bond to Loop 130 of hemagglutinin (HA), which can be transplanted onto various beta-hairpin containing proteins. After integration of the matched segments, several rounds of RosettaDesign along with rigid-body minimization were performed while ensuring that the hydrogen bonds to Loop 130 and Tyr98 were maintained. The new interface between the scaffold protein and HA was re-designed using RosettaDesign while only keeping identities of the core beta turn region of the original loop fixed (amino acids: SAGW). Mutations in the designs were reverted to their original identity (the wildtype scaffold before design), if the reversion would not clash with the newly designed interface or would not harm the computed binding energy.

SB24 was based on the scaffold with the PDB I.D. 2qtd with the following sequence:
(SEQ ID NO: 130)
MINMKVAISMDVDKISNSFEDCKYFLIVRIDDNEVKSTKVIFNDESGKKS

IVKENVNAIICKNISEENYKKFSKKIEIYHAEGDDVDKNISLFIEGELSK

ISNP.

SB52 was based on the PDB entry 2w9q
(SEQ ID NO: 129)
GIVNVPNPNNTKFQELARFAIQDYNKKQNAHLEFVENLNVKEQVVAGIMY

YITLAATDDAGKKKIYKAKIWVKEWEDFKKVVEFKLV.

The sequence for SB24 was shortened in the progress of grafting, whereas no length changes were made to the SB52.

Design and Selection of Disulfide-Linked Circular Peptides Against the Sialic Acid Site To see whether a small disulfide-linked hairpin-like peptide would be able to mimic the sialic acid linked to galactose by α2,6-linkages (Siaα2,6Gal), which is displayed on the surface cells of the human respiratory tracts, we took the amino acids around the beta-turn of the CDR3 of the c05 antibody as a starting point. We replaced various positions to ensure stability of the small peptide as well as extra contacts. To ensure stability and folding of the peptide, we inserted two cysteine residues to allow the introduction of a disulfide bridge between the between the beta-strands of our model. The structure of the short peptide and its new disulfide bridge was designed using RosettaRemodel. Several variants were collected from the first library using yeast surface display.

Results

Designs Against the Sialic-Acid Binding Site

Designs were synthesized in bulk (Gen9 Inc.), and transformed as a pool together with a yeast surface display expression vector in to yeast cells. The pool of designs displayed on the surface of yeast was incubated with 1 µM H3 (A/Hong Kong/1/1968-H3N2) and yeast cells showing binding were selected. Indeed, several designs showed binding activity, however only if the graft contained the shortest fragment. Nine designs were identified that exhibited binding activity, three of these were sequence variations of the same scaffold and one bound non-specifically to other test proteins.

Sequences of experimentally identified computationally designed binders against HA are as follows:

SB24
(SEQ ID NO: 83)
GIGMVAISMDTDKISNSFEDCKYFLIVVVSAGWTNTIFNDESGKKEIVKM

NVDAIICKNISEENYKKFSKKIEIYHAEGDDVDKNISLFIEGELSKIS

NP;

SB52
(SEQ ID NO: 84)
GIVNVPNPNNTKFQQLARNAIANYNDNQNAHLEFVENLNVKEQVTGGIMY

YITLAATDDAGKKKIYKAKIAVVDSAGWEGVTEFKLV;

SB53
(SEQ ID NO: 85)
GIVNVPNPNNTKFQQLARNAIQNYNDNQNAHLEFVENLNVKEQVTGGIMY

YITLAATDDAGKKKIYKAKIAVVDSAGWEGITEFKLV;

SB55
(SEQ ID NO: 86)
GIVNVPNPNNTKFQQLARSAIQNYNDNQNAHLEFVENLNVKEQVTGGIMY

YITLAATDDAGKKKIYKAKIAVVDSAGWEGITEFKLV;

SB41
(SEQ ID NO: 87)
KEITNALETWGALGQDINLDIPSFQMSDDIADIKWEKTQDNKMIVVFSAG

WIAKDTYDLYENGTLKIAHLTTDDQAIYKVSITDTKGKNVLEKIFDLKIQ

ERVSKPKISWTCINTTLTCEVMNGTDPELNLYQDGKHLKLSQRVITHKWT

TSLSAKFKCTAGNKVSKESSVEPVSCPEK

SB60
(SEQ ID NO: 88)
KIIITGEPGVGKTTLVKKIVERLGKRAIGFWTEEVTDPETKKRTGFRIIT

TEGKKKVFSVVSAGWESKQNFEELAIPILERAYREAKKDRRKVIIIDEIG

DALGSSKFRDLVRQIHDPNVNVVATIPIRDDAPLIKEIRRLPGAVLIELT

PENRDVILEDILSLLER;
and

SB23
(SEQ ID NO: 89)
GHPTLKTPESVTGTWKGDVKIQCIYDPLRGYEQTEVKWLVRHGSDSVTIF

ERVSSAGWDGISQDKYNGRLQVSDSVPGDVSLQINTLQMDDRNHYTCEVT

WQTPDGNQVIRDKIIELRVRK.

Sequence Optimization of Two Selected Designs

Two designs (SB24 and SB52) were selected for further optimization. Their genes were subjected to random mutagenesis and better binding protein variants were selected through yeast surface display selection against H3 (A/Hong Kong/1/1968-H3N2) and H2 (A/Adachi/2/1957-H2N2). The epitope was confirmed through competition with the S139/1 antibody for binding to H3; S139/1 binds to the sialic acid binding site as crystallographic analysis have confirmed. The fact that the designs could not bind when the S139/1 antibody was bound to hemagglutinin strongly suggests that the designs indeed bind to the site they were designed for. Preliminary electron microscopy confirmed this data as well.

Optimization of Binding Through Random Mutagenesis and Selections

A) SB24: Individual mutations in the SB24 amino acid sequence identified after 3 rounds of selections against HA subtype H3 were I2T, V27M, V28L or V28M, V29E, and K49E.

Exemplary full length mutants are as follows:
H3 24-3 containing following mutations:
    Variant H3 24-2 (V27M, F38S, K49E)

Variant H3 24-2 (V27M, F38S, K49E)
                                           (SEQ ID NO: 90)
GIGMVAISMDTDKISNSFEDCKYFLIMWSAGWTNTISNDESGKKEIVEMN

VDAIICKNISEENYKKFSKKIEIYHAEGDDVDKNISLFIEGELSKISNP

Variant H3 24-3a (I2T, V29E)
                                           (SEQ ID NO: 91)
GTGMVAISMDTDKISNSFEDCKYFLIVVESAGWTNTIFNDESGKKEIVKM

NVDAIICKNISEENYKKFSKKIEIYHAEGDDVDKNISLFIEGELSKISNP

Variant H3 24-3b (V28M)
                                           (SEQ ID NO: 92)
GTGMVAISMDTDKISNSFEDCKYFLIVMVSAGWTNTIFNDESGKKEIVKM

NVDAIICKNISEENYKKFSKKIEIYHAEGDDVDKNISLFIEGELSKISNP

LE

Variant H3 24-8 (V27M, K49E)
                                           (SEQ ID NO: 93)
GTGMVAISMDTDKISNSFEDCKYFLIMVVSAGWTNTIFNDESGKKEIVEM

NVDAIICKNISEENYKKFSKKIEIYHAEGDDVDKNISLFIEGELSKISNP

LE

The binding behavior of these mutants, as determined using yeast surface titration, is provided in FIG. 1. It has been demonstrated before that binding to the head region, in particular to the sialic acid site, is highly effective for the neutralization of the virus with an effective concentration for neutralization (EC50) close to the binding constant. Therefore, the SB24 variants provide great material for a potential therapeutics against Influenza viruses against various Influenza strains, as binding is relatively strong.

As the originally computational designs were designed to bind to H3, it was not surprising that they did not bind to the H1 nor H2 subtypes by using yeast surface display. To identify positions that were suboptimal, as well as positions that would allow binding to other subtypes, we generated a simple mutagenesis library of SB24. Screening of the library for binding to H3 and H2 allowed the identification of substitutions for SB24 to bind tighter to H3. No substitutions were found to enable binding of SB24 to H2, nor binding to H1 by either design library. We reasoned that binding to the other subtypes could require more than one or two substitutions. Through next-generation sequencing, we obtained sequences for the naïve population as well as the population after selection 1 and 2 for binding to H3 and mapped out optimality of each position.

The results of these studies confirmed that the interface between the SB24 mutant polypeptides and the HA protein are around residues 1-3, 25-38, 45-51, and position 83. Heat maps (not shown) were generated showing how optimal or variable an amino acid at a given position at the interface residues of the SB24 mutants is in the context of binding against subtype H3 by determining the frequency of an amino acid change in naïve as well as sorted pool, followed by calculating the ratio of selected versus naïve frequencies of a given amino acid change of a given position.

Positions that had an effect on binding above average based on the first optimization step and extracted from the heat map were interface positions 1, 2, 26-29, 38, 45, 49, 51. We additionally identified some small effect on binding through the positions 71-73 and 90-93, which are part of the variability regions, and changes within these positions likely contribute indirectly to binding, e.g. by stabilizing the protein. Changes and positions identified were included into the next generation sequence diversity discussed below and summarized together with additional changes for the next generation of optimized binders in Table 4.

B) SB52: Individual beneficial mutations in the SB52 amino acid sequence identified after 3 rounds of selections against HA subtype H3 were N19S or N19Y, L38M, and G47D.

Exemplary full length mutants were as follows:

Variant SB52-3 (G47D, N27Y)
                                           (SEQ ID NO: 94)
GIVNVPNPNNTKFQQLARNAIANYNDYQNAHLEFVENLNVKEQVTGDIMY

YITLAATDDAGKKKIYKAKIAVVDSAGWEGVTEFKLV

52-N19S
                                           (SEQ ID NO: 121)
GIVNVPNPNNTKFQQLARSAIANYNDYQNAHLEFVENLNVKEQVTGDIMY

YITLAATDDAGKKKIYKAKIAVVDSAGWEGVTEFKLV

52-N19Y
                                           (SEQ ID NO: 122)
GIVNVPNPNNTKFQQLARYAIANYNDYQNAHLEFVENLNVKEQVTGDIMY

YITLAATDDAGKKKIYKAKIAVVDSAGWEGVTEFKLV

52-L38M
                                           (SEQ ID NO: 123)
GIVNVPNPNNTKFQQLARNAIANYNDYQNAHLEFVENMNVKEQVTGDIMY

YITLAATDDAGKKKIYKAKIAVVDSAGWEGVTEFKLV

52-G47D
                                           (SEQ ID NO: 124)
GIVNVPNPNNTKFQQLARNAIANYNDYQNAHLEFVENLNVKEQVTDDIMY

YITLAATDDAGKKKIYKAKIAVVDSAGWEGVTEFKLV

Variant SB52-3 (G47D, N27Y)
                                           (SEQ ID NO: 94)
GIVNVPNPNNTKFQQLARNAIANYNDYQNAHLEFVENLNVKEQVTGDIMY

YITLAATDDAGKKKIYKAKIAVVDSAGWEGVTEFKLV

Figure 2A:
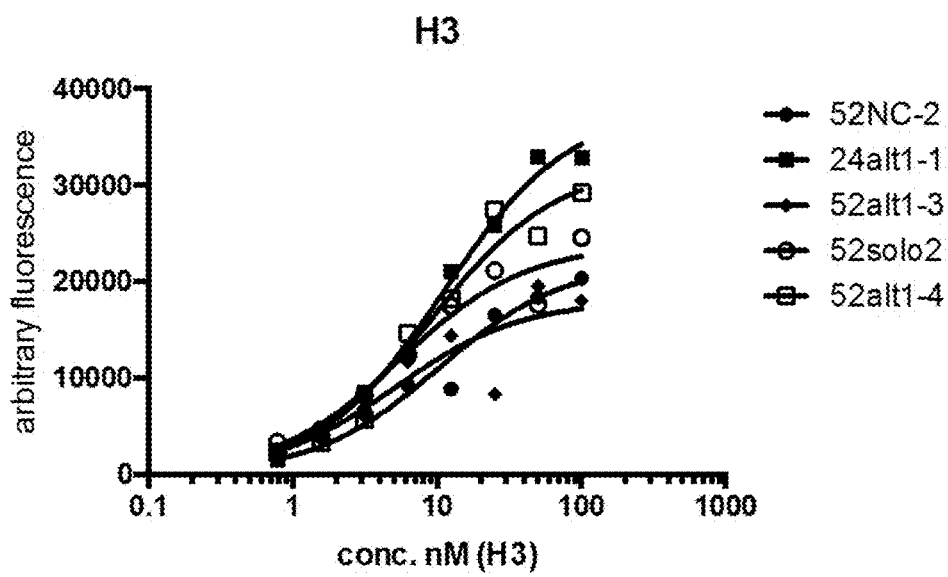
FIG. 2A-C. Binding behaviors of exemplary SB24 and SB52 mutants to exemplary (A) H1, (B) H2, and (C) H3 strains as indicated by using yeast surface display and indicated hemagglutinin subtypes. Variants were isolated from the second-generation library that is summarized in table 1 and 4. The variant 52NC- TABLE 1-continued SB52 genus (SEQ ID NO: 1)
Figure 2:
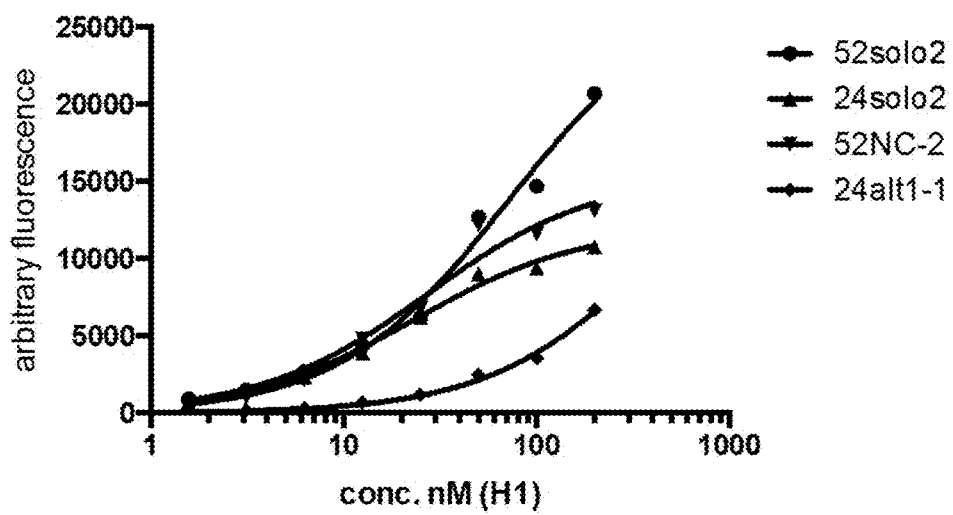
Figure 2C:
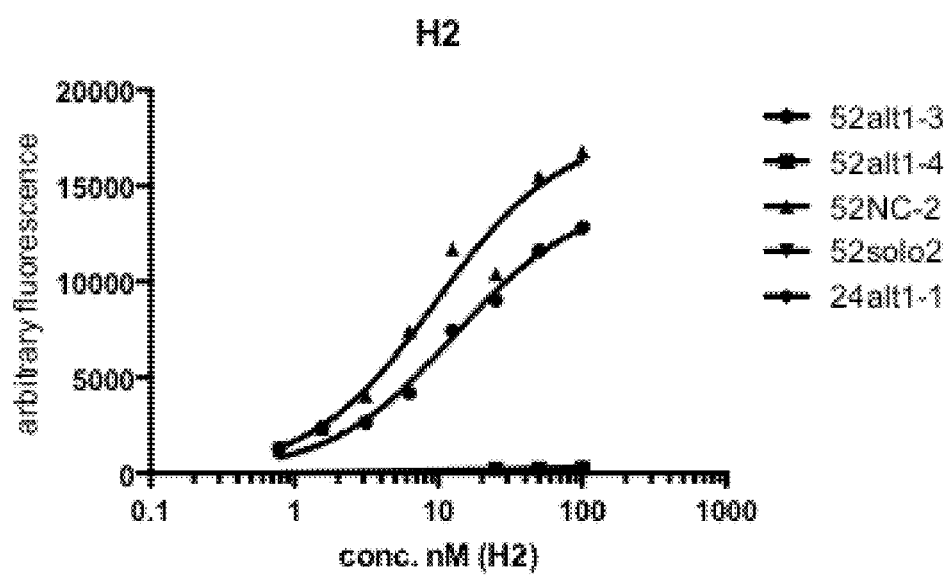

Binding behavior of exemplary SB52 mutants, as determined using yeast surface titration, is provided in FIG. 2. For example, variant 52NC-2 shows binding to all three subtypes H1, H2 and H3, which is ideal for the making of a potential new therapeutic.

Variants of SB52 for Binding to H2

Influenza A can be phylogenetically described as two major groups. As the previous designs were made against H3, binders against the H2 subtypes are desirable. We were able to identify SB52 mutations that allow cross-specific binding between the group I subtype H2 and the group II subtype H3. Identified beneficial mutations were N7K, N19Y, E79V, and I21V based on a simple random mutagenesis library.

Exemplary full length mutants were as follows:

Variant H2 SB52-4 (N19Y, E79V)
                                           (SEQ ID NO: 13)
GIVNVPN(P/C)NNTKFQQLARYAIANYNDNQNAHLEFVENLN(V/C)KE

QVTGGIMYYITLAATDDAGKKKIYKAKIAVVDSAGWVGVTEFKLV

```
Variant H2 SB52-13 (N7K, N19Y, E79V)
                                              (SEQ ID NO: 14)
GIVNVPK(P/C)NNTKFQQLARYAIANYNDNQNAHLEFVENLN(V/C)KE

QVTGGIMYYITLAATDDAGKKKIYKAKIAVVDSAGWVGVTEFKLV
```

Figure 3:
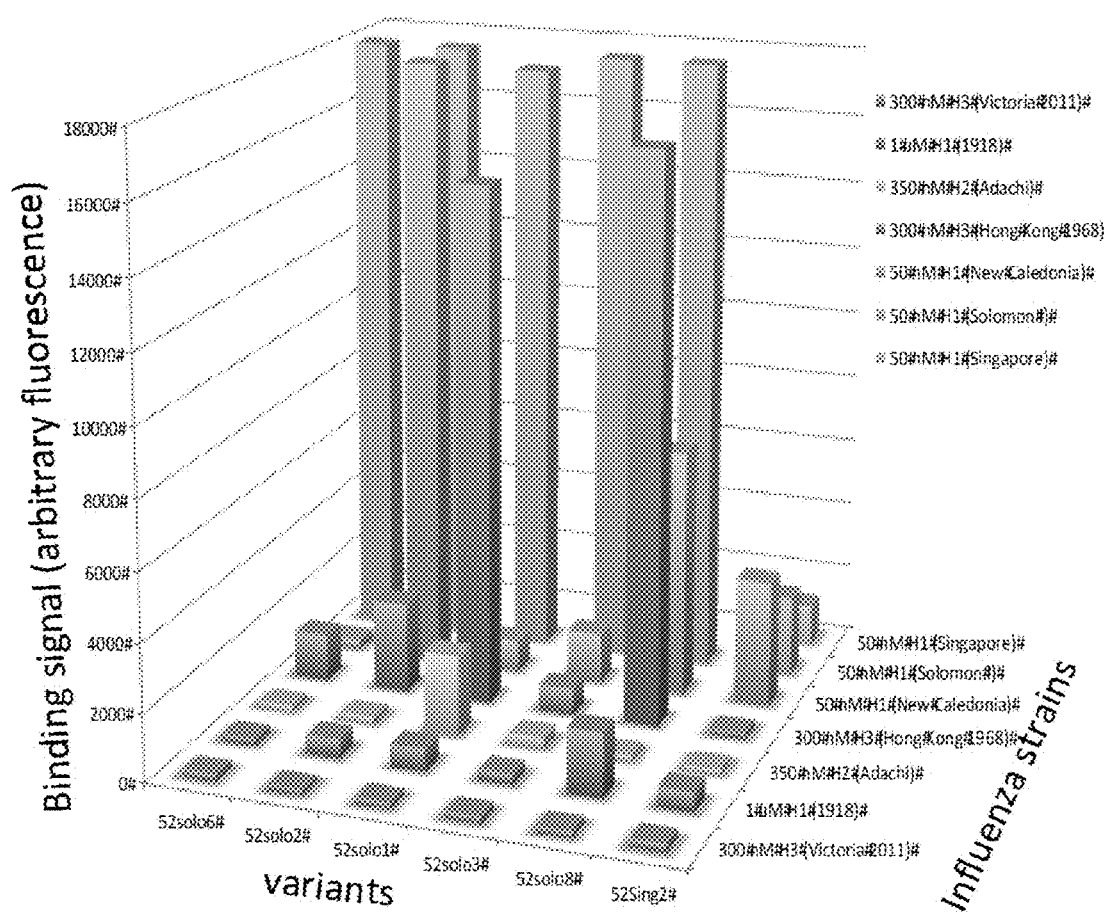

Binding behavior of exemplary SB52 mutants, as determined using yeast surface titration, is provided in FIG. 3. Different binding signals for diverse variants and hemagglutinin versions demonstrates the variants potential to serve as diagnostics, as it can discriminate strains or subtypes. This can be tremendously useful in clinical settings to identify which Influenza strain or subtype has infected a patient. Having a diverse set of variants with different specificity could allow providing a panel of these variants on a detection device to identify clearly which strain is dealt with.

As the originally computational designs were designed to bind to H3, it was not surprising that they did not bind to the H1 nor H2 subtypes by using yeast surface display. To identify positions that were suboptimal, as well as positions that would allow binding to other subtypes, we generated a simple mutagenesis library of SB52. Screening of the library for binding to H3 and H2 allowed the identification of substitutions for SB52 to bind tighter to H3, as well as substitutions in SB52 that allow binding to H2. No substitutions were found to enable binding of to H1. We reasoned that binding to the other subtypes could require more than one or two substitutions. For example, for SB52, at least two substitutions were necessary to obtain binding to H2. Through next-generation sequencing, we obtained sequences for the naïve population as well as the population after selection 1 and 2 for binding to H3 and mapped out optimality of each position.

The results of these studies indicate that the interface between the SB52 mutant polypeptides and the HA protein are at around residues 18-27, 44-48, and 70-82.

SB52 Against H3

Heat maps (not shown) were generated showing how optimal or variable an amino acid at a given position at the interface residues of the SB52 mutants is in the context of binding against subtype H3 by determining the frequency of an amino acid change in naïve as well as sorted pool, followed by calculating the ratio of selected versus naïve frequencies of a given amino acid change of a given position.

Positions that had an effect on binding above average based on the first optimization step and extracted from the heat map were interface positions: 19, 23, 26, 27, 45-48, 71, 74, 79, 80 and 82. We additionally identified some small effect on binding through the positions 11, 13, 51, 59, 64, 67-69 and 86 which are part of the variability regions, and changes within these positions likely contribute indirectly to binding, e.g. by stabilizing the protein.

Optimization of Binding Through Combinatorial Libraries and Selections

Hemagglutinin is subject to constant genetic changes. This is particularly manifested in the head region of hemagglutinin, as most antibodies bind to this exposed area: whenever a mutation of HA occurs, which prevents binding of any existing antibodies in an infected individual, the virus can propagate efficiently. Hence, the head region is under constant selective pressure to evade the immune response, so changes within the head region area tend to be improve the survival of the virus and a new seasonal virus can evolve. For designing protein binders and inhibitors against the head region of HA that partially overlap with areas that are subject to change, it is important to provide enough diversity to the inhibitor library to accommodate those changes. The core part of the binder/inhibitor (SB52 and SB24) binds to the sialic acid binding site which cannot mutate, otherwise the virus would not be able to infect cells. However, changes at the periphery may occur and the aim of the generation of further libraries was to introduce diversity within the sequence of the binders that would accommodate those changes. The constant genetic drift of HA introduces charge inversions, protrusions, insertions and deletions within the periphery of the sialic acid binding site of HA itself. Hence, for positions of SB24 that are close to areas of high sequence variations of HA, corresponding diversity is needed in the inhibitor to avoid charge repulsions or clashes. As we had a model of the interactions between SB24 and HA, the sequence variation became a spatially defined problem for which we could rationally decide on the diversity needed to compensate for the genetic drift of the Influenza virus, at least for its surface protein HA. For instance, if HA would introduce a negatively charged residue, the binder cannot have a negatively charge residue right next to it as they would repel each other and weaken binding significantly. For the design of the generation II library, sequence changes of HA from different subtypes and strains were considered in the context of the three-dimensional model bound to the head region of HA. Thereby, corresponding sequence changes necessary to accommodate the diversity of HA were allowed. The overall idea is that if a single universal design against the head region is not possible, we will have a small library of variants from which the appropriate one for a given strain can be quickly pulled out of.

Next to mutations that would allow binding to other subtypes, a several beneficial mutations that were identified through previous selection and deep sequencing were incorporated into the generation II library.

(A) SB24 Variants

Variants below were isolated after selections against either H1 or H2 subtypes (exemplified by A/Hong Kong/1/1968, H1N1 A/Solomon Islands/3/2006 (H1 SI), H2N2 A/Adachi/2/1957 (H2 Adachi) or A/New Caledonia/20/1999) or as a combination of these.

```
SB24solo2
                                              (SEQ ID NO: 45)
ASGMLAISMDTDKISNSFEDCKYFLIELKSAGWTNTIFNDESGKEEIVKM

GVDAIICKNISEENYKKESKKIEIYHAEGDDVNKNISLFLEGELSKISNP

SB24solo6
                                              (SEQ ID NO: 46)
ASGMLAISMDTDKISNSFEDCKYFQLELPSAGWTNTIFNDESGKEEIVKM

NVDAIICKNISEENYKKFSKKIEIYHAEGDDVKKNISLFLEGELSKIS

NP;

SB24NC1
                                              (SEQ ID NO: 47)
ASGMLAISMDTDKISNSFEDCKYFQIELPSAGGTNTIFNDESGKEETVKM

GVDAIICKNISEENYKKFSKKIEIYHAEGDDVKKNISLFIEGELSKIS

NP;

SB24alt1-1
                                             (SEQ ID NO: 125)
ASGMLAISMDTDKISNSFEDCKYFQLYVLSAGWTNTIFNDESGKEEIVKM

SVDAIICKNISEENYKKFSKKIEIYHAEGDDVDKNISLFLEGELSKIS

NP;
```

SB24SingNC1
(SEQ ID NO: 127)
ASGMLAISMDTDKISNSFEDCKYFQIELPSAGWTNTIFNDESGKEEIVKM

GVDAIICKNISEENYKKFSKKIEIYHAEGDDVEKNISLFLEGELSKIS

NP;
and

SB24SingNC3
(SEQ ID NO: 128)
ASGMLAISMDTDKISNSFEDCKYFQLVLASAGWTNTIFNDESGKEEIVKM

GVDAIICKNISEENYKKFSKKIEIYHAEGDDVDKNISLFAEGELSKIS

NP.

Figure 4:
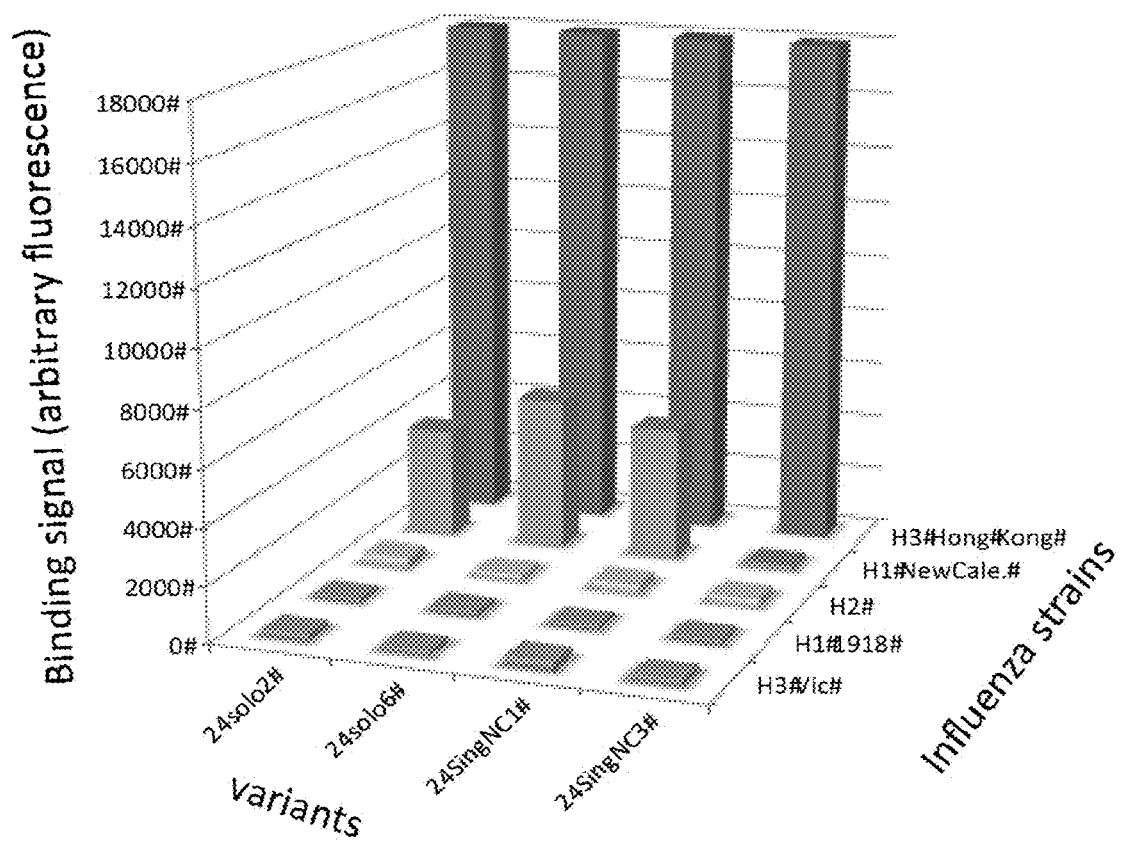

FIG. 4 shows binding data for these mutants using yeast surface display.

(B) SB52 Variants

The following sequence diversity was used for the SB52 library generation, based on the previous studies:

Library Composition:
Position 10: T only
Position 13: Y or F (wt)
Position 18: N, Y, T, S
Position 21: V or I
Position 26: N, H and Y
Position 27: N, H and Y
Position 44: L, T, V, A, S, I
Position 45: A, G, S, N, T, Y
Position 46 and 47 are set so that one of them is glycine and the other is any of the following 17 amino acids; N, H, D, S, K, Y, H, A, V, T, I, Q, D, E, M, L, F
Position 48: N, G, T, I, A, S, D, V
Position 70: V, I
Position 71: G, A
Position 74: E
Position 79: K, I, A, T, V, E
Position 80: V, A, G
Position 82: T, K, R, D, E, A, S, N SB52 variants below were isolated after selections against H1, H2, or H3 subtypes (exemplified by either H3 A/Hong Kong/1/1968, H3 A/Victoria/361/2011 (H3 Victoria), H1 A/Solomon Islands/3/2006 (H1 SI), H1 A/South Carolina/1/1918 (H1 1918), H1 A/California/04/2009 (Cal 09), H1N1 A/Singapore/6/1986 (H1 Singapore) H1 A/New Caledonia/20/1999 or H2 A/Adachi/2/1957 (H2 Adachi):

52solo1

(SEQ ID NO: 15)

GIVNVPN(P/C)NTTKYQQLARSAIAIYNYHQNAHLEFVENLN(V/C)KE

QVGGMNMYYITLAATDDAGKKKIYKAKVGVVESAGWKGVEEFKLV;

52solo2

(SEQ ID NO: 16)

GIVNVPN(P/C)NTTKYQQLARSAIAVYNYHQNAHLEFVENLN(V/C)KE

QIAGKTMYY-ITLAATDDAGKKKIYKAKVGVVESAGWEGVEEFKLV;

52solo3

(SEQ ID NO: 17)

GIVNVPN(P/C)NTTKYQQLARIAIAVYNNYQNAHLEFVENLN(V/C)KE

QSGGKVMYYITLAATDDAGKKKIYKAKVGVVESAGWIGVEEFKLV;

-continued

52solo8

(SEQ ID NO: 18)

GIVNVPN(P/C)NTTKYQQLARSAIAVYNNHQNAHLEFVENLN(V/C)KE

QAGGKAMYYITLAATDDAGKKKIYKAKIGVVESAGWEGVEEFKLV;

52sing2

(SEQ ID NO: 19)

GIVNVPN(P/C)NTTKYQQLARRAIAIYNNNQNAHLEFVENLN(V/C)KE

QTGLGIMYYITLAATDDAGKKKIYKAKIAVVESAGWVAVSEFKLV;

52solo8a (SEQ ID NO: 20)

GIVNVPN(P/C)NTTKYQQLARSAIAVYNNHQNAHLEFVENLN(V/C)KE

QAGGKAMYYITLAATDDAGKKKIYKAKIGVVESAGWEGVEEFKLV;

52solo8b (SEQ ID NO: 21)

GIVNVPN(P/C)NTTKYQQLARSAIAVYNYHQNAHLEFVENLN(V/C)KE

QIAGKTMYYITLAATDDAGKKKIYKAKVGVVESAGWEGVEEFKLV;

S2soloc (SEQ ID NO: 22)

GIVNVPN(P/C)NTTKYQQLARSAIAVYNNHQNAHLEFVENLN(V/C)KE

QAGGKAMYYITLAATDDAGKKKIYKAKIGVVESAGWEGVEEFKLV;

52sing2

(SEQ ID NO: 23)

GIVNVPN(P/C)NTTKYQQLARRAIAIYNNNQNAHLEFVENLN(V/C)KE

QTGLGIMYYITLAATDDAGKKKIYKAKIAVVESAGWVAVSEFKLV;

52sing2W (SEQ ID NO: 24)

GIVNVPN(P/C)NTTKYQQLARRAIAIYNNNQNAHLEFVENLN(V/C)KE

QWGLGIMYYITLAATDDAGKKKIYKAKIAVVESAGWVAVSEFKLV;

52sing2D (SEQ ID NO: 25)

GIVNYPN(P/C)NTTKYQQLARRAIAIYNNNQNAHLEFVENLN(V/C)KD

QTGLGIMYYITLAATDDAGKKKIYKAKIAVVESAGWVAVSEFKLV;

52alt1-3

(SEQ ID NO: 26)

GIVNVPN(P/C)NTTKYQQLARSAIAIYNNHQNAHLEFVENLN(V/C)KE

QVSYGAMYYITLAATDDAGKKKIYKAKVGVVESAGWVGVEEFKLV;

52alt1-4

(SEQ ID NO: 27)

GIVNVPN(P/C)NTTKYQQLARSAIAVYNYHQNAHLEFVENLN(V/C)KE

QIDYGAMYYITLAATDDAGKKKIYKAKIGVVESAGWIGVEEFKLV;

52del1

(SEQ ID NO: 31)

GIVNVPN(P/C)NTTKYQQLARRAIAVYNYYQNAHLEFVENLN(V/C)KE

QSSGLDMYYITLAATDDAGKKKIYKAKIAVESAGWIVVTEFKLV;

52del4

(SEQ ID NO: 32)

GIVNVPN(P/C)NTTKYQQLARRAIAVYNYYQNAHLEFVENLN(V/C)KE

QLTGHGMYYITLAATDDAGKKKIYKAKVAVESAGWIVVTEFKLV;

52del2

(SEQ ID NO: 33)

GIVNVPN(P/C)NTTKYQQLARRAIAVYNYYQNAHLEFVENLN(V/C)KE

QAGGQVMYYITLAATDDAGKKKIYKAKVAVESAGWIVVTEFKLV;

52del3
(SEQ ID NO: 34)
GIVNVPN(P/C)NTTKYQQLARRAIAVYNYYQNAHLEFVENLN(V/C)KE

QAAGEIMYYITLAATDDAGKKKIYKAKIAVESAGWIVVREFKLV;

52del5
(SEQ ID NO: 35)
GIVNYPN(P/C)NTTKYQQLARRAIAVYNYYQNAHLEFVENLN(V/C)KE

QAAGEIMYYITLAATDDAGKKKIYKAKIAVESAGWIVVREFKLV;

52del6
(SEQ ID NO: 36)
GIVNVPN(P/C)NTTKYQQLARIAIAIYNYHQNAHLEFVENLN(V/C)KE

QSGHGTMYYITLAATDDAGKKKIYKAKVGVVESAGWIGVTEFKLV;

52del7
(SEQ ID NO: 37)
GIVNVPN(P/C)NTTKYQQLARIAIAVYNHHQNAHLEFVENLN(V/C)KE

QISVGTMYYITLAATDDAGKKKIYKAKVGVVESAGWIEVEEFKLV;

52del8
(SEQ ID NO: 38)
GIVNVPN(P/C)NTTKYQQLARRAIAVYNYYQNAHLEFVENLN(V/C)KE

QLTLGVMYYITLAATDDAGKKKIYKAKVAV-ESAGWIVVTEFKLV;

52del9
(SEQ ID NO: 39)
GIVNVPN(P/C)NTTKYQQLARRAIAVYNYYQNAHLEFVENLN(V/C)KE

QSSSGNMYYITLAATDDAGKKKIYKAKIAV-ESAGWIVVKEFKLV;

52vic5-2
(SEQ ID NO: 28)
GIVNVPN(P/C)NTTKYQQLARRAIAIYNNNQNAHLEFVENLN(V/C)KE

QWGLGIMYYITLAATDDAGKKKIYKAKIAVVESAGWVAVSEFKLV;

52vic5-3
(SEQ ID NO: 29)
GIVNVPN(P/C)NTTKYQQLARSAIAIYNNNQNAHLEFVENLN(V/C)KE

QLNGYDMYYITLAATDDAGKKKIYKAKIGVVESAGWTGVNEFKLV;

52vic5-4
(SEQ ID NO: 30)
GIVNVPN(P/C)NTTKYQQLARSAIAIYNHYQNAHLEFVENLN(V/C)KE

QITGYDMYYITLAATDDAGKKKIYKAKVAVVESAGWEVVAEFKLV;

52NC-1
(SEQ ID NO: 95)
GIVNVPN(P/C)NTTKYQQLARIAIAVYNHHQNAHLEFVENLN(V/C)KE

QLGEGDMYYITLAATDDAGKKKIYKAKVGVVESAGWTGVEEFKLV;

52NC-2
(SEQ ID NO: 96)
GIVNVPN(P/C)NTTKYQQLARSAIAIYNYHQNAHLEFVENLN(V/C)KE

QLGEGDMYYITLAATDDAGKKKIYKAKIGVVESAGWTGVEEFKLV;

52NC-8
(SEQ ID NO: 97)
GIVNVPN(P/C)NTTKYQQLARSAIAIYNYHQNAHLEFVENLN(V/C)KE

QIGEGSMYYITLAATDDAGKKKIYKAKVGVVESAGWEGVEEFKLV;
and

52solo6
(SEQ ID NO: 126)
GIVNVPN(P/C)NTTKYQQLARRAIAIYNHNQNAHLEFVENLN(V/C)KE

QIDYGSMYYITLAATDDAGKKKIYKAKVGVVESSGWTGVEEFKLV.

Table 11 shows binding data for exemplary mutants using yeast surface display, and demonstrate that several variants were identified that can either have strong binding to H1 and H3, or H5 subtypes or even all three H1, H2 and H3 as 52NC-2. * refers to any 52del variants listed in the document. As blocking the receptor binding site of Influenza also inhibits the virus, these variants present a new material for therapeutic avenues. As FIGS. 3 and 4 (barcharts) demonstrate, specific binders can also be quickly identified based on these polypeptide sequences, and we present several of these here. This high specificity will be tremendously useful for the manufacture of the next-generation flu diagnostics. The high specificity of the individual variants based on SB52 and SB24 can provide a set of variants that will allow paneling of the different Influenza strains.

Figure 5:
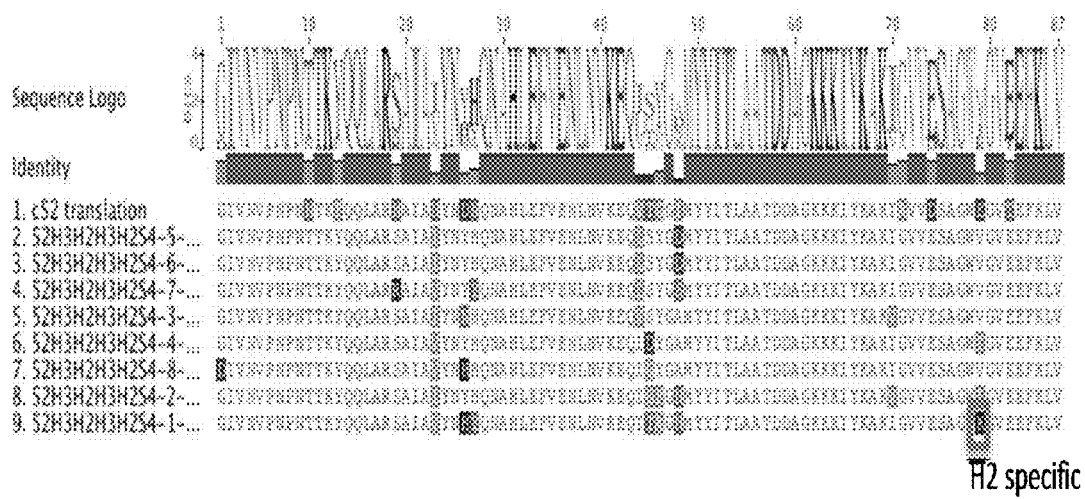

FIG. 5 shows an amino acid sequence alignment of variants isolated after selections against H3 and H2 strains.
Sequence Variations and Binding Data

TABLE 11

Determination of affinity constants via yeast surface display.
Concentration displayed in nM.

|  | 52alt1-3 | 52solo2 | 52solo1 | 52Sing2 | 52NC-2 | 24alt1-1 | 24solo2 | 52del* |
|---|---|---|---|---|---|---|---|---|
| H1 (A/SolomonIslands/3/2006) | − | 1.7 | 1.8 | 17.2 | 4.4 |  |  | nd |
| H1 (A/NewCaledonia/20/1999) | − | 9.1 | 20.7 | 44.9 | 27.2 | 436 | 23.2 | nd |
| H1 (A/Singapore/6/1986) | nd | nd | nd | ++ | nd |  |  | nd |
| H1 (A/South Carolina/1/1918) | − | + | + | + |  |  |  | nd |
| H2 (A/Adachi/2/1957) | 8.5 | − | >350 | − | 9.6 | − | − | nd |
| H3 (A/Hong Kong/1/1968) | 3 | 1 | 35.65 | − | 3.9 | 3.7 | +++ | nd |
| H1(California/2009) | (+) | − | − | + | − | − | − | nd |
| H5 A/Vietnam/1203/2004 | − | − | − | − |  |  |  | ++ |

Generation of Disulfide-Linked Peptides

HA mediates the attachment to the host-cells. As this function is so central to viral propagation, its sequence can vary only to the extent that it does not disrupt the functions of HA. Thus, this functional site presents an Achilles' heel for targeted protein therapeutics. Despite the strong evolutionary constraints which maintain binding of HA to its substrate (sialic acid on the surface of the host cells), substantial sequence changes occur in the immediate proximity of this binding site, and only very few residues are conserved, providing few constant contacts to bind to. For this reason it is can be difficult to obtain a high affinity inhibitor without compromising the breadth of binding to various HA subtypes. After all, the antigenic drift is part of its protecting mechanism against the host adaptive immune response. Also binding of HA to its receptor sialic acid itself is very weak (low mM). Hence, the smaller a binding protein is, the higher the chance that it would not interfere with any residues that are subject to constant changes and would thereby escape by blocking binding with the introduction of an incompatible residue at the interface.

For the rational design of peptides binding to the sialic acid site of hemagglutinin, the polypeptide can assume a hairpin-like structure that should be stabilized through a disulfide bridge at the hairpin ends. Thus we introduced pairing cysteine residues at a non-hydrogen bonding beta strand pair, which were positions at positions 3 and 14. Peptides contain HM (N-terminal) and LE (C-terminal) as part of the cloning sites and was tested a fusion C-terminal of the Aga2 protein (yeast surface anchor) and N-terminal of the c-Myc tag.

The library was screened for the best variants. Exemplary peptides include (where "X: is any amino acid):

```
                            (SEQ ID NO: 48)
GXCIGYPSAGWEXCW;

(SEQ ID NO: 49)
GGCIGVPSAGWEWCP;

(SEQ ID NO: 50)
GGCLGVPSAGWEICW;

(SEQ ID NO: 51)
GWCIGVPSAGWEICW;

(SEQ ID NO: 52)
GRCIGVPSAGWEVCW;

(SEQ ID NO: 53)
GHCMGVASAGWEICW;

(SEQ ID NO: 54)
GDCIGVASAGWEWCP;

(SEQ ID NO: 55)
GGCIGVPSAGWEWCP;

(SEQ ID NO: 56)
GGCLGVPSAGWEWCP;

(SEQ ID NO: 57)
GWCIGVPSAGWEICW;

(SEQ ID NO: 58)
GWCIGVPSAGWEICW;

(SEQ ID NO: 59)
GRCIGVPSAGWEVCW;

(SEQ ID NO: 60)
GHCMGVASAGWEICW;

(SEQ ID NO: 61)
GDCIGVASAGWEWCP;

(SEQ ID NO: 65)
GSCYRVVSAGWETC;

(SEQ ID NO: 65)
GSCYRVVSAGWETC;

(SEQ ID NO: 67)
GGCARVASAGWEICN;

(SEQ ID NO: 68)
GKCRWVASAGWEVCA;

(SEQ ID NO: 69)
GNCFAVVSAGWEKCK;

(SEQ ID NO: 70)
GMCTHVLSAGWEPCL;

(SEQ ID NO: 71)
GMCTHVLSAGWEPCL;

(SEQ ID NO: 72)
GCCGYVISAGWEMCS;

(SEQ ID NO: 73)
GDCTCMISAGWEPCE;

(SEQ ID NO: 74)
GFCCLVTSAGWEECY;

(SEQ ID NO: 75)
GFCCLVTSAGWEECY;
and (SEQ ID NO: 76)
GSCPFVTSAGWEKCL.;

(SEQ ID NO: 66)
GDCIVVASAGWEACR
```

---

SEQUENCE LISTING

<160> NUMBER OF SEQ ID NOS: 134

<210> SEQ ID NO 1
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is G or D

```
<220> FEATURE:
<221> NAME/KEY: MISC_FEATURE
<222> LOCATION: (7)..(7)
<223> OTHER INFORMATION: Xaa is N or K
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (9)..(9)
<223> OTHER INFORMATION: Xaa is N or K
<220> FEATURE:
<221> NAME/KEY: MISC_FEATURE
<222> LOCATION: (10)..(10)
<223> OTHER INFORMATION: Xaa is N or T
<220> FEATURE:
<221> NAME/KEY: MISC_FEATURE
<222> LOCATION: (13)..(13)
<223> OTHER INFORMATION: Xaa is F or Y
<220> FEATURE:
<221> NAME/KEY: MISC_FEATURE
<222> LOCATION: (18)..(18)
<223> OTHER INFORMATION: Xaa is R, N, Y, T, or S
<220> FEATURE:
<221> NAME/KEY: MISC_FEATURE
<222> LOCATION: (19)..(19)
<223> OTHER INFORMATION: Xaa is R, N, Y,  or S
<220> FEATURE:
<221> NAME/KEY: MISC_FEATURE
<222> LOCATION: (21)..(21)
<223> OTHER INFORMATION: Xaa is I or V
<220> FEATURE:
<221> NAME/KEY: MISC_FEATURE
<222> LOCATION: (23)..(23)
<223> OTHER INFORMATION: Xaa is N, I or V
<220> FEATURE:
<221> NAME/KEY: MISC_FEATURE
<222> LOCATION: (26)..(26)
<223> OTHER INFORMATION: Xaa is D, Y, N or H
<220> FEATURE:
<221> NAME/KEY: MISC_FEATURE
<222> LOCATION: (27)..(27)
<223> OTHER INFORMATION: Xaa is Q, Y, N or H
<220> FEATURE:
<221> NAME/KEY: MISC_FEATURE
<222> LOCATION: (38)..(38)
<223> OTHER INFORMATION: Xaa is L or M
<220> FEATURE:
<221> NAME/KEY: MISC_FEATURE
<222> LOCATION: (40)..(40)
<223> OTHER INFORMATION: Xaa is V or C
<220> FEATURE:
<221> NAME/KEY: MISC_FEATURE
<222> LOCATION: (42)..(42)
<223> OTHER INFORMATION: Xaa is E or D
<220> FEATURE:
<221> NAME/KEY: MISC_FEATURE
<222> LOCATION: (44)..(45)
<223> OTHER INFORMATION: Xaa is any amino acid
<220> FEATURE:
<221> NAME/KEY: MISC_FEATURE
<222> LOCATION: (46)..(46)
<223> OTHER INFORMATION: Xaa is G (Position 46 and 47 are set so that
      one of them is glycine and the other is any of the following 17
      amino acids; N,H,D,S,K,Y,H,A,V,T,I,Q,D,E,M,L,F)
<220> FEATURE:
<221> NAME/KEY: MISC_FEATURE
<222> LOCATION: (47)..(47)
<223> OTHER INFORMATION: Xaa is G (Position 46 and 47 are set so that
      one of them is glycine and the other is any of the following 17
      amino acids; N,H,D,S,K,Y,H,A,V,T,I,Q,D,E,M,L,F)
<220> FEATURE:
<221> NAME/KEY: MISC_FEATURE
<222> LOCATION: (48)..(48)
<223> OTHER INFORMATION: Xaa is any amino acid
<220> FEATURE:
<221> NAME/KEY: MISC_FEATURE
<222> LOCATION: (70)..(70)
```

<223> OTHER INFORMATION: Xaa is I or V
<220> FEATURE:
<221> NAME/KEY: MISC_FEATURE
<222> LOCATION: (71)..(71)
<223> OTHER INFORMATION: Xaa is A or G
<220> FEATURE:
<221> NAME/KEY: MISC_FEATURE
<222> LOCATION: (73)..(73)
<223> OTHER INFORMATION: optionally absent
<220> FEATURE:
<221> NAME/KEY: MISC_FEATURE
<222> LOCATION: (74)..(74)
<223> OTHER INFORMATION: Xaa is D or E
<220> FEATURE:
<221> NAME/KEY: MISC_FEATURE
<222> LOCATION: (79)..(79)
<223> OTHER INFORMATION: Xaa is E, V, I, K, A or T
<220> FEATURE:
<221> NAME/KEY: MISC_FEATURE
<222> LOCATION: (80)..(80)
<223> OTHER INFORMATION: Xaa is G, V, or A
<220> FEATURE:
<221> NAME/KEY: MISC_FEATURE
<222> LOCATION: (82)..(82)
<223> OTHER INFORMATION: Xaa is any amino acid

<400> SEQUENCE: 1

Xaa Ile Val Asn Val Pro Xaa Xaa Xaa Xaa Thr Lys Xaa Gln Gln Leu
1               5                   10                  15

Ala Xaa Xaa Ala Xaa Ala Xaa Tyr Val Xaa Xaa Gln Asn Ala His Leu
            20                  25                  30

Glu Phe Val Glu Asn Xaa Asn Xaa Lys Xaa Gln Xaa Xaa Xaa Xaa Xaa
        35                  40                  45

Met Tyr Tyr Ile Thr Leu Ala Ala Thr Asp Asp Ala Gly Lys Lys Lys
    50                  55                  60

Ile Tyr Lys Ala Lys Xaa Xaa Val Val Xaa Ser Ala Gly Trp Xaa Xaa
65                  70                  75                  80

Val Xaa Glu Phe Lys Leu Val
            85

<210> SEQ ID NO 2
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is G or D
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (10)..(10)
<223> OTHER INFORMATION: Xaa is N or T
<220> FEATURE:
<221> NAME/KEY: MISC_FEATURE
<222> LOCATION: (13)..(13)
<223> OTHER INFORMATION: Xaa is F or Y
<220> FEATURE:
<221> NAME/KEY: MISC_FEATURE
<222> LOCATION: (19)..(19)
<223> OTHER INFORMATION: Xaa is N, R, S, I or Y
<220> FEATURE:
<221> NAME/KEY: MISC_FEATURE
<222> LOCATION: (23)..(23)
<223> OTHER INFORMATION: Xaa is N, I or V
<220> FEATURE:
<221> NAME/KEY: MISC_FEATURE

```
<222> LOCATION: (26)..(26)
<223> OTHER INFORMATION: Xaa is D, Y, N or H
<220> FEATURE:
<221> NAME/KEY: MISC_FEATURE
<222> LOCATION: (27)..(27)
<223> OTHER INFORMATION: Xaa is Q, Y, N or H
<220> FEATURE:
<221> NAME/KEY: MISC_FEATURE
<222> LOCATION: (40)..(40)
<223> OTHER INFORMATION: Xaa is V or C
<220> FEATURE:
<221> NAME/KEY: MISC_FEATURE
<222> LOCATION: (42)..(42)
<223> OTHER INFORMATION: Xaa is E or D
<220> FEATURE:
<221> NAME/KEY: MISC_FEATURE
<222> LOCATION: (44)..(44)
<223> OTHER INFORMATION: Xaa is V, L, I, T, A, S, or W
<220> FEATURE:
<221> NAME/KEY: MISC_FEATURE
<222> LOCATION: (45)..(45)
<223> OTHER INFORMATION: Xaa is T, S, D, G, A,N, or Y
<220> FEATURE:
<221> NAME/KEY: MISC_FEATURE
<222> LOCATION: (46)..(46)
<223> OTHER INFORMATION: Xaa is G, Y, F, A , L, S, E (wherein one of
      residue 46 or 47 is G)
<220> FEATURE:
<221> NAME/KEY: MISC_FEATURE
<222> LOCATION: (47)..(47)
<223> OTHER INFORMATION: Xaa is M, K, G, L, H, Q, E, D , V, or S
      (wherein one of residue 46 or 47 is G)
<220> FEATURE:
<221> NAME/KEY: MISC_FEATURE
<222> LOCATION: (48)..(48)
<223> OTHER INFORMATION: Xaa is N, T, V, A, I, D, G, V, or S
<220> FEATURE:
<221> NAME/KEY: MISC_FEATURE
<222> LOCATION: (70)..(70)
<223> OTHER INFORMATION: Xaa is I or V
<220> FEATURE:
<221> NAME/KEY: MISC_FEATURE
<222> LOCATION: (71)..(71)
<223> OTHER INFORMATION: Xaa is A or G
<220> FEATURE:
<221> NAME/KEY: MISC_FEATURE
<222> LOCATION: (73)..(73)
<223> OTHER INFORMATION: optionally absent
<220> FEATURE:
<221> NAME/KEY: MISC_FEATURE
<222> LOCATION: (74)..(74)
<223> OTHER INFORMATION: Xaa is D or E
<220> FEATURE:
<221> NAME/KEY: MISC_FEATURE
<222> LOCATION: (79)..(79)
<223> OTHER INFORMATION: Xaa is E, V,I, K, A, or T
<220> FEATURE:
<221> NAME/KEY: MISC_FEATURE
<222> LOCATION: (80)..(80)
<223> OTHER INFORMATION: Xaa is G, V, A or E
<220> FEATURE:
<221> NAME/KEY: MISC_FEATURE
<222> LOCATION: (82)..(82)
<223> OTHER INFORMATION: Xaa is T, E, K, R, D, A, S, or N

<400> SEQUENCE: 2

Xaa Ile Val Asn Val Pro Asn Xaa Asn Xaa Thr Lys Xaa Gln Gln Leu
1               5                   10                  15

Ala Arg Xaa Ala Ile Ala Xaa Tyr Asn Xaa Xaa Gln Asn Ala His Leu
            20                  25                  30

Glu Phe Val Glu Asn Leu Asn Xaa Lys Xaa Gln Xaa Xaa Xaa Xaa Xaa
        35                  40                  45

Met Tyr Tyr Ile Thr Leu Ala Ala Thr Asp Asp Ala Gly Lys Lys Lys
    50                  55                  60
```

```
Ile Tyr Lys Ala Lys Xaa Xaa Val Val Xaa Ser Ala Gly Trp Xaa Xaa
 65                  70                  75                  80

Val Xaa Glu Phe Lys Leu Val
            85

<210> SEQ ID NO 3
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (19)..(19)
<223> OTHER INFORMATION: Xaa is N, R, S, Y or I
<220> FEATURE:
<221> NAME/KEY: MISC_FEATURE
<222> LOCATION: (23)..(23)
<223> OTHER INFORMATION: Xaa is I, V or N
<220> FEATURE:
<221> NAME/KEY: MISC_FEATURE
<222> LOCATION: (26)..(26)
<223> OTHER INFORMATION: Xaa is Y, D, H or N
<220> FEATURE:
<221> NAME/KEY: MISC_FEATURE
<222> LOCATION: (27)..(27)
<223> OTHER INFORMATION: Xaa is Y, H, Q or N
<220> FEATURE:
<221> NAME/KEY: MISC_FEATURE
<222> LOCATION: (38)..(38)
<223> OTHER INFORMATION: Xaa is L or M
<220> FEATURE:
<221> NAME/KEY: MISC_FEATURE
<222> LOCATION: (40)..(40)
<223> OTHER INFORMATION: Xaa is V or C
<220> FEATURE:
<221> NAME/KEY: MISC_FEATURE
<222> LOCATION: (42)..(42)
<223> OTHER INFORMATION: Xaa is E or D
<220> FEATURE:
<221> NAME/KEY: MISC_FEATURE
<222> LOCATION: (44)..(44)
<223> OTHER INFORMATION: Xaa is V, L, I, T, A, S, or W
<220> FEATURE:
<221> NAME/KEY: MISC_FEATURE
<222> LOCATION: (45)..(45)
<223> OTHER INFORMATION: Xaa is T, S, D, G, or A
<220> FEATURE:
<221> NAME/KEY: MISC_FEATURE
<222> LOCATION: (46)..(46)
<223> OTHER INFORMATION: Xaa is G, Y, L, H, V, S, or E (wherein one of
      residue 46 or 47 is G)
<220> FEATURE:
<221> NAME/KEY: MISC_FEATURE
<222> LOCATION: (47)..(47)
<223> OTHER INFORMATION: Xaa is M, K, G, L, H, Q, E, D, S or Y (wherein
      one of residue 46 or 47 is G)
<220> FEATURE:
<221> NAME/KEY: MISC_FEATURE
<222> LOCATION: (48)..(48)
<223> OTHER INFORMATION: Xaa is N, T, V, A, I, D, G, V, or S
<220> FEATURE:
<221> NAME/KEY: MISC_FEATURE
<222> LOCATION: (70)..(70)
<223> OTHER INFORMATION: Xaa is I or V
<220> FEATURE:
<221> NAME/KEY: MISC_FEATURE
<222> LOCATION: (71)..(71)
<223> OTHER INFORMATION: Xaa is A or G
<220> FEATURE:
<221> NAME/KEY: MISC_FEATURE
<222> LOCATION: (73)..(73)
<223> OTHER INFORMATION: optionally absent
```

```
<220> FEATURE:
<221> NAME/KEY: MISC_FEATURE
<222> LOCATION: (76)..(76)
<223> OTHER INFORMATION: Xaa is A or S
<220> FEATURE:
<221> NAME/KEY: MISC_FEATURE
<222> LOCATION: (79)..(79)
<223> OTHER INFORMATION: Xaa is E, V, I, K , A, or T
<220> FEATURE:
<221> NAME/KEY: MISC_FEATURE
<222> LOCATION: (80)..(80)
<223> OTHER INFORMATION: Xaa is G, A, V or E
<220> FEATURE:
<221> NAME/KEY: MISC_FEATURE
<222> LOCATION: (82)..(82)
<223> OTHER INFORMATION: Xaa is T, E, S, R, K, N, or A

<400> SEQUENCE: 3

Gly Ile Val Asn Val Pro Asn Xaa Asn Thr Thr Lys Tyr Gln Gln Leu
1               5                   10                  15

Ala Arg Xaa Ala Ile Ala Xaa Tyr Asn Xaa Xaa Gln Asn Ala His Leu
            20                  25                  30

Glu Phe Val Glu Asn Xaa Asn Xaa Lys Xaa Gln Xaa Xaa Xaa Xaa Xaa
            35                  40                  45

Met Tyr Tyr Ile Thr Leu Ala Ala Thr Asp Asp Ala Gly Lys Lys Lys
            50                  55                  60

Ile Tyr Lys Ala Lys Xaa Xaa Val Val Glu Ser Xaa Gly Trp Xaa Xaa
65                  70                  75                  80

Val Xaa Glu Phe Lys Leu Val
                85

<210> SEQ ID NO 4
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is G or A
<220> FEATURE:
<221> NAME/KEY: MISC_FEATURE
<222> LOCATION: (2)..(2)
<223> OTHER INFORMATION: Xaa is I, S, or T
<220> FEATURE:
<221> NAME/KEY: MISC_FEATURE
<222> LOCATION: (5)..(5)
<223> OTHER INFORMATION: Xaa is V or L
<220> FEATURE:
<221> NAME/KEY: MISC_FEATURE
<222> LOCATION: (25)..(25)
<223> OTHER INFORMATION: Xaa is any amino acid
<220> FEATURE:
<221> NAME/KEY: MISC_FEATURE
<222> LOCATION: (26)..(26)
<223> OTHER INFORMATION: Xaa is M, L, F, E or I
<220> FEATURE:
<221> NAME/KEY: MISC_FEATURE
<222> LOCATION: (27)..(27)
<223> OTHER INFORMATION: Xaa is any amino acid
<220> FEATURE:
<221> NAME/KEY: MISC_FEATURE
<222> LOCATION: (28)..(28)
<223> OTHER INFORMATION: Xaa is M, L, V, or I
<220> FEATURE:
<221> NAME/KEY: MISC_FEATURE
<222> LOCATION: (29)..(29)
<223> OTHER INFORMATION: Xaa is V, A, S, P, E, D, Q, N, V, T, L or K
<220> FEATURE:
<221> NAME/KEY: MISC_FEATURE
<222> LOCATION: (33)..(33)
```

```
<223> OTHER INFORMATION: Xaa is W or G
<220> FEATURE:
<221> NAME/KEY: MISC_FEATURE
<222> LOCATION: (34)..(34)
<223> OTHER INFORMATION: Xaa is T, I, V, D or E
<220> FEATURE:
<221> NAME/KEY: MISC_FEATURE
<222> LOCATION: (38)..(38)
<223> OTHER INFORMATION: Xaa is F, I, L, T or S
<220> FEATURE:
<221> NAME/KEY: MISC_FEATURE
<222> LOCATION: (45)..(45)
<223> OTHER INFORMATION: Xaa is K or E
<220> FEATURE:
<221> NAME/KEY: MISC_FEATURE
<222> LOCATION: (47)..(47)
<223> OTHER INFORMATION: Xaa is I or L
<220> FEATURE:
<221> NAME/KEY: MISC_FEATURE
<222> LOCATION: (49)..(49)
<223> OTHER INFORMATION: Xaa is K, E, M or N
<220> FEATURE:
<221> NAME/KEY: MISC_FEATURE
<222> LOCATION: (51)..(51)
<223> OTHER INFORMATION: Xaa is N, D, E, S or G
<220> FEATURE:
<221> NAME/KEY: MISC_FEATURE
<222> LOCATION: (67)..(67)
<223> OTHER INFORMATION: Xaa is K, E or R
<220> FEATURE:
<221> NAME/KEY: MISC_FEATURE
<222> LOCATION: (71)..(71)
<223> OTHER INFORMATION: Xaa is K or E
<220> FEATURE:
<221> NAME/KEY: MISC_FEATURE
<222> LOCATION: (83)..(83)
<223> OTHER INFORMATION: Xaa is D, N, E or K
<220> FEATURE:
<221> NAME/KEY: MISC_FEATURE
<222> LOCATION: (89)..(89)
<223> OTHER INFORMATION: Xaa is F, I or L
<220> FEATURE:
<221> NAME/KEY: MISC_FEATURE
<222> LOCATION: (90)..(90)
<223> OTHER INFORMATION: Xaa is I, L, M, T, A or V
<220> FEATURE:
<221> NAME/KEY: MISC_FEATURE
<222> LOCATION: (91)..(91)
<223> OTHER INFORMATION: Xaa is E, D, K, R, or G

<400> SEQUENCE: 4

Xaa Xaa Gly Met Xaa Ala Ile Ser Met Asp Thr Asp Lys Ile Ser Asn
1               5                   10                  15

Ser Phe Glu Asp Cys Lys Tyr Phe Xaa Xaa Xaa Xaa Xaa Ser Ala Gly
            20                  25                  30

Xaa Xaa Asn Thr Ile Xaa Asn Asp Glu Ser Gly Lys Xaa Glu Xaa Val
        35                  40                  45

Xaa Met Xaa Val Asp Ala Ile Ile Cys Lys Asn Ile Ser Glu Glu Asn
    50                  55                  60

Tyr Lys Xaa Phe Ser Lys Xaa Ile Glu Ile Tyr His Ala Glu Gly Asp
65                  70                  75                  80

Asp Val Xaa Lys Asn Ile Ser Leu Xaa Xaa Xaa Gly Glu Leu Ser Lys
            85                  90                  95

Ile Ser Asn Pro
            100

<210> SEQ ID NO 5
<211> LENGTH: 100
<212> TYPE: PRT
<213> ORGANISM: Artificial Sequence
<220> FEATURE:
```

```
<223> OTHER INFORMATION: Synthetic
<220> FEATURE:
<221> NAME/KEY: MISC_FEATURE
<222> LOCATION: (1)..(1)
<223> OTHER INFORMATION: Xaa is G or A
<220> FEATURE:
<221> NAME/KEY: MISC_FEATURE
<222> LOCATION: (2)..(2)
<223> OTHER INFORMATION: Xaa is I, T or S
<220> FEATURE:
<221> NAME/KEY: MISC_FEATURE
<222> LOCATION: (5)..(5)
<223> OTHER INFORMATION: Xaa is V or L
<220> FEATURE:
<221> NAME/KEY: MISC_FEATURE
<222> LOCATION: (25)..(25)
<223> OTHER INFORMATION: Xaa is Q or L
<220> FEATURE:
<221> NAME/KEY: MISC_FEATURE
<222> LOCATION: (26)..(26)
<223> OTHER INFORMATION: Xaa is I, E or L
<220> FEATURE:
<221> NAME/KEY: MISC_FEATURE
<222> LOCATION: (27)..(27)
<223> OTHER INFORMATION: Xaa is M, V, Y or E
<220> FEATURE:
<221> NAME/KEY: MISC_FEATURE
<222> LOCATION: (28)..(28)
<223> OTHER INFORMATION: Xaa is M, V or L
<220> FEATURE:
<221> NAME/KEY: MISC_FEATURE
<222> LOCATION: (29)..(29)
<223> OTHER INFORMATION: Xaa is P, V, E, L, A or K
<220> FEATURE:
<221> NAME/KEY: MISC_FEATURE
<222> LOCATION: (38)..(38)
<223> OTHER INFORMATION: Xaa is F or S
<220> FEATURE:
<221> NAME/KEY: MISC_FEATURE
<222> LOCATION: (45)..(45)
<223> OTHER INFORMATION: Xaa is K or E
<220> FEATURE:
<221> NAME/KEY: MISC_FEATURE
<222> LOCATION: (49)..(49)
<223> OTHER INFORMATION: Xaa is K or E
<220> FEATURE:
<221> NAME/KEY: MISC_FEATURE
<222> LOCATION: (51)..(51)
<223> OTHER INFORMATION: Xaa is N, S or G
<220> FEATURE:
<221> NAME/KEY: MISC_FEATURE
<222> LOCATION: (83)..(83)
<223> OTHER INFORMATION: Xaa is E, N, D or K
<220> FEATURE:
<221> NAME/KEY: MISC_FEATURE
<222> LOCATION: (90)..(90)
<223> OTHER INFORMATION: Xaa is I, A or L

<400> SEQUENCE: 5

Xaa Xaa Gly Met Xaa Ala Ile Ser Met Asp Thr Asp Lys Ile Ser Asn
1               5                   10                  15

Ser Phe Glu Asp Cys Lys Tyr Phe Xaa Xaa Xaa Xaa Xaa Ser Ala Gly
            20                  25                  30

Trp Thr Asn Thr Ile Xaa Asn Asp Glu Ser Gly Lys Xaa Glu Ile Val
        35                  40                  45

Xaa Met Xaa Val Asp Ala Ile Ile Cys Lys Asn Ile Ser Glu Glu Asn
50                  55                  60

Tyr Lys Lys Phe Ser Lys Lys Ile Glu Ile Tyr His Ala Glu Gly Asp
65                  70                  75                  80

Asp Val Xaa Lys Asn Ile Ser Leu Phe Xaa Glu Gly Glu Leu Ser Lys
            85                  90                  95

Ile Ser Asn Pro
```

```
<210> SEQ ID NO 6
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(5)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is V or M
<220> FEATURE:
<221> NAME/KEY: MISC_FEATURE
<222> LOCATION: (7)..(7)
<223> OTHER INFORMATION: Xaa is P, A, T, I, L or V
<220> FEATURE:
<221> NAME/KEY: MISC_FEATURE
<222> LOCATION: (12)..(12)
<223> OTHER INFORMATION: Xaa is E, V, T, I, A or K
<220> FEATURE:
<221> NAME/KEY: MISC_FEATURE
<222> LOCATION: (13)..(13)
<223> OTHER INFORMATION: Xaa is any amino acid
<220> FEATURE:
<221> NAME/KEY: MISC_FEATURE
<222> LOCATION: (15)..(15)
<223> OTHER INFORMATION: Xaa is any amino acid

<400> SEQUENCE: 6

Gly Xaa Cys Xaa Xaa Xaa Xaa Ser Ala Gly Trp Xaa Xaa Cys Xaa
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is G, W, R, H, D, Y, E, Q, or C
<220> FEATURE:
<221> NAME/KEY: MISC_FEATURE
<222> LOCATION: (4)..(4)
<223> OTHER INFORMATION: Xaa is I, L, M, or F
<220> FEATURE:
<221> NAME/KEY: MISC_FEATURE
<222> LOCATION: (7)..(7)
<223> OTHER INFORMATION: Xaa is P or A
<220> FEATURE:
<221> NAME/KEY: MISC_FEATURE
<222> LOCATION: (12)..(12)
<223> OTHER INFORMATION: Xaa is E, V, T, I, A, or K
<220> FEATURE:
<221> NAME/KEY: MISC_FEATURE
<222> LOCATION: (13)..(13)
<223> OTHER INFORMATION: Xaa is W, I, V, R, M, G, L, or V
<220> FEATURE:
<221> NAME/KEY: MISC_FEATURE
<222> LOCATION: (15)..(15)
<223> OTHER INFORMATION: Xaa is P, W, D, R, S, A, E, Y, H, Q, C, or G

<400> SEQUENCE: 7

Gly Xaa Cys Xaa Gly Val Xaa Ser Ala Gly Trp Xaa Xaa Cys Xaa
1               5                   10                  15
```

```
<210> SEQ ID NO 8
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is G, W, R, or H
<220> FEATURE:
<221> NAME/KEY: MISC_FEATURE
<222> LOCATION: (4)..(4)
<223> OTHER INFORMATION: Xaa is I, L or M
<220> FEATURE:
<221> NAME/KEY: MISC_FEATURE
<222> LOCATION: (7)..(7)
<223> OTHER INFORMATION: Xaa is P or A
<220> FEATURE:
<221> NAME/KEY: MISC_FEATURE
<222> LOCATION: (12)..(12)
<223> OTHER INFORMATION: Xaa is E, V, T or I
<220> FEATURE:
<221> NAME/KEY: MISC_FEATURE
<222> LOCATION: (13)..(13)
<223> OTHER INFORMATION: Xaa is W, I, V or R
<220> FEATURE:
<221> NAME/KEY: MISC_FEATURE
<222> LOCATION: (15)..(15)
<223> OTHER INFORMATION: Xaa is P, W, D or R

<400> SEQUENCE: 8

Gly Xaa Cys Xaa Gly Val Xaa Ser Ala Gly Trp Xaa Xaa Cys Xaa
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is G, W, R, H, D, or Y
<220> FEATURE:
<221> NAME/KEY: MISC_FEATURE
<222> LOCATION: (4)..(4)
<223> OTHER INFORMATION: Xaa is I, L, or M
<220> FEATURE:
<221> NAME/KEY: MISC_FEATURE
<222> LOCATION: (7)..(7)
<223> OTHER INFORMATION: Xaa is P or A
<220> FEATURE:
<221> NAME/KEY: MISC_FEATURE
<222> LOCATION: (13)..(13)
<223> OTHER INFORMATION: Xaa is W, I or V
<220> FEATURE:
<221> NAME/KEY: MISC_FEATURE
<222> LOCATION: (15)..(15)
<223> OTHER INFORMATION: Xaa is W or P

<400> SEQUENCE: 9

Gly Xaa Cys Xaa Gly Val Xaa Ser Ala Gly Trp Glu Xaa Cys Xaa
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic
<220> FEATURE:
```

```
<221> NAME/KEY: MISC_FEATURE
<222> LOCATION: (2)..(2)
<223> OTHER INFORMATION: Xaa is S, F, D, C, M, N, K, G, T, R, W, or V
<220> FEATURE:
<221> NAME/KEY: MISC_FEATURE
<222> LOCATION: (4)..(4)
<223> OTHER INFORMATION: Xaa is P, C, T, G, F, R, A, Y, I, W, or V
<220> FEATURE:
<221> NAME/KEY: MISC_FEATURE
<222> LOCATION: (5)..(5)
<223> OTHER INFORMATION: Xaa is F, L, C, Y, H, A, W, R, V, P, G, or K
<220> FEATURE:
<221> NAME/KEY: MISC_FEATURE
<222> LOCATION: (6)..(6)
<223> OTHER INFORMATION: Xaa is V, M or A
<220> FEATURE:
<221> NAME/KEY: MISC_FEATURE
<222> LOCATION: (7)..(7)
<223> OTHER INFORMATION: Xaa is T, I, L, V, or A
<220> FEATURE:
<221> NAME/KEY: MISC_FEATURE
<222> LOCATION: (13)..(13)
<223> OTHER INFORMATION: Xaa is K, E, P, M, V, I, T, A, or G
<220> FEATURE:
<221> NAME/KEY: MISC_FEATURE
<222> LOCATION: (15)..(15)
<223> OTHER INFORMATION: Xaa is L, Y, E, S, K, A, N, R, or V, or is
      absent

<400> SEQUENCE: 10

Gly Xaa Cys Xaa Xaa Xaa Xaa Ser Ala Gly Trp Glu Xaa Cys Xaa
1               5                   10                  15

<210> SEQ ID NO 11
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 11

Gly Ile Val Asn Val Pro Asn Xaa Asn Asn Thr Lys Phe Gln Gln Leu
1               5                   10                  15

Ala Arg Asn Ala Ile Ala Asn Tyr Asn Asp Asn Gln Asn Ala His Leu
            20                  25                  30

Glu Phe Val Glu Asn Leu Asn Xaa Lys Glu Gln Val Thr Gly Gly Ile
        35                  40                  45

Met Tyr Tyr Ile Thr Leu Ala Ala Thr Asp Asp Ala Gly Lys Lys Lys
    50                  55                  60

Ile Tyr Lys Ala Lys Ile Ala Val Val Asp Ser Ala Gly Trp Glu Gly
65                  70                  75                  80

Val Thr Glu Phe Lys Leu Val
                85

<210> SEQ ID NO 12
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
```

<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 12

Gly Ile Val Asn Val Pro Asn Xaa Asn Asn Thr Lys Phe Gln Gln Leu
1               5                   10                  15

Ala Arg Asn Ala Ile Ala Asn Tyr Asn Asp Tyr Gln Asn Ala His Leu
            20                  25                  30

Glu Phe Val Glu Asn Leu Asn Xaa Lys Glu Gln Val Thr Gly Asp Ile
        35                  40                  45

Met Tyr Tyr Ile Thr Leu Ala Ala Thr Asp Asp Ala Gly Lys Lys Lys
    50                  55                  60

Ile Tyr Lys Ala Lys Ile Ala Val Val Asp Ser Ala Gly Trp Glu Gly
65                  70                  75                  80

Val Thr Glu Phe Lys Leu Val
                85

<210> SEQ ID NO 13
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 13

Gly Ile Val Asn Val Pro Asn Xaa Asn Asn Thr Lys Phe Gln Gln Leu
1               5                   10                  15

Ala Arg Tyr Ala Ile Ala Asn Tyr Asn Asp Asn Gln Asn Ala His Leu
            20                  25                  30

Glu Phe Val Glu Asn Leu Asn Xaa Lys Glu Gln Val Thr Gly Gly Ile
        35                  40                  45

Met Tyr Tyr Ile Thr Leu Ala Ala Thr Asp Asp Ala Gly Lys Lys Lys
    50                  55                  60

Ile Tyr Lys Ala Lys Ile Ala Val Val Asp Ser Ala Gly Trp Val Gly
65                  70                  75                  80

Val Thr Glu Phe Lys Leu Val
                85

<210> SEQ ID NO 14
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C -continued

<400> SEQUENCE: 14

Gly Ile Val Asn Val Pro Lys Xaa Asn Asn Thr Lys Phe Gln Gln Leu
1               5                   10                  15

Ala Arg Tyr Ala Ile Ala Asn Tyr Asn Asp Asn Gln Asn Ala His Leu
            20                  25                  30

Glu Phe Val Glu Asn Leu Asn Xaa Lys Glu Gln Val Thr Gly Gly Ile
        35                  40                  45

Met Tyr Tyr Ile Thr Leu Ala Ala Thr Asp Asp Ala Gly Lys Lys Lys
    50                  55                  60

Ile Tyr Lys Ala Lys Ile Ala Val Val Asp Ser Ala Gly Trp Val Gly
65                  70                  75                  80

Val Thr Glu Phe Lys Leu Val
                85

<210> SEQ ID NO 15
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 15

Gly Ile Val Asn Val Pro Asn Xaa Asn Thr Thr Lys Tyr Gln Gln Leu
1               5                   10                  15

Ala Arg Ser Ala Ile Ala Ile Tyr Asn Tyr His Gln Asn Ala His Leu
            20                  25                  30

Glu Phe Val Glu Asn Leu Asn Xaa Lys Glu Gln Val Gly Gly Met Asn
        35                  40                  45

Met Tyr Tyr Ile Thr Leu Ala Ala Thr Asp Asp Ala Gly Lys Lys Lys
    50                  55                  60

Ile Tyr Lys Ala Lys Val Gly Val Val Glu Ser Ala Gly Trp Lys Gly
65                  70                  75                  80

Val Glu Glu Phe Lys Leu Val
                85

<210> SEQ ID NO 16
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 16

Gly Ile Val Asn Val Pro Asn Xaa Asn Thr Thr Lys Tyr Gln Gln Leu
1               5                   10                  15

Ala Arg Ser Ala Ile Ala Val Tyr Asn Tyr His Gln Asn Ala His Leu
            20                  25                  30

Glu Phe Val Glu Asn Leu Asn Xaa Lys Glu Gln Ile Ala Gly Lys Thr
            35                  40                  45

Met Tyr Tyr Ile Thr Leu Ala Ala Thr Asp Asp Ala Gly Lys Lys Lys
 50                  55                  60

Ile Tyr Lys Ala Lys Val Gly Val Glu Ser Ala Gly Trp Glu Gly
 65                  70                  75                  80

Val Glu Glu Phe Lys Leu Val
                85

<210> SEQ ID NO 17
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 17

Gly Ile Val Asn Val Pro Asn Xaa Asn Thr Thr Lys Tyr Gln Gln Leu
 1               5                  10                  15

Ala Arg Ile Ala Ile Ala Val Tyr Asn Asn Tyr Gln Asn Ala His Leu
                20                  25                  30

Glu Phe Val Glu Asn Leu Asn Xaa Lys Glu Gln Ser Gly Gly Lys Val
            35                  40                  45

Met Tyr Tyr Ile Thr Leu Ala Ala Thr Asp Asp Ala Gly Lys Lys Lys
 50                  55                  60

Ile Tyr Lys Ala Lys Val Gly Val Glu Ser Ala Gly Trp Ile Gly
 65                  70                  75                  80

Val Glu Glu Phe Lys Leu Val
                85

<210> SEQ ID NO 18
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 18

Gly Ile Val Asn Val Pro Asn Xaa Asn Thr Thr Lys Tyr Gln Gln Leu
 1               5                  10                  15

Ala Arg Ser Ala Ile Ala Val Tyr Asn Asn His Gln Asn Ala His Leu
                20                  25                  30

Glu Phe Val Glu Asn Leu Asn Xaa Lys Glu Gln Ala Gly Gly Lys Ala
            35                  40                  45

Met Tyr Tyr Ile Thr Leu Ala Ala Thr Asp Asp Ala Gly Lys Lys Lys
 50                  55                  60

```
Ile Tyr Lys Ala Lys Ile Gly Val Val Glu Ser Ala Gly Trp Glu Gly
 65                  70                  75                  80

Val Glu Glu Phe Lys Leu Val
                85
```

<210> SEQ ID NO 19
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 19

```
Gly Ile Val Asn Val Pro Asn Xaa Asn Thr Thr Lys Tyr Gln Gln Leu
  1               5                  10                  15

Ala Arg Arg Ala Ile Ala Ile Tyr Asn Asn Gln Asn Ala His Leu
                 20                  25                  30

Glu Phe Val Glu Asn Leu Asn Xaa Lys Glu Gln Thr Gly Leu Gly Ile
             35                  40                  45

Met Tyr Tyr Ile Thr Leu Ala Ala Thr Asp Asp Ala Gly Lys Lys Lys
 50                  55                  60

Ile Tyr Lys Ala Lys Ile Ala Val Val Glu Ser Ala Gly Trp Val Ala
 65                  70                  75                  80

Val Ser Glu Phe Lys Leu Val
                85
```

<210> SEQ ID NO 20
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 20

```
Gly Ile Val Asn Val Pro Asn Xaa Asn Thr Thr Lys Tyr Gln Gln Leu
  1               5                  10                  15

Ala Arg Ser Ala Ile Ala Val Tyr Asn Asn His Gln Asn Ala His Leu
                 20                  25                  30

Glu Phe Val Glu Asn Leu Asn Xaa Lys Glu Gln Ala Gly Gly Lys Ala
             35                  40                  45

Met Tyr Tyr Ile Thr Leu Ala Ala Thr Asp Asp Ala Gly Lys Lys Lys
 50                  55                  60

Ile Tyr Lys Ala Lys Ile Gly Val Val Glu Ser Ala Gly Trp Glu Gly
 65                  70                  75                  80

Val Glu Glu Phe Lys Leu Val
                85
```

```
<210> SEQ ID NO 21
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 21

Gly Ile Val Asn Val Pro Asn Xaa Asn Thr Thr Lys Tyr Gln Gln Leu
1               5                   10                  15

Ala Arg Ser Ala Ile Ala Val Tyr Asn Tyr His Gln Asn Ala His Leu
            20                  25                  30

Glu Phe Val Glu Asn Leu Asn Xaa Lys Glu Gln Ile Ala Gly Lys Thr
        35                  40                  45

Met Tyr Tyr Ile Thr Leu Ala Ala Thr Asp Asp Ala Gly Lys Lys Lys
    50                  55                  60

Ile Tyr Lys Ala Lys Val Gly Val Val Glu Ser Ala Gly Trp Glu Gly
65                  70                  75                  80

Val Glu Glu Phe Lys Leu Val
                85

<210> SEQ ID NO 22
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 22

Gly Ile Val Asn Val Pro Asn Xaa Asn Thr Thr Lys Tyr Gln Gln Leu
1               5                   10                  15

Ala Arg Ser Ala Ile Ala Val Tyr Asn Asn His Gln Asn Ala His Leu
            20                  25                  30

Glu Phe Val Glu Asn Leu Asn Xaa Lys Glu Gln Ala Gly Gly Lys Ala
        35                  40                  45

Met Tyr Tyr Ile Thr Leu Ala Ala Thr Asp Asp Ala Gly Lys Lys Lys
    50                  55                  60

Ile Tyr Lys Ala Lys Ile Gly Val Val Glu Ser Ala Gly Trp Glu Gly
65                  70                  75                  80

Val Glu Glu Phe Lys Leu Val
                85

<210> SEQ ID NO 23
<211> LENGTH: 87
<212> TYPE: PRT
<213> ORGANISM: Artificial Sequence
<220> FEATURE:
<223> OTHER INFORMATION: Synthetic
<220> FEATURE:
```

```
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 23

Gly Ile Val Asn Val Pro Asn Xaa Asn Thr Thr Lys Tyr Gln Gln Leu
1               5                   10                  15

Ala Arg Arg Ala Ile Ala Ile Tyr Asn Asn Gln Asn Ala His Leu
            20                  25                  30

Glu Phe Val Glu Asn Leu Asn Xaa Lys Glu Gln Thr Gly Leu Gly Ile
            35                  40                  45

Met Tyr Tyr Ile Thr Leu Ala Ala Thr Asp Asp Ala Gly Lys Lys Lys
    50                  55                  60

Ile Tyr Lys Ala Lys Ile Ala Val Val Glu Ser Ala Gly Trp Val Ala
65                  70                  75                  80

Val Ser Glu Phe Lys Leu Val
                85

<210> SEQ ID NO 24
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 24

Gly Ile Val Asn Val Pro Asn Xaa Asn Thr Thr Lys Tyr Gln Gln Leu
1               5                   10                  15

Ala Arg Arg Ala Ile Ala Ile Tyr Asn Asn Gln Asn Ala His Leu
            20                  25                  30

Glu Phe Val Glu Asn Leu Asn Xaa Lys Glu Gln Trp Gly Leu Gly Ile
            35                  40                  45

Met Tyr Tyr Ile Thr Leu Ala Ala Thr Asp Asp Ala Gly Lys Lys Lys
    50                  55                  60

Ile Tyr Lys Ala Lys Ile Ala Val Val Glu Ser Ala Gly Trp Val Ala
65                  70                  75                  80

Val Ser Glu Phe Lys Leu Val
                85

<210> SEQ ID NO 25
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C
```

<400> SEQUENCE: 25

Gly Ile Val Asn Val Pro Asn Xaa Asn Thr Thr Lys Tyr Gln Gln Leu
1               5                   10                  15

Ala Arg Arg Ala Ile Ala Ile Tyr Asn Asn Asn Gln Asn Ala His Leu
            20                  25                  30

Glu Phe Val Glu Asn Leu Asn Xaa Lys Asp Gln Thr Gly Leu Gly Ile
        35                  40                  45

Met Tyr Tyr Ile Thr Leu Ala Ala Thr Asp Asp Ala Gly Lys Lys Lys
    50                  55                  60

Ile Tyr Lys Ala Lys Ile Ala Val Val Glu Ser Ala Gly Trp Val Ala
65                  70                  75                  80

Val Ser Glu Phe Lys Leu Val
                85

<210> SEQ ID NO 26
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 26

Gly Ile Val Asn Val Pro Asn Xaa Asn Thr Thr Lys Tyr Gln Gln Leu
1               5                   10                  15

Ala Arg Ser Ala Ile Ala Ile Tyr Asn Asn His Gln Asn Ala His Leu
            20                  25                  30

Glu Phe Val Glu Asn Leu Asn Xaa Lys Glu Gln Val Ser Tyr Gly Ala
        35                  40                  45

Met Tyr Tyr Ile Thr Leu Ala Ala Thr Asp Asp Ala Gly Lys Lys Lys
    50                  55                  60

Ile Tyr Lys Ala Lys Val Gly Val Val Glu Ser Ala Gly Trp Val Gly
65                  70                  75                  80

Val Glu Glu Phe Lys Leu Val
                85

<210> SEQ ID NO 27
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 27

Gly Ile Val Asn Val Pro Asn Xaa Asn Thr Thr Lys Tyr Gln Gln Leu
1               5                   10                  15

Ala Arg Ser Ala Ile Ala Val Tyr Asn Tyr His Gln Asn Ala His Leu

```
                    20                  25                  30

Glu Phe Val Glu Asn Leu Asn Xaa Lys Glu Gln Ile Asp Tyr Gly Ala
            35                  40                  45

Met Tyr Tyr Ile Thr Leu Ala Ala Thr Asp Asp Ala Gly Lys Lys Lys
    50                  55                  60

Ile Tyr Lys Ala Lys Ile Gly Val Val Glu Ser Ala Gly Trp Ile Gly
65                  70                  75                  80

Val Glu Glu Phe Lys Leu Val
                85

<210> SEQ ID NO 28
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 28

Gly Ile Val Asn Val Pro Asn Xaa Asn Thr Thr Lys Tyr Gln Gln Leu
1               5                   10                  15

Ala Arg Arg Ala Ile Ala Ile Tyr Asn Asn Asn Gln Asn Ala His Leu
            20                  25                  30

Glu Phe Val Glu Asn Leu Asn Xaa Lys Glu Gln Trp Gly Leu Gly Ile
            35                  40                  45

Met Tyr Tyr Ile Thr Leu Ala Ala Thr Asp Asp Ala Gly Lys Lys Lys
    50                  55                  60

Ile Tyr Lys Ala Lys Ile Ala Val Val Glu Ser Ala Gly Trp Val Ala
65                  70                  75                  80

Val Ser Glu Phe Lys Leu Val
                85

<210> SEQ ID NO 29
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 29

Gly Ile Val Asn Val Pro Asn Xaa Asn Thr Thr Lys Tyr Gln Gln Leu
1               5                   10                  15

Ala Arg Ser Ala Ile Ala Ile Tyr Asn Asn Asn Gln Asn Ala His Leu
            20                  25                  30

Glu Phe Val Glu Asn Leu Asn Xaa Lys Glu Gln Leu Asn Gly Tyr Asp
            35                  40                  45

Met Tyr Tyr Ile Thr Leu Ala Ala Thr Asp Asp Ala Gly Lys Lys Lys
    50                  55                  60
```

```
Ile Tyr Lys Ala Lys Ile Gly Val Val Glu Ser Ala Gly Trp Thr Gly
 65                  70                  75                  80

Val Asn Glu Phe Lys Leu Val
                 85
```

<210> SEQ ID NO 30
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 30

```
Gly Ile Val Asn Val Pro Asn Xaa Asn Thr Thr Lys Tyr Gln Gln Leu
  1               5                  10                  15

Ala Arg Ser Ala Ile Ala Ile Tyr Asn His Tyr Gln Asn Ala His Leu
                 20                  25                  30

Glu Phe Val Glu Asn Leu Asn Xaa Lys Glu Gln Ile Thr Gly Tyr Asp
             35                  40                  45

Met Tyr Tyr Ile Thr Leu Ala Ala Thr Asp Asp Ala Gly Lys Lys Lys
         50                  55                  60

Ile Tyr Lys Ala Lys Val Ala Val Val Glu Ser Ala Gly Trp Glu Val
 65                  70                  75                  80

Val Ala Glu Phe Lys Leu Val
                 85
```

<210> SEQ ID NO 31
<211> LENGTH: 86
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 31

```
Gly Ile Val Asn Val Pro Asn Xaa Asn Thr Thr Lys Tyr Gln Gln Leu
  1               5                  10                  15

Ala Arg Arg Ala Ile Ala Val Tyr Asn Tyr Tyr Gln Asn Ala His Leu
                 20                  25                  30

Glu Phe Val Glu Asn Leu Asn Xaa Lys Glu Gln Ser Ser Gly Leu Asp
             35                  40                  45

Met Tyr Tyr Ile Thr Leu Ala Ala Thr Asp Asp Ala Gly Lys Lys Lys
         50                  55                  60

Ile Tyr Lys Ala Lys Ile Ala Val Glu Ser Ala Gly Trp Ile Val Val
 65                  70                  75                  80

Thr Glu Phe Lys Leu Val
                 85
```

<210> SEQ ID NO 32
<211> LENGTH: 86
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 32

```
Gly Ile Val Asn Val Pro Asn Xaa Asn Thr Thr Lys Tyr Gln Gln Leu
 1               5                  10                  15

Ala Arg Arg Ala Ile Ala Val Tyr Asn Tyr Tyr Gln Asn Ala His Leu
            20                  25                  30

Glu Phe Val Glu Asn Leu Asn Xaa Lys Glu Gln Leu Thr Gly His Gly
        35                  40                  45

Met Tyr Tyr Ile Thr Leu Ala Ala Thr Asp Asp Ala Gly Lys Lys Lys
    50                  55                  60

Ile Tyr Lys Ala Lys Val Ala Val Glu Ser Ala Gly Trp Ile Val Val
65                  70                  75                  80

Thr Glu Phe Lys Leu Val
                85
```

<210> SEQ ID NO 33
<211> LENGTH: 86
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 33

```
Gly Ile Val Asn Val Pro Asn Xaa Asn Thr Thr Lys Tyr Gln Gln Leu
 1               5                  10                  15

Ala Arg Arg Ala Ile Ala Val Tyr Asn Tyr Tyr Gln Asn Ala His Leu
            20                  25                  30

Glu Phe Val Glu Asn Leu Asn Xaa Lys Glu Gln Ala Gly Gly Gln Val
        35                  40                  45

Met Tyr Tyr Ile Thr Leu Ala Ala Thr Asp Asp Ala Gly Lys Lys Lys
    50                  55                  60

Ile Tyr Lys Ala Lys Val Ala Val Glu Ser Ala Gly Trp Ile Val Val
65                  70                  75                  80

Thr Glu Phe Lys Leu Val
                85
```

<210> SEQ ID NO 34
<211> LENGTH: 86
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 34

Gly Ile Val Asn Val Pro Asn Xaa Asn Thr Thr Lys Tyr Gln Gln Leu
1               5                   10                  15

Ala Arg Arg Ala Ile Ala Val Tyr Asn Tyr Tyr Gln Asn Ala His Leu
            20                  25                  30

Glu Phe Val Glu Asn Leu Asn Xaa Lys Glu Gln Ala Ala Gly Glu Ile
        35                  40                  45

Met Tyr Tyr Ile Thr Leu Ala Ala Thr Asp Asp Ala Gly Lys Lys Lys
    50                  55                  60

Ile Tyr Lys Ala Lys Ile Ala Val Glu Ser Ala Gly Trp Ile Val Val
65                  70                  75                  80

Arg Glu Phe Lys Leu Val
                85

<210> SEQ ID NO 35
<211> LENGTH: 86
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 35

Gly Ile Val Asn Val Pro Asn Xaa Asn Thr Thr Lys Tyr Gln Gln Leu
1               5                   10                  15

Ala Arg Arg Ala Ile Ala Val Tyr Asn Tyr Tyr Gln Asn Ala His Leu
            20                  25                  30

Glu Phe Val Glu Asn Leu Asn Xaa Lys Glu Gln Ala Ala Gly Glu Ile
        35                  40                  45

Met Tyr Tyr Ile Thr Leu Ala Ala Thr Asp Asp Ala Gly Lys Lys Lys
    50                  55                  60

Ile Tyr Lys Ala Lys Ile Ala Val Glu Ser Ala Gly Trp Ile Val Val
65                  70                  75                  80

Arg Glu Phe Lys Leu Val
                85

<210> SEQ ID NO 36
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)

<223> OTHER INFORMATION: Xaa is V or C

<400> SEQUENCE: 36

```
Gly Ile Val Asn Val Pro Asn Xaa Asn Thr Thr Lys Tyr Gln Gln Leu
1               5                   10                  15

Ala Arg Ile Ala Ile Ala Ile Tyr Asn Tyr His Gln Asn Ala His Leu
            20                  25                  30

Glu Phe Val Glu Asn Leu Asn Xaa Lys Glu Gln Ser Gly His Gly Thr
        35                  40                  45

Met Tyr Tyr Ile Thr Leu Ala Ala Thr Asp Asp Ala Gly Lys Lys Lys
    50                  55                  60

Ile Tyr Lys Ala Lys Val Gly Val Val Glu Ser Ala Gly Trp Ile Gly
65                  70                  75                  80

Val Thr Glu Phe Lys Leu Val
                85
```

<210> SEQ ID NO 37
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 37

```
Gly Ile Val Asn Val Pro Asn Xaa Asn Thr Thr Lys Tyr Gln Gln Leu
1               5                   10                  15

Ala Arg Ile Ala Ile Ala Val Tyr Asn His His Gln Asn Ala His Leu
            20                  25                  30

Glu Phe Val Glu Asn Leu Asn Xaa Lys Glu Gln Ile Ser Val Gly Thr
        35                  40                  45

Met Tyr Tyr Ile Thr Leu Ala Ala Thr Asp Asp Ala Gly Lys Lys Lys
    50                  55                  60

Ile Tyr Lys Ala Lys Val Gly Val Val Glu Ser Ala Gly Trp Ile Glu
65                  70                  75                  80

Val Glu Glu Phe Lys Leu Val
                85
```

<210> SEQ ID NO 38
<211> LENGTH: 86
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 38

```
Gly Ile Val Asn Val Pro Asn Xaa Asn Thr Thr Lys Tyr Gln Gln Leu
1               5                   10                  15
```

```
Ala Arg Arg Ala Ile Ala Val Tyr Asn Tyr Tyr Gln Asn Ala His Leu
            20                  25                  30

Glu Phe Val Glu Asn Leu Asn Xaa Lys Glu Gln Leu Thr Leu Gly Val
        35                  40                  45

Met Tyr Tyr Ile Thr Leu Ala Ala Thr Asp Asp Ala Gly Lys Lys Lys
    50                  55                  60

Ile Tyr Lys Ala Lys Val Ala Val Glu Ser Ala Gly Trp Ile Val Val
65                  70                  75                  80

Thr Glu Phe Lys Leu Val
                85

<210> SEQ ID NO 39
<211> LENGTH: 86
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 39

Gly Ile Val Asn Val Pro Asn Xaa Asn Thr Thr Lys Tyr Gln Gln Leu
1               5                   10                  15

Ala Arg Arg Ala Ile Ala Val Tyr Asn Tyr Tyr Gln Asn Ala His Leu
            20                  25                  30

Glu Phe Val Glu Asn Leu Asn Xaa Lys Glu Gln Ser Ser Ser Gly Asn
        35                  40                  45

Met Tyr Tyr Ile Thr Leu Ala Ala Thr Asp Asp Ala Gly Lys Lys Lys
    50                  55                  60

Ile Tyr Lys Ala Lys Ile Ala Val Glu Ser Ala Gly Trp Ile Val Val
65                  70                  75                  80

Lys Glu Phe Lys Leu Val
                85

<210> SEQ ID NO 40
<211> LENGTH: 100
<212> TYPE: PRT
<213> ORGANISM: Artificial Sequence
<220> FEATURE:
<223> OTHER INFORMATION: Synthetic

<400> SEQUENCE: 40

Gly Ile Gly Met Val Ala Ile Ser Met Asp Thr Asp Lys Ile Ser Asn
1               5                   10                  15

Ser Phe Glu Asp Cys Lys Tyr Phe Leu Ile Val Val Ser Ala Gly
            20                  25                  30

Trp Thr Asn Thr Ile Phe Asn Asp Glu Ser Gly Lys Lys Glu Ile Val
        35                  40                  45

Lys Met Asn Val Asp Ala Ile Ile Cys Lys Asn Ile Ser Glu Glu Asn
    50                  55                  60

Tyr Lys Lys Phe Ser Lys Lys Ile Glu Ile Tyr His Ala Glu Gly Asp
65                  70                  75                  80

Asp Val Asp Lys Asn Ile Ser Leu Phe Ile Glu Gly Glu Leu Ser Lys
                85                  90                  95
```

Ile Ser Asn Pro
            100

<210> SEQ ID NO 41
<211> LENGTH: 100
<212> TYPE: PRT
<213> ORGANISM: Artificial Sequence
<220> FEATURE:
<223> OTHER INFORMATION: Synthetic

<400> SEQUENCE: 41

Gly Ile Gly Met Val Ala Ile Ser Met Asp Thr Asp Lys Ile Ser Asn
1               5                   10                  15

Ser Phe Glu Asp Cys Lys Tyr Phe Leu Ile Met Val Val Ser Ala Gly
            20                  25                  30

Trp Thr Asn Thr Ile Ser Asn Asp Glu Ser Gly Lys Lys Glu Ile Val
        35                  40                  45

Glu Met Asn Val Asp Ala Ile Ile Cys Lys Asn Ile Ser Glu Glu Asn
    50                  55                  60

Tyr Lys Lys Phe Ser Lys Lys Ile Glu Ile Tyr His Ala Glu Gly Asp
65                  70                  75                  80

Asp Val Asp Lys Asn Ile Ser Leu Phe Ile Glu Gly Glu Leu Ser Lys
                85                  90                  95

Ile Ser Asn Pro
            100

<210> SEQ ID NO 42
<211> LENGTH: 100
<212> TYPE: PRT
<213> ORGANISM: Artificial Sequence
<220> FEATURE:
<223> OTHER INFORMATION: Synthetic

<400> SEQUENCE: 42

Gly Ile Gly Met Val Ala Ile Ser Met Asp Thr Asp Lys Ile Ser Asn
1               5                   10                  15

Ser Phe Glu Asp Cys Lys Tyr Phe Leu Ile Val Val Glu Ser Ala Gly
            20                  25                  30

Trp Thr Asn Thr Ile Phe Asn Asp Glu Ser Gly Lys Lys Glu Ile Val
        35                  40                  45

Lys Met Asn Val Asp Ala Ile Ile Cys Lys Asn Ile Ser Glu Glu Asn
    50                  55                  60

Tyr Lys Lys Phe Ser Lys Lys Ile Glu Ile Tyr His Ala Glu Gly Asp
65                  70                  75                  80

Asp Val Asp Lys Asn Ile Ser Leu Phe Ile Glu Gly Glu Leu Ser Lys
                85                  90                  95

Ile Ser Asn Pro
            100

<210> SEQ ID NO 43
<211> LENGTH: 100
<212> TYPE: PRT
<213> ORGANISM: Artificial Sequence
<220> FEATURE:
<223> OTHER INFORMATION: Synthetic

<400> SEQUENCE: 43

Gly Thr Gly Met Val Ala Ile Ser Met Asp Thr Asp Lys Ile Ser Asn
1               5                   10                  15

Ser Phe Glu Asp Cys Lys Tyr Phe Leu Ile Val Met Val Ser Ala Gly

```
                    20                  25                  30

Trp Thr Asn Thr Ile Phe Asn Asp Glu Ser Gly Lys Lys Glu Ile Val
            35                  40                  45

Lys Met Asn Val Asp Ala Ile Ile Cys Lys Asn Ile Ser Glu Glu Asn
        50                  55                  60

Tyr Lys Lys Phe Ser Lys Lys Ile Glu Ile Tyr His Ala Glu Gly Asp
65                  70                  75                  80

Asp Val Asp Lys Asn Ile Ser Leu Phe Ile Glu Gly Glu Leu Ser Lys
                85                  90                  95

Ile Ser Asn Pro
            100

<210> SEQ ID NO 44
<211> LENGTH: 100
<212> TYPE: PRT
<213> ORGANISM: Artificial Sequence
<220> FEATURE:
<223> OTHER INFORMATION: Synthetic

<400> SEQUENCE: 44

Gly Thr Gly Met Val Ala Ile Ser Met Asp Thr Asp Lys Ile Ser Asn
1               5                   10                  15

Ser Phe Glu Asp Cys Lys Tyr Phe Leu Ile Met Val Val Ser Ala Gly
            20                  25                  30

Trp Thr Asn Thr Ile Phe Asn Asp Glu Ser Gly Lys Lys Glu Ile Val
        35                  40                  45

Glu Met Asn Val Asp Ala Ile Ile Cys Lys Asn Ile Ser Glu Glu Asn
    50                  55                  60

Tyr Lys Lys Phe Ser Lys Lys Ile Glu Ile Tyr His Ala Glu Gly Asp
65                  70                  75                  80

Asp Val Asp Lys Asn Ile Ser Leu Phe Ile Glu Gly Glu Leu Ser Lys
                85                  90                  95

Ile Ser Asn Pro
            100

<210> SEQ ID NO 45
<211> LENGTH: 100
<212> TYPE: PRT
<213> ORGANISM: Artificial Sequence
<220> FEATURE:
<223> OTHER INFORMATION: Synthetic

<400> SEQUENCE: 45

Ala Ser Gly Met Leu Ala Ile Ser Met Asp Thr Asp Lys Ile Ser Asn
1               5                   10                  15

Ser Phe Glu Asp Cys Lys Tyr Phe Leu Ile Glu Leu Lys Ser Ala Gly
            20                  25                  30

Trp Thr Asn Thr Ile Phe Asn Asp Glu Ser Gly Lys Glu Glu Ile Val
        35                  40                  45

Lys Met Gly Val Asp Ala Ile Ile Cys Lys Asn Ile Ser Glu Glu Asn
    50                  55                  60

Tyr Lys Lys Phe Ser Lys Lys Ile Glu Ile Tyr His Ala Glu Gly Asp
65                  70                  75                  80

Asp Val Asn Lys Asn Ile Ser Leu Phe Leu Glu Gly Glu Leu Ser Lys
                85                  90                  95

Ile Ser Asn Pro
            100
```

<210> SEQ ID NO 46
<211> LENGTH: 100
<212> TYPE: PRT
<213> ORGANISM: Artificial Sequence
<220> FEATURE:
<223> OTHER INFORMATION: Synthetic

<400> SEQUENCE: 46

Ala Ser Gly Met Leu Ala Ile Ser Met Asp Thr Asp Lys Ile Ser Asn
1               5                   10                  15

Ser Phe Glu Asp Cys Lys Tyr Phe Gln Leu Glu Leu Pro Ser Ala Gly
            20                  25                  30

Trp Thr Asn Thr Ile Phe Asn Asp Glu Ser Gly Lys Glu Glu Ile Val
        35                  40                  45

Lys Met Asn Val Asp Ala Ile Ile Cys Lys Asn Ile Ser Glu Glu Asn
50                  55                  60

Tyr Lys Lys Phe Ser Lys Lys Ile Glu Ile Tyr His Ala Glu Gly Asp
65                  70                  75                  80

Asp Val Lys Lys Asn Ile Ser Leu Phe Leu Glu Gly Glu Leu Ser Lys
                85                  90                  95

Ile Ser Asn Pro
            100

<210> SEQ ID NO 47
<211> LENGTH: 100
<212> TYPE: PRT
<213> ORGANISM: Artificial Sequence
<220> FEATURE:
<223> OTHER INFORMATION: Synthetic

<400> SEQUENCE: 47

Ala Ser Gly Met Leu Ala Ile Ser Met Asp Thr Asp Lys Ile Ser Asn
1               5                   10                  15

Ser Phe Glu Asp Cys Lys Tyr Phe Gln Ile Glu Leu Pro Ser Ala Gly
            20                  25                  30

Gly Thr Asn Thr Ile Phe Asn Asp Glu Ser Gly Lys Glu Glu Ile Val
        35                  40                  45

Lys Met Gly Val Asp Ala Ile Ile Cys Lys Asn Ile Ser Glu Glu Asn
50                  55                  60

Tyr Lys Lys Phe Ser Lys Lys Ile Glu Ile Tyr His Ala Glu Gly Asp
65                  70                  75                  80

Asp Val Lys Lys Asn Ile Ser Leu Phe Ile Glu Gly Glu Leu Ser Lys
                85                  90                  95

Ile Ser Asn Pro
            100

<210> SEQ ID NO 48
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is any amino acid

<400> SEQUENCE: 48

```
Gly Xaa Cys Ile Gly Val Pro Ser Ala Gly Trp Glu Xaa Cys Trp
1               5                   10                  15
```

<210> SEQ ID NO 49
<211> LENGTH: 15
<212> TYPE: PRT
<213> ORGANISM: Artificial Sequence
<220> FEATURE:
<223> OTHER INFORMATION: Synthetic

<400> SEQUENCE: 49

```
Gly Gly Cys Ile Gly Val Pro Ser Ala Gly Trp Glu Trp Cys Pro
1               5                   10                  15
```

<210> SEQ ID NO 50
<211> LENGTH: 15
<212> TYPE: PRT
<213> ORGANISM: Artificial Sequence
<220> FEATURE:
<223> OTHER INFORMATION: Synthetic

<400> SEQUENCE: 50

```
Gly Gly Cys Leu Gly Val Pro Ser Ala Gly Trp Glu Ile Cys Trp
1               5                   10                  15
```

<210> SEQ ID NO 51
<211> LENGTH: 15
<212> TYPE: PRT
<213> ORGANISM: Artificial Sequence
<220> FEATURE:
<223> OTHER INFORMATION: Synthetic

<400> SEQUENCE: 51

```
Gly Trp Cys Ile Gly Val Pro Ser Ala Gly Trp Glu Ile Cys Trp
1               5                   10                  15
```

<210> SEQ ID NO 52
<211> LENGTH: 15
<212> TYPE: PRT
<213> ORGANISM: Artificial Sequence
<220> FEATURE:
<223> OTHER INFORMATION: Synthetic

<400> SEQUENCE: 52

```
Gly Arg Cys Ile Gly Val Pro Ser Ala Gly Trp Glu Val Cys Trp
1               5                   10                  15
```

<210> SEQ ID NO 53
<211> LENGTH: 15
<212> TYPE: PRT
<213> ORGANISM: Artificial Sequence
<220> FEATURE:
<223> OTHER INFORMATION: Synthetic

<400> SEQUENCE: 53

```
Gly His Cys Met Gly Val Ala Ser Ala Gly Trp Glu Ile Cys Trp
1               5                   10                  15
```

<210> SEQ ID NO 54
<211> LENGTH: 15
<212> TYPE: PRT
<213> ORGANISM: Artificial Sequence
<220> FEATURE:
<223> OTHER INFORMATION: Synthetic

<400> SEQUENCE: 54

```
Gly Asp Cys Ile Gly Val Ala Ser Ala Gly Trp Glu Trp Cys Pro
1               5                   10                  15
```

<210> SEQ ID NO 55
<211> LENGTH: 15
<212> TYPE: PRT
<213> ORGANISM: Artificial Sequence
<220> FEATURE:
<223> OTHER INFORMATION: Synthetic

<400> SEQUENCE: 55

```
Gly Gly Cys Ile Gly Val Pro Ser Ala Gly Trp Glu Trp Cys Pro
1               5                   10                  15
```

<210> SEQ ID NO 56
<211> LENGTH: 15
<212> TYPE: PRT
<213> ORGANISM: Artificial Sequence
<220> FEATURE:
<223> OTHER INFORMATION: Synthetic

<400> SEQUENCE: 56

```
Gly Gly Cys Leu Gly Val Pro Ser Ala Gly Trp Glu Trp Cys Pro
1               5                   10                  15
```

<210> SEQ ID NO 57
<211> LENGTH: 15
<212> TYPE: PRT
<213> ORGANISM: Artificial Sequence
<220> FEATURE:
<223> OTHER INFORMATION: Synthetic

<400> SEQUENCE: 57

```
Gly Trp Cys Ile Gly Val Pro Ser Ala Gly Trp Glu Ile Cys Trp
1               5                   10                  15
```

<210> SEQ ID NO 58
<211> LENGTH: 15
<212> TYPE: PRT
<213> ORGANISM: Artificial Sequence
<220> FEATURE:
<223> OTHER INFORMATION: Synthetic

<400> SEQUENCE: 58

```
Gly Trp Cys Ile Gly Val Pro Ser Ala Gly Trp Glu Ile Cys Trp
1               5                   10                  15
```

<210> SEQ ID NO 59
<211> LENGTH: 15
<212> TYPE: PRT
<213> ORGANISM: Artificial Sequence
<220> FEATURE:
<223> OTHER INFORMATION: Synthetic

<400> SEQUENCE: 59

```
Gly Arg Cys Ile Gly Val Pro Ser Ala Gly Trp Glu Val Cys Trp
1               5                   10                  15
```

<210> SEQ ID NO 60
<211> LENGTH: 15
<212> TYPE: PRT
<213> ORGANISM: Artificial Sequence
<220> FEATURE:
<223> OTHER INFORMATION: Synthetic

<400> SEQUENCE: 60

```
Gly His Cys Met Gly Val Ala Ser Ala Gly Trp Glu Ile Cys Trp
```

<210> SEQ ID NO 61
<211> LENGTH: 15
<212> TYPE: PRT
<213> ORGANISM: Artificial Sequence
<220> FEATURE:
<223> OTHER INFORMATION: Synthetic

<400> SEQUENCE: 61

Gly Asp Cys Ile Gly Val Ala Ser Ala Gly Trp Glu Trp Cys Pro
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Synthetic

<400> SEQUENCE: 62

Gly Tyr Cys Ile Gly Val Pro Ser Ala Gly Trp Glu Val Cys Trp
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Synthetic

<400> SEQUENCE: 63

Gly Tyr Cys Ile Gly Val Pro Ser Ala Gly Trp Glu Ile Cys Trp
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Synthetic

<400> SEQUENCE: 64

Gly Trp Cys Met Gly Val Pro Ser Ala Gly Trp Glu Ile Cys Trp
1               5                   10                  15

<210> SEQ ID NO 65
<211> LENGTH: 14
<212> TYPE: PRT
<213> ORGANISM: Artificial Sequence
<220> FEATURE:
<223> OTHER INFORMATION: Synthetic

<400> SEQUENCE: 65

Gly Ser Cys Tyr Arg Val Val Ser Ala Gly Trp Glu Thr Cys
1               5                   10

<210> SEQ ID NO 66
<211> LENGTH: 15
<212> TYPE: PRT
<213> ORGANISM: Artificial Sequence
<220> FEATURE:
<223> OTHER INFORMATION: Synthetic

<400> SEQUENCE: 66

Gly Asp Cys Ile Val Val Ala Ser Ala Gly Trp Glu Ala Cys Arg
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Synthetic

<400> SEQUENCE: 67

Gly Gly Cys Ala Arg Val Ala Ser Ala Gly Trp Glu Ile Cys Asn
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Synthetic

<400> SEQUENCE: 68

Gly Lys Cys Arg Trp Val Ala Ser Ala Gly Trp Glu Val Cys Ala
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Synthetic

<400> SEQUENCE: 69

Gly Asn Cys Phe Ala Val Val Ser Ala Gly Trp Glu Lys Cys Lys
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Synthetic

<400> SEQUENCE: 70

Gly Met Cys Thr His Val Leu Ser Ala Gly Trp Glu Pro Cys Leu
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Synthetic

<400> SEQUENCE: 71

Gly Met Cys Thr His Val Leu Ser Ala Gly Trp Glu Pro Cys Leu
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Synthetic

<400> SEQUENCE: 72

Gly Cys Cys Gly Tyr Val Ile Ser Ala Gly Trp Glu Met Cys Ser
1               5                   10                  15

```
<210> SEQ ID NO 73
<211> LENGTH: 15
<212> TYPE: PRT
<213> ORGANISM: Artificial Sequence
<220> FEATURE:
<223> OTHER INFORMATION: Synthetic

<400> SEQUENCE: 73

Gly Asp Cys Thr Cys Met Ile Ser Ala Gly Trp Glu Pro Cys Glu
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Synthetic

<400> SEQUENCE: 74

Gly Phe Cys Cys Leu Val Thr Ser Ala Gly Trp Glu Glu Cys Tyr
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Synthetic

<400> SEQUENCE: 75

Gly Phe Cys Cys Leu Val Thr Ser Ala Gly Trp Glu Glu Cys Tyr
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Synthetic

<400> SEQUENCE: 76

Gly Ser Cys Pro Phe Val Thr Ser Ala Gly Trp Glu Lys Cys Leu
1               5                   10                  15

<210> SEQ ID NO 77
<211> LENGTH: 17
<212> TYPE: PRT
<213> ORGANISM: Artificial Sequence
<220> FEATURE:
<223> OTHER INFORMATION: Synthetic

<400> SEQUENCE: 77

Gly Trp Cys Gly Arg Val Ile Ser Ala Gly Trp Glu Ala Trp Leu Ala
1               5                   10                  15

Arg

<210> SEQ ID NO 78
<211> LENGTH: 17
<212> TYPE: PRT
<213> ORGANISM: Artificial Sequence
<220> FEATURE:
<223> OTHER INFORMATION: Synthetic

<400> SEQUENCE: 78

Gly Asp Cys Ile Val Val Ala Ser Ala Gly Trp Glu Ala Cys Arg Leu
1               5                   10                  15
```

Glu

<210> SEQ ID NO 79
<211> LENGTH: 12
<212> TYPE: PRT
<213> ORGANISM: Artificial Sequence
<220> FEATURE:
<223> OTHER INFORMATION: Synthetic

<400> SEQUENCE: 79

```
Gly Thr Cys Arg Pro Val Leu Ser Ala Gly Trp Glu
1               5                   10
```

<210> SEQ ID NO 80
<211> LENGTH: 15
<212> TYPE: PRT
<213> ORGANISM: Artificial Sequence
<220> FEATURE:
<223> OTHER INFORMATION: Synthetic

<400> SEQUENCE: 80

```
Gly Arg Cys Ile Cys Ala Leu Ser Ala Gly Trp Glu Thr Cys Ala
1               5                   10                  15
```

<210> SEQ ID NO 81
<211> LENGTH: 15
<212> TYPE: PRT
<213> ORGANISM: Artificial Sequence
<220> FEATURE:
<223> OTHER INFORMATION: Synthetic

<400> SEQUENCE: 81

```
Gly Trp Cys Trp Gly Val Ile Ser Ala Gly Trp Glu Gly Cys Arg
1               5                   10                  15
```

<210> SEQ ID NO 82
<211> LENGTH: 15
<212> TYPE: PRT
<213> ORGANISM: Artificial Sequence
<220> FEATURE:
<223> OTHER INFORMATION: Synthetic

<400> SEQUENCE: 82

```
Gly Val Cys Val Lys Val Ala Ser Ala Gly Trp Glu Glu Cys Val
1               5                   10                  15
```

<210> SEQ ID NO 83
<211> LENGTH: 100
<212> TYPE: PRT
<213> ORGANISM: Artificial Sequence
<220> FEATURE:
<223> OTHER INFORMATION: Synthetic

<400> SEQUENCE: 83

```
Gly Ile Gly Met Val Ala Ile Ser Met Asp Thr Asp Lys Ile Ser Asn
1               5                   10                  15

Ser Phe Glu Asp Cys Lys Tyr Phe Leu Ile Val Val Ser Ala Gly
            20                  25                  30

Trp Thr Asn Thr Ile Phe Asn Asp Glu Ser Gly Lys Lys Glu Ile Val
        35                  40                  45

Lys Met Asn Val Asp Ala Ile Ile Cys Lys Asn Ile Ser Glu Glu Asn
    50                  55                  60

Tyr Lys Lys Phe Ser Lys Lys Ile Glu Ile Tyr His Ala Glu Gly Asp
65                  70                  75                  80
```

```
Asp Val Asp Lys Asn Ile Ser Leu Phe Ile Glu Gly Glu Leu Ser Lys
                85                  90                  95
Ile Ser Asn Pro
            100

<210> SEQ ID NO 84
<211> LENGTH: 87
<212> TYPE: PRT
<213> ORGANISM: Artificial Sequence
<220> FEATURE:
<223> OTHER INFORMATION: Synthetic

<400> SEQUENCE: 84

Gly Ile Val Asn Val Pro Asn Pro Asn Asn Thr Lys Phe Gln Gln Leu
1               5                   10                  15
Ala Arg Asn Ala Ile Ala Asn Tyr Asn Asp Asn Gln Asn Ala His Leu
            20                  25                  30
Glu Phe Val Glu Asn Leu Asn Val Lys Glu Gln Val Thr Gly Gly Ile
        35                  40                  45
Met Tyr Tyr Ile Thr Leu Ala Ala Thr Asp Asp Ala Gly Lys Lys Lys
    50                  55                  60
Ile Tyr Lys Ala Lys Ile Ala Val Val Asp Ser Ala Gly Trp Glu Gly
65                  70                  75                  80
Val Thr Glu Phe Lys Leu Val
                85

<210> SEQ ID NO 85
<211> LENGTH: 87
<212> TYPE: PRT
<213> ORGANISM: Artificial Sequence
<220> FEATURE:
<223> OTHER INFORMATION: Synthetic

<400> SEQUENCE: 85

Gly Ile Val Asn Val Pro Asn Pro Asn Asn Thr Lys Phe Gln Gln Leu
1               5                   10                  15
Ala Arg Asn Ala Ile Gln Asn Tyr Asn Asp Asn Gln Asn Ala His Leu
            20                  25                  30
Glu Phe Val Glu Asn Leu Asn Val Lys Glu Gln Val Thr Gly Gly Ile
        35                  40                  45
Met Tyr Tyr Ile Thr Leu Ala Ala Thr Asp Asp Ala Gly Lys Lys Lys
    50                  55                  60
Ile Tyr Lys Ala Lys Ile Ala Val Val Asp Ser Ala Gly Trp Glu Gly
65                  70                  75                  80
Ile Thr Glu Phe Lys Leu Val
                85

<210> SEQ ID NO 86
<211> LENGTH: 87
<212> TYPE: PRT
<213> ORGANISM: Artificial Sequence
<220> FEATURE:
<223> OTHER INFORMATION: Synthetic

<400> SEQUENCE: 86

Gly Ile Val Asn Val Pro Asn Pro Asn Asn Thr Lys Phe Gln Gln Leu
1               5                   10                  15
Ala Arg Ser Ala Ile Gln Asn Tyr Asn Asp Asn Gln Asn Ala His Leu
            20                  25                  30
```

```
Glu Phe Val Glu Asn Leu Asn Val Lys Glu Gln Val Thr Gly Gly Ile
             35                  40                  45

Met Tyr Tyr Ile Thr Leu Ala Ala Thr Asp Asp Ala Gly Lys Lys
 50                  55                  60

Ile Tyr Lys Ala Lys Ile Ala Val Val Asp Ser Ala Gly Trp Glu Gly
 65                  70                  75                  80

Ile Thr Glu Phe Lys Leu Val
                 85

<210> SEQ ID NO 87
<211> LENGTH: 179
<212> TYPE: PRT
<213> ORGANISM: Artificial Sequence
<220> FEATURE:
<223> OTHER INFORMATION: Synthetic

<400> SEQUENCE: 87

Lys Glu Ile Thr Asn Ala Leu Glu Thr Trp Gly Ala Leu Gly Gln Asp
 1               5                  10                  15

Ile Asn Leu Asp Ile Pro Ser Phe Gln Met Ser Asp Asp Ile Ala Asp
                 20                  25                  30

Ile Lys Trp Glu Lys Thr Gln Asp Asn Lys Met Ile Val Val Phe Ser
             35                  40                  45

Ala Gly Trp Ile Ala Lys Asp Thr Tyr Asp Leu Tyr Glu Asn Gly Thr
 50                  55                  60

Leu Lys Ile Ala His Leu Thr Thr Asp Asp Gln Ala Ile Tyr Lys Val
 65                  70                  75                  80

Ser Ile Thr Asp Thr Lys Gly Lys Asn Val Leu Glu Lys Ile Phe Asp
                 85                  90                  95

Leu Lys Ile Gln Glu Arg Val Ser Lys Pro Lys Ile Ser Trp Thr Cys
                100                 105                 110

Ile Asn Thr Thr Leu Thr Cys Glu Val Met Asn Gly Thr Asp Pro Glu
             115                 120                 125

Leu Asn Leu Tyr Gln Asp Gly Lys His Leu Lys Leu Ser Gln Arg Val
 130                 135                 140

Ile Thr His Lys Trp Thr Thr Ser Leu Ser Ala Lys Phe Lys Cys Thr
145                 150                 155                 160

Ala Gly Asn Lys Val Ser Lys Glu Ser Ser Val Glu Pro Val Ser Cys
                165                 170                 175

Pro Glu Lys

<210> SEQ ID NO 88
<211> LENGTH: 167
<212> TYPE: PRT
<213> ORGANISM: Artificial Sequence
<220> FEATURE:
<223> OTHER INFORMATION: Synthetic

<400> SEQUENCE: 88

Lys Ile Ile Ile Thr Gly Glu Pro Gly Val Gly Lys Thr Thr Leu Val
 1               5                  10                  15

Lys Lys Ile Val Glu Arg Leu Gly Lys Arg Ala Ile Gly Phe Trp Thr
                 20                  25                  30

Glu Glu Val Thr Asp Pro Glu Thr Lys Lys Arg Thr Gly Phe Arg Ile
             35                  40                  45

Ile Thr Thr Glu Gly Lys Lys Val Phe Ser Val Val Ser Ala Gly
 50                  55                  60
```

```
Trp Glu Ser Lys Gln Asn Phe Glu Glu Leu Ala Ile Pro Ile Leu Glu
 65                  70                  75                  80

Arg Ala Tyr Arg Glu Ala Lys Lys Asp Arg Arg Lys Val Ile Ile Ile
                 85                  90                  95

Asp Glu Ile Gly Asp Ala Leu Gly Ser Ser Lys Phe Arg Asp Leu Val
            100                 105                 110

Arg Gln Ile His Asp Pro Asn Val Asn Val Val Ala Thr Ile Pro Ile
        115                 120                 125

Arg Asp Asp Ala Pro Leu Ile Lys Glu Ile Arg Arg Leu Pro Gly Ala
    130                 135                 140

Val Leu Ile Glu Leu Thr Pro Glu Asn Arg Asp Val Ile Leu Glu Asp
145                 150                 155                 160

Ile Leu Ser Leu Leu Glu Arg
                165

<210> SEQ ID NO 89
<211> LENGTH: 121
<212> TYPE: PRT
<213> ORGANISM: Artificial Sequence
<220> FEATURE:
<223> OTHER INFORMATION: Synthetic

<400> SEQUENCE: 89

Gly His Pro Thr Leu Lys Thr Pro Glu Ser Val Thr Gly Thr Trp Lys
  1               5                  10                  15

Gly Asp Val Lys Ile Gln Cys Ile Tyr Asp Pro Leu Arg Gly Tyr Glu
                 20                  25                  30

Gln Thr Glu Val Lys Trp Leu Val Arg His Gly Ser Asp Ser Val Thr
             35                  40                  45

Ile Phe Glu Arg Val Ser Ser Ala Gly Trp Asp Gly Ile Ser Gln Asp
    50                  55                  60

Lys Tyr Asn Gly Arg Leu Gln Val Ser Asp Ser Val Pro Gly Asp Val
 65                  70                  75                  80

Ser Leu Gln Ile Asn Thr Leu Gln Met Asp Asp Arg Asn His Tyr Thr
                 85                  90                  95

Cys Glu Val Thr Trp Gln Thr Pro Asp Gly Asn Gln Val Ile Arg Asp
            100                 105                 110

Lys Ile Ile Glu Leu Arg Val Arg Lys
        115                 120

<210> SEQ ID NO 90
<211> LENGTH: 100
<212> TYPE: PRT
<213> ORGANISM: Artificial Sequence
<220> FEATURE:
<223> OTHER INFORMATION: Synthetic

<400> SEQUENCE: 90

Gly Ile Gly Met Val Ala Ile Ser Met Asp Thr Asp Lys Ile Ser Asn
  1               5                  10                  15

Ser Phe Glu Asp Cys Lys Tyr Phe Leu Ile Met Val Val Ser Ala Gly
                 20                  25                  30

Trp Thr Asn Thr Ile Ser Asn Asp Glu Ser Gly Lys Lys Glu Ile Val
             35                  40                  45

Glu Met Asn Val Asp Ala Ile Ile Cys Lys Asn Ile Ser Glu Glu Asn
    50                  55                  60

Tyr Lys Lys Phe Ser Lys Lys Ile Glu Ile Tyr His Ala Glu Gly Asp
 65                  70                  75                  80
```

```
Asp Val Asp Lys Asn Ile Ser Leu Phe Ile Glu Gly Glu Leu Ser Lys
                85                  90                  95

Ile Ser Asn Pro
            100

<210> SEQ ID NO 91
<211> LENGTH: 100
<212> TYPE: PRT
<213> ORGANISM: Artificial Sequence
<220> FEATURE:
<223> OTHER INFORMATION: Synthetic

<400> SEQUENCE: 91

Gly Thr Gly Met Val Ala Ile Ser Met Asp Thr Asp Lys Ile Ser Asn
1               5                   10                  15

Ser Phe Glu Asp Cys Lys Tyr Phe Leu Ile Val Val Glu Ser Ala Gly
                20                  25                  30

Trp Thr Asn Thr Ile Phe Asn Asp Glu Ser Gly Lys Lys Glu Ile Val
            35                  40                  45

Lys Met Asn Val Asp Ala Ile Ile Cys Lys Asn Ile Ser Glu Glu Asn
        50                  55                  60

Tyr Lys Lys Phe Ser Lys Lys Ile Glu Ile Tyr His Ala Glu Gly Asp
65                  70                  75                  80

Asp Val Asp Lys Asn Ile Ser Leu Phe Ile Glu Gly Glu Leu Ser Lys
                85                  90                  95

Ile Ser Asn Pro
            100

<210> SEQ ID NO 92
<211> LENGTH: 102
<212> TYPE: PRT
<213> ORGANISM: Artificial Sequence
<220> FEATURE:
<223> OTHER INFORMATION: Synthetic

<400> SEQUENCE: 92

Gly Thr Gly Met Val Ala Ile Ser Met Asp Thr Asp Lys Ile Ser Asn
1               5                   10                  15

Ser Phe Glu Asp Cys Lys Tyr Phe Leu Ile Val Met Val Ser Ala Gly
                20                  25                  30

Trp Thr Asn Thr Ile Phe Asn Asp Glu Ser Gly Lys Lys Glu Ile Val
            35                  40                  45

Lys Met Asn Val Asp Ala Ile Ile Cys Lys Asn Ile Ser Glu Glu Asn
        50                  55                  60

Tyr Lys Lys Phe Ser Lys Lys Ile Glu Ile Tyr His Ala Glu Gly Asp
65                  70                  75                  80

Asp Val Asp Lys Asn Ile Ser Leu Phe Ile Glu Gly Glu Leu Ser Lys
                85                  90                  95

Ile Ser Asn Pro Leu Glu
            100

<210> SEQ ID NO 93
<211> LENGTH: 102
<212> TYPE: PRT
<213> ORGANISM: Artificial Sequence
<220> FEATURE:
<223> OTHER INFORMATION: Synthetic

<400> SEQUENCE: 93
```

Gly Thr Gly Met Val Ala Ile Ser Met Asp Thr Asp Lys Ile Ser Asn
1               5                   10                  15

Ser Phe Glu Asp Cys Lys Tyr Phe Leu Ile Met Val Ser Ala Gly
            20                  25                  30

Trp Thr Asn Thr Ile Phe Asn Asp Glu Ser Gly Lys Lys Glu Ile Val
        35                  40                  45

Glu Met Asn Val Asp Ala Ile Ile Cys Lys Asn Ile Ser Glu Glu Asn
    50                  55                  60

Tyr Lys Lys Phe Ser Lys Ile Glu Ile Tyr His Ala Glu Gly Asp
65                  70                  75                  80

Asp Val Asp Lys Asn Ile Ser Leu Phe Ile Glu Gly Glu Leu Ser Lys
                85                  90                  95

Ile Ser Asn Pro Leu Glu
            100

<210> SEQ ID NO 94
<211> LENGTH: 87
<212> TYPE: PRT
<213> ORGANISM: Artificial Sequence
<220> FEATURE:
<223> OTHER INFORMATION: Synthetic

<400> SEQUENCE: 94

Gly Ile Val Asn Val Pro Asn Pro Asn Thr Lys Phe Gln Gln Leu
1               5                   10                  15

Ala Arg Asn Ala Ile Ala Asn Tyr Asn Asp Tyr Gln Asn Ala His Leu
            20                  25                  30

Glu Phe Val Glu Asn Leu Asn Val Lys Glu Gln Val Thr Gly Asp Ile
        35                  40                  45

Met Tyr Tyr Ile Thr Leu Ala Ala Thr Asp Asp Ala Gly Lys Lys Lys
    50                  55                  60

Ile Tyr Lys Ala Lys Ile Ala Val Val Asp Ser Ala Gly Trp Glu Gly
65                  70                  75                  80

Val Thr Glu Phe Lys Leu Val
            85

<210> SEQ ID NO 95
<211> LENGTH: 88
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 95

Gly Ile Val Asn Val Pro Asn Xaa Asn Thr Thr Lys Tyr Gln Gln Leu
1               5                   10                  15

Ala Arg Ile Ala Ile Ala Val Tyr Asn His His Gln Asn Ala His Leu
            20                  25                  30

Glu Phe Val Glu Asn Leu Asn Xaa Val Lys Glu Gln Leu Gly Glu Gly
        35                  40                  45

Asp Met Tyr Tyr Ile Thr Leu Ala Ala Thr Asp Ala Gly Lys Lys
    50                  55                  60

```
Lys Ile Tyr Lys Ala Lys Val Gly Val Val Glu Ser Ala Gly Trp Thr
 65                  70                  75                  80

Gly Val Glu Glu Phe Lys Leu Val
                 85
```

<210> SEQ ID NO 96
<211> LENGTH: 88
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 96

```
Gly Ile Val Asn Val Pro Asn Xaa Asn Thr Thr Lys Tyr Gln Gln Leu
 1               5                  10                  15

Ala Arg Ser Ala Ile Ala Ile Tyr Asn Tyr His Gln Asn Ala His Leu
             20                  25                  30

Glu Phe Val Glu Asn Leu Asn Xaa Val Lys Glu Gln Leu Gly Glu Gly
         35                  40                  45

Asp Met Tyr Tyr Ile Thr Leu Ala Ala Thr Asp Asp Ala Gly Lys Lys
     50                  55                  60

Lys Ile Tyr Lys Ala Lys Ile Gly Val Val Glu Ser Ala Gly Trp Thr
 65                  70                  75                  80

Gly Val Glu Glu Phe Lys Leu Val
                 85
```

<210> SEQ ID NO 97
<211> LENGTH: 88
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 97

```
Gly Ile Val Asn Val Pro Asn Xaa Asn Thr Thr Lys Tyr Gln Gln Leu
 1               5                  10                  15

Ala Arg Ser Ala Ile Ala Ile Tyr Asn Tyr His Gln Asn Ala His Leu
             20                  25                  30

Glu Phe Val Glu Asn Leu Asn Xaa Val Lys Gln Ile Gly Glu Gly
         35                  40                  45

Ser Met Tyr Tyr Ile Thr Leu Ala Ala Thr Asp Asp Ala Gly Lys Lys
     50                  55                  60

Lys Ile Tyr Lys Ala Lys Val Gly Val Val Glu Ser Ala Gly Trp Glu
 65                  70                  75                  80

Gly Val Glu Glu Phe Lys Leu Val
                 85
```

```
<210> SEQ ID NO 98
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(5)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is P, A, T, I or L
<220> FEATURE:
<221> NAME/KEY: MISC_FEATURE
<222> LOCATION: (13)..(13)
<223> OTHER INFORMATION: Xaa is any amino acid
<220> FEATURE:
<221> NAME/KEY: MISC_FEATURE
<222> LOCATION: (15)..(15)
<223> OTHER INFORMATION: Xaa is any amino acid

<400> SEQUENCE: 98

Gly Xaa Cys Xaa Xaa Val Xaa Ser Ala Gly Trp Glu Xaa Cys Xaa
1               5                   10                  15

<210> SEQ ID NO 99
<211> LENGTH: 15
<212> TYPE: PRT
<213> ORGANISM: Artificial Sequence
<220> FEATURE:
<223> OTHER INFORMATION: Synthetic

<400> SEQUENCE: 99

Met Ser Met Gln Gln Val Val Ser Ala Gly Trp Glu Arg Ala Asp
1               5                   10                  15

<210> SEQ ID NO 100
<211> LENGTH: 13
<212> TYPE: PRT
<213> ORGANISM: Artificial Sequence
<220> FEATURE:
<223> OTHER INFORMATION: Synthetic

<400> SEQUENCE: 100

Met Gln Gln Val Val Ser Ala Gly Trp Glu Arg Ala Asp
1               5                   10

<210> SEQ ID NO 101
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is G, W, R, H, Y, E, Q, C, or D
<220> FEATURE:
<221> NAME/KEY: MISC_FEATURE
<222> LOCATION: (15)..(15)
<223> OTHER INFORMATION: Xaa is W, I, V, R, M, G, L, or V

<400> SEQUENCE: 101

His Met Gly Xaa Cys Ile Gly Val Pro Ser Ala Gly Trp Glu Xaa Cys
1               5                   10                  15
```

Trp Leu Glu

<210> SEQ ID NO 102
<211> LENGTH: 19
<212> TYPE: PRT
<213> ORGANISM: Artificial Sequence
<220> FEATURE:
<223> OTHER INFORMATION: Synthetic

<400> SEQUENCE: 102

His Met Gly Gly Cys Ile Gly Val Pro Ser Ala Gly Trp Glu Trp Cys
1               5                   10                  15

Pro Leu Glu

<210> SEQ ID NO 103
<211> LENGTH: 19
<212> TYPE: PRT
<213> ORGANISM: Artificial Sequence
<220> FEATURE:
<223> OTHER INFORMATION: Synthetic

<400> SEQUENCE: 103

His Met Gly Trp Cys Ile Gly Val Pro Ser Ala Gly Trp Glu Ile Cys
1               5                   10                  15

Trp Leu Glu

<210> SEQ ID NO 104
<211> LENGTH: 19
<212> TYPE: PRT
<213> ORGANISM: Artificial Sequence
<220> FEATURE:
<223> OTHER INFORMATION: Synthetic

<400> SEQUENCE: 104

His Met Gly Arg Cys Ile Gly Val Pro Ser Ala Gly Trp Glu Val Cys
1               5                   10                  15

Trp Leu Glu

<210> SEQ ID NO 105
<211> LENGTH: 19
<212> TYPE: PRT
<213> ORGANISM: Artificial Sequence
<220> FEATURE:
<223> OTHER INFORMATION: Synthetic

<400> SEQUENCE: 105

His Met Gly His Cys Met Gly Val Ala Ser Ala Gly Trp Glu Ile Cys
1               5                   10                  15

Trp Leu Glu

<210> SEQ ID NO 106
<211> LENGTH: 19
<212> TYPE: PRT
<213> ORGANISM: Artificial Sequence
<220> FEATURE:
<223> OTHER INFORMATION: Synthetic

<400> SEQUENCE: 106

His Met Gly Asp Cys Ile Gly Val Ala Ser Ala Gly Trp Glu Trp Cys
1               5                   10                  15

Pro Leu Glu

<210> SEQ ID NO 107

```
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is G or M
<220> FEATURE:
<221> NAME/KEY: MISC_FEATURE
<222> LOCATION: (10)..(10)
<223> OTHER INFORMATION: Xaa is T or N
<220> FEATURE:
<221> NAME/KEY: MISC_FEATURE
<222> LOCATION: (13)..(13)
<223> OTHER INFORMATION: Xaa is F or Y
<220> FEATURE:
<221> NAME/KEY: MISC_FEATURE
<222> LOCATION: (19)..(19)
<223> OTHER INFORMATION: Xaa is S, R or N
<220> FEATURE:
<221> NAME/KEY: MISC_FEATURE
<222> LOCATION: (23)..(23)
<223> OTHER INFORMATION: Xaa is I, V or N
<220> FEATURE:
<221> NAME/KEY: MISC_FEATURE
<222> LOCATION: (26)..(26)
<223> OTHER INFORMATION: Xaa is Y, H, N or Q
<220> FEATURE:
<221> NAME/KEY: MISC_FEATURE
<222> LOCATION: (27)..(27)
<223> OTHER INFORMATION: Xaa is Y, H, or N
<220> FEATURE:
<221> NAME/KEY: MISC_FEATURE
<222> LOCATION: (44)..(44)
<223> OTHER INFORMATION: Xaa is V, L, or I
<220> FEATURE:
<221> NAME/KEY: MISC_FEATURE
<222> LOCATION: (45)..(45)
<223> OTHER INFORMATION: Xaa is T, S, D, or G
<220> FEATURE:
<221> NAME/KEY: MISC_FEATURE
<222> LOCATION: (46)..(46)
<223> OTHER INFORMATION: Xaa is G, Y, F or A
<220> FEATURE:
<221> NAME/KEY: MISC_FEATURE
<222> LOCATION: (48)..(48)
<223> OTHER INFORMATION: Xaa is I, D, S, N or A
<220> FEATURE:
<221> NAME/KEY: MISC_FEATURE
<222> LOCATION: (70)..(70)
<223> OTHER INFORMATION: Xaa is I or V
<220> FEATURE:
<221> NAME/KEY: MISC_FEATURE
<222> LOCATION: (71)..(71)
<223> OTHER INFORMATION: Xaa is G or A
<220> FEATURE:
<221> NAME/KEY: MISC_FEATURE
<222> LOCATION: (74)..(74)
<223> OTHER INFORMATION: Xaa is D or E
<220> FEATURE:
<221> NAME/KEY: MISC_FEATURE
<222> LOCATION: (79)..(79)
<223> OTHER INFORMATION: Xaa is F, V, I, or K
<220> FEATURE:
<221> NAME/KEY: MISC_FEATURE
<222> LOCATION: (82)..(82)
<223> OTHER INFORMATION: Xaa is E or T

<400> SEQUENCE: 107

Xaa Ile Val Asn Val Pro Asn Pro Asn Xaa Thr Lys Xaa Gln Gln Leu
1               5                   10                  15

Ala Arg Xaa Ala Ile Ala Xaa Tyr Asn Xaa Xaa Gln Asn Ala His Leu
            20                  25                  30

Glu Phe Val Glu Asn Leu Asn Val Lys Glu Gln Xaa Xaa Xaa Gly Xaa
```

```
                35                  40                  45

Met Tyr Tyr Ile Thr Leu Ala Ala Thr Asp Asp Ala Gly Lys Lys Lys
    50                  55                  60

Ile Tyr Lys Ala Lys Xaa Xaa Val Val Xaa Ser Ala Gly Trp Xaa Gly
65                  70                  75                  80

Val Xaa Glu Phe Lys Leu Val
                85

<210> SEQ ID NO 108
<211> LENGTH: 87
<212> TYPE: PRT
<213> ORGANISM: Artificial Sequence
<220> FEATURE:
<223> OTHER INFORMATION: Synthetic

<400> SEQUENCE: 108

Gly Ile Val Asn Val Pro Asn Pro Asn Asn Thr Lys Phe Gln Gln Leu
1               5                   10                  15

Ala Arg Asn Ala Ile Ala Asn Tyr Asn Gln Asn Gln Asn Ala His Leu
                20                  25                  30

Glu Phe Val Glu Asn Leu Asn Val Lys Glu Gln Val Thr Gly Gly Ile
            35                  40                  45

Met Tyr Tyr Ile Thr Leu Ala Ala Thr Asp Asp Ala Gly Lys Lys Lys
    50                  55                  60

Ile Tyr Lys Ala Lys Ile Ala Val Val Asp Ser Ala Gly Trp Phe Gly
65                  70                  75                  80

Val Thr Glu Phe Lys Leu Val
                85

<210> SEQ ID NO 109
<211> LENGTH: 87
<212> TYPE: PRT
<213> ORGANISM: Artificial Sequence
<220> FEATURE:
<223> OTHER INFORMATION: Synthetic

<400> SEQUENCE: 109

Gly Ile Val Asn Val Pro Asn Pro Asn Thr Thr Lys Tyr Gln Gln Leu
1               5                   10                  15

Ala Arg Ser Ala Ile Ala Ile Tyr Asn Tyr His Gln Asn Ala His Leu
                20                  25                  30

Glu Phe Val Glu Asn Leu Asn Val Lys Glu Gln Ile Ser Tyr Gly Asp
            35                  40                  45

Met Tyr Tyr Ile Thr Leu Ala Ala Thr Asp Asp Ala Gly Lys Lys Lys
    50                  55                  60

Ile Tyr Lys Ala Lys Ile Gly Val Val Glu Ser Ala Gly Trp Val Gly
65                  70                  75                  80

Val Glu Glu Phe Lys Leu Val
                85

<210> SEQ ID NO 110
<211> LENGTH: 87
<212> TYPE: PRT
<213> ORGANISM: Artificial Sequence
<220> FEATURE:
<223> OTHER INFORMATION: Synthetic

<400> SEQUENCE: 110

Gly Ile Val Asn Val Pro Asn Pro Asn Thr Thr Lys Tyr Gln Gln Leu
1               5                   10                  15
```

Ala Arg Ser Ala Ile Ala Ile Tyr Asn Tyr His Gln Asn Ala His Leu
            20                  25                  30

Glu Phe Val Glu Asn Leu Asn Val Lys Glu Gln Ile Ser Tyr Gly Asp
        35                  40                  45

Met Tyr Tyr Ile Thr Leu Ala Ala Thr Asp Asp Ala Gly Lys Lys Lys
 50                  55                  60

Ile Tyr Lys Ala Lys Ile Gly Val Val Glu Ser Ala Gly Trp Val Gly
 65                  70                  75                  80

Val Glu Glu Phe Lys Leu Val
                85

<210> SEQ ID NO 111
<211> LENGTH: 87
<212> TYPE: PRT
<213> ORGANISM: Artificial Sequence
<220> FEATURE:
<223> OTHER INFORMATION: Synthetic

<400> SEQUENCE: 111

Gly Ile Val Asn Val Pro Asn Pro Asn Thr Thr Lys Tyr Gln Gln Leu
1               5                   10                  15

Ala Arg Arg Ala Ile Ala Val Tyr Asn Tyr Gln Asn Ala His Leu
            20                  25                  30

Glu Phe Val Glu Asn Leu Asn Val Lys Glu Gln Ile Ser Tyr Gly Ser
        35                  40                  45

Met Tyr Tyr Ile Thr Leu Ala Ala Thr Asp Asp Ala Gly Lys Lys Lys
 50                  55                  60

Ile Tyr Lys Ala Lys Ile Gly Val Val Glu Ser Ala Gly Trp Val Gly
 65                  70                  75                  80

Val Glu Glu Phe Lys Leu Val
                85

<210> SEQ ID NO 112
<211> LENGTH: 87
<212> TYPE: PRT
<213> ORGANISM: Artificial Sequence
<220> FEATURE:
<223> OTHER INFORMATION: Synthetic

<400> SEQUENCE: 112

Gly Ile Val Asn Val Pro Asn Pro Asn Thr Thr Lys Tyr Gln Gln Leu
1               5                   10                  15

Ala Arg Ser Ala Ile Ala Ile Tyr Asn Asn His Gln Asn Ala His Leu
            20                  25                  30

Glu Phe Val Glu Asn Leu Asn Val Lys Glu Gln Val Ser Tyr Gly Ala
        35                  40                  45

Met Tyr Tyr Ile Thr Leu Ala Ala Thr Asp Asp Ala Gly Lys Lys Lys
 50                  55                  60

Ile Tyr Lys Ala Lys Val Gly Val Val Glu Ser Ala Gly Trp Val Gly
 65                  70                  75                  80

Val Glu Glu Phe Lys Leu Val
                85

<210> SEQ ID NO 113
<211> LENGTH: 87
<212> TYPE: PRT
<213> ORGANISM: Artificial Sequence
<220> FEATURE:
<223> OTHER INFORMATION: Synthetic

<400> SEQUENCE: 113

Gly Ile Val Asn Val Pro Asn Pro Asn Thr Thr Lys Tyr Gln Gln Leu
1               5                   10                  15

Ala Arg Ser Ala Ile Ala Val Tyr Asn Tyr His Gln Asn Ala His Leu
            20                  25                  30

Glu Phe Val Glu Asn Leu Asn Val Lys Glu Gln Ile Asp Tyr Gly Ala
        35                  40                  45

Met Tyr Tyr Ile Thr Leu Ala Ala Thr Asp Asp Ala Gly Lys Lys Lys
    50                  55                  60

Ile Tyr Lys Ala Lys Ile Gly Val Val Glu Ser Ala Gly Trp Ile Gly
65                  70                  75                  80

Val Glu Glu Phe Lys Leu Val
                85

<210> SEQ ID NO 114
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (48)..(48)
<223> OTHER INFORMATION: Xaa can be any naturally occurring amino acid

<400> SEQUENCE: 114

Met Ile Val Asn Val Pro Asn Pro Asn Thr Thr Lys Tyr Gln Gln Leu
1               5                   10                  15

Ala Arg Ser Ala Ile Ala Val Tyr Asn His His Gln Asn Ala His Leu
            20                  25                  30

Glu Phe Val Glu Asn Leu Asn Val Lys Glu Gln Ile Gly Tyr Gly Xaa
        35                  40                  45

Met Tyr Tyr Ile Thr Leu Ala Ala Thr Asp Asp Ala Gly Lys Lys Lys
    50                  55                  60

Ile Tyr Lys Ala Lys Ile Gly Val Val Glu Ser Ala Gly Trp Val Gly
65                  70                  75                  80

Val Glu Glu Phe Lys Leu Val
                85

<210> SEQ ID NO 115
<211> LENGTH: 87
<212> TYPE: PRT
<213> ORGANISM: Artificial Sequence
<220> FEATURE:
<223> OTHER INFORMATION: Synthetic

<400> SEQUENCE: 115

Gly Ile Val Asn Val Pro Asn Pro Asn Thr Thr Lys Tyr Gln Gln Leu
1               5                   10                  15

Ala Arg Ser Ala Ile Ala Ile Tyr Asn Tyr His Gln Asn Ala His Leu
            20                  25                  30

Glu Phe Val Glu Asn Leu Asn Val Lys Glu Gln Ile Gly Phe Gly Asn
        35                  40                  45

Met Tyr Tyr Ile Thr Leu Ala Ala Thr Asp Asp Ala Gly Lys Lys Lys
    50                  55                  60

Ile Tyr Lys Ala Lys Val Gly Val Val Glu Ser Ala Gly Trp Ile Gly
65                  70                  75                  80

Val Glu Glu Phe Lys Leu Val

<210> SEQ ID NO 116
<211> LENGTH: 87
<212> TYPE: PRT
<213> ORGANISM: Artificial Sequence
<220> FEATURE:
<223> OTHER INFORMATION: Synthetic

<400> SEQUENCE: 116

```
Gly Ile Val Asn Val Pro Asn Pro Asn Thr Thr Lys Tyr Gln Gln Leu
1               5                   10                  15

Ala Arg Ser Ala Ile Ala Val Tyr Asn His Tyr Gln Asn Ala His Leu
            20                  25                  30

Glu Phe Val Glu Asn Leu Asn Val Lys Glu Gln Ile Thr Ala Gly Asn
        35                  40                  45

Met Tyr Tyr Ile Thr Leu Ala Ala Thr Asp Asp Ala Gly Lys Lys Lys
    50                  55                  60

Ile Tyr Lys Ala Lys Ile Gly Val Glu Ser Ala Gly Trp Lys Gly
65                  70                  75                  80

Val Glu Glu Phe Lys Leu Val
                85
```

<210> SEQ ID NO 117
<211> LENGTH: 87
<212> TYPE: PRT
<213> ORGANISM: Artificial Sequence
<220> FEATURE:
<223> OTHER INFORMATION: Synthetic

<400> SEQUENCE: 117

```
Gly Ile Val Asn Val Pro Asn Pro Asn Asn Thr Lys Phe Gln Gln Leu
1               5                   10                  15

Ala Arg Ser Ala Ile Ala Asn Tyr Asn Asp Tyr Gln Asn Ala His Leu
            20                  25                  30

Glu Phe Val Glu Asn Leu Asn Val Lys Glu Gln Val Thr Gly Asp Ile
        35                  40                  45

Met Tyr Tyr Ile Thr Leu Ala Ala Thr Asp Asp Ala Gly Lys Lys Lys
    50                  55                  60

Ile Tyr Lys Ala Lys Ile Ala Val Val Asp Ser Ala Gly Trp Glu Gly
65                  70                  75                  80

Val Thr Glu Phe Lys Leu Val
                85
```

<210> SEQ ID NO 118
<211> LENGTH: 87
<212> TYPE: PRT
<213> ORGANISM: Artificial Sequence
<220> FEATURE:
<223> OTHER INFORMATION: Synthetic

<400> SEQUENCE: 118

```
Gly Ile Val Asn Val Pro Asn Pro Asn Asn Thr Lys Phe Gln Gln Leu
1               5                   10                  15

Ala Arg Tyr Ala Ile Ala Asn Tyr Asn Asp Tyr Gln Asn Ala His Leu
            20                  25                  30

Glu Phe Val Glu Asn Leu Asn Val Lys Glu Gln Val Thr Gly Asp Ile
        35                  40                  45

Met Tyr Tyr Ile Thr Leu Ala Ala Thr Asp Asp Ala Gly Lys Lys Lys
    50                  55                  60
```

```
Ile Tyr Lys Ala Lys Ile Ala Val Val Asp Ser Ala Gly Trp Glu Gly
 65                  70                  75                  80

Val Thr Glu Phe Lys Leu Val
                 85

<210> SEQ ID NO 119
<211> LENGTH: 87
<212> TYPE: PRT
<213> ORGANISM: Artificial Sequence
<220> FEATURE:
<223> OTHER INFORMATION: Synthetic

<400> SEQUENCE: 119

Gly Ile Val Asn Val Pro Asn Pro Asn Asn Thr Lys Phe Gln Gln Leu
 1               5                  10                  15

Ala Arg Asn Ala Ile Ala Asn Tyr Asn Asp Tyr Gln Asn Ala His Leu
                 20                  25                  30

Glu Phe Val Glu Asn Met Asn Val Lys Glu Gln Val Thr Gly Asp Ile
             35                  40                  45

Met Tyr Tyr Ile Thr Leu Ala Ala Thr Asp Asp Ala Gly Lys Lys Lys
     50                  55                  60

Ile Tyr Lys Ala Lys Ile Ala Val Val Asp Ser Ala Gly Trp Glu Gly
 65                  70                  75                  80

Val Thr Glu Phe Lys Leu Val
                 85

<210> SEQ ID NO 120
<211> LENGTH: 87
<212> TYPE: PRT
<213> ORGANISM: Artificial Sequence
<220> FEATURE:
<223> OTHER INFORMATION: Synthetic

<400> SEQUENCE: 120

Gly Ile Val Asn Val Pro Asn Pro Asn Asn Thr Lys Phe Gln Gln Leu
 1               5                  10                  15

Ala Arg Asn Ala Ile Ala Asn Tyr Asn Asp Tyr Gln Asn Ala His Leu
                 20                  25                  30

Glu Phe Val Glu Asn Leu Asn Val Lys Glu Gln Val Thr Asp Asp Ile
             35                  40                  45

Met Tyr Tyr Ile Thr Leu Ala Ala Thr Asp Asp Ala Gly Lys Lys Lys
     50                  55                  60

Ile Tyr Lys Ala Lys Ile Ala Val Val Asp Ser Ala Gly Trp Glu Gly
 65                  70                  75                  80

Val Thr Glu Phe Lys Leu Val
                 85

<210> SEQ ID NO 121
<211> LENGTH: 87
<212> TYPE: PRT
<213> ORGANISM: Artificial Sequence
<220> FEATURE:
<223> OTHER INFORMATION: Synthetic

<400> SEQUENCE: 121

Gly Ile Val Asn Val Pro Asn Pro Asn Asn Thr Lys Phe Gln Gln Leu
 1               5                  10                  15

Ala Arg Ser Ala Ile Ala Asn Tyr Asn Asp Tyr Gln Asn Ala His Leu
                 20                  25                  30
```

```
Glu Phe Val Glu Asn Leu Asn Val Lys Glu Gln Val Thr Gly Asp Ile
            35                  40                  45

Met Tyr Tyr Ile Thr Leu Ala Ala Thr Asp Asp Ala Gly Lys Lys Lys
 50                  55                  60

Ile Tyr Lys Ala Lys Ile Ala Val Val Asp Ser Ala Gly Trp Glu Gly
 65                  70                  75                  80

Val Thr Glu Phe Lys Leu Val
                85

<210> SEQ ID NO 122
<211> LENGTH: 87
<212> TYPE: PRT
<213> ORGANISM: Artificial Sequence
<220> FEATURE:
<223> OTHER INFORMATION: Synthetic

<400> SEQUENCE: 122

Gly Ile Val Asn Val Pro Asn Pro Asn Asn Thr Lys Phe Gln Gln Leu
 1               5                  10                  15

Ala Arg Tyr Ala Ile Ala Asn Tyr Asn Asp Tyr Gln Asn Ala His Leu
                20                  25                  30

Glu Phe Val Glu Asn Leu Asn Val Lys Glu Gln Val Thr Gly Asp Ile
            35                  40                  45

Met Tyr Tyr Ile Thr Leu Ala Ala Thr Asp Asp Ala Gly Lys Lys Lys
 50                  55                  60

Ile Tyr Lys Ala Lys Ile Ala Val Val Asp Ser Ala Gly Trp Glu Gly
 65                  70                  75                  80

Val Thr Glu Phe Lys Leu Val
                85

<210> SEQ ID NO 123
<211> LENGTH: 87
<212> TYPE: PRT
<213> ORGANISM: Artificial Sequence
<220> FEATURE:
<223> OTHER INFORMATION: Synthetic

<400> SEQUENCE: 123

Gly Ile Val Asn Val Pro Asn Pro Asn Asn Thr Lys Phe Gln Gln Leu
 1               5                  10                  15

Ala Arg Asn Ala Ile Ala Asn Tyr Asn Asp Tyr Gln Asn Ala His Leu
                20                  25                  30

Glu Phe Val Glu Asn Met Asn Val Lys Glu Gln Val Thr Gly Asp Ile
            35                  40                  45

Met Tyr Tyr Ile Thr Leu Ala Ala Thr Asp Asp Ala Gly Lys Lys Lys
 50                  55                  60

Ile Tyr Lys Ala Lys Ile Ala Val Val Asp Ser Ala Gly Trp Glu Gly
 65                  70                  75                  80

Val Thr Glu Phe Lys Leu Val
                85

<210> SEQ ID NO 124
<211> LENGTH: 87
<212> TYPE: PRT
<213> ORGANISM: Artificial Sequence
<220> FEATURE:
<223> OTHER INFORMATION: Synthetic

<400> SEQUENCE: 124

Gly Ile Val Asn Val Pro Asn Pro Asn Asn Thr Lys Phe Gln Gln Leu
```

```
                 1               5                  10                 15
Ala Arg Asn Ala Ile Ala Asn Tyr Asn Asp Tyr Gln Asn Ala His Leu
                20                  25                 30
Glu Phe Val Glu Asn Leu Asn Val Lys Glu Gln Val Thr Asp Asp Ile
                35                  40                 45
Met Tyr Tyr Ile Thr Leu Ala Ala Thr Asp Asp Ala Gly Lys Lys Lys
    50                  55                 60
Ile Tyr Lys Ala Lys Ile Ala Val Val Asp Ser Ala Gly Trp Glu Gly
65                  70                  75                    80
Val Thr Glu Phe Lys Leu Val
                85

<210> SEQ ID NO 125
<211> LENGTH: 100
<212> TYPE: PRT
<213> ORGANISM: Artificial Sequence
<220> FEATURE:
<223> OTHER INFORMATION: Synthetic

<400> SEQUENCE: 125

Ala Ser Gly Met Leu Ala Ile Ser Met Asp Thr Asp Lys Ile Ser Asn
1               5                   10                 15
Ser Phe Glu Asp Cys Lys Tyr Phe Gln Leu Tyr Val Leu Ser Ala Gly
                20                  25                 30
Trp Thr Asn Thr Ile Phe Asn Asp Glu Ser Gly Lys Glu Glu Ile Val
                35                  40                 45
Lys Met Ser Val Asp Ala Ile Ile Cys Lys Asn Ile Ser Glu Glu Asn
    50                  55                 60
Tyr Lys Lys Phe Ser Lys Lys Ile Glu Ile Tyr His Ala Glu Gly Asp
65                  70                  75                    80
Asp Val Asp Lys Asn Ile Ser Leu Phe Leu Glu Gly Glu Leu Ser Lys
                85                  90                 95
Ile Ser Asn Pro
            100

<210> SEQ ID NO 126
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 126

Gly Ile Val Asn Val Pro Asn Xaa Asn Thr Thr Lys Tyr Gln Gln Leu
1               5                   10                 15
Ala Arg Arg Ala Ile Ala Ile Tyr Asn His Asn Gln Asn Ala His Leu
                20                  25                 30
Glu Phe Val Glu Asn Leu Asn Xaa Lys Glu Gln Ile Asp Tyr Gly Ser
                35                  40                 45
Met Tyr Tyr Ile Thr Leu Ala Ala Thr Asp Asp Ala Gly Lys Lys Lys
    50                  55                 60
Ile Tyr Lys Ala Lys Val Gly Val Val Glu Ser Ser Gly Trp Thr Gly
```

Val Glu Glu Phe Lys Leu Val
            85

<210> SEQ ID NO 127
<211> LENGTH: 100
<212> TYPE: PRT
<213> ORGANISM: Artificial Sequence
<220> FEATURE:
<223> OTHER INFORMATION: Synthetic

<400> SEQUENCE: 127

Ala Ser Gly Met Leu Ala Ile Ser Met Asp Thr Asp Lys Ile Ser Asn
1               5                   10                  15

Ser Phe Glu Asp Cys Lys Tyr Phe Gln Ile Glu Leu Pro Ser Ala Gly
            20                  25                  30

Trp Thr Asn Thr Ile Phe Asn Asp Glu Ser Gly Lys Glu Glu Ile Val
        35                  40                  45

Lys Met Gly Val Asp Ala Ile Ile Cys Lys Asn Ile Ser Glu Glu Asn
    50                  55                  60

Tyr Lys Lys Phe Ser Lys Lys Ile Glu Ile Tyr His Ala Glu Gly Asp
65                  70                  75                  80

Asp Val Glu Lys Asn Ile Ser Leu Phe Leu Glu Gly Glu Leu Ser Lys
            85                  90                  95

Ile Ser Asn Pro
            100

<210> SEQ ID NO 128
<211> LENGTH: 100
<212> TYPE: PRT
<213> ORGANISM: Artificial Sequence
<220> FEATURE:
<223> OTHER INFORMATION: Synthetic

<400> SEQUENCE: 128

Ala Ser Gly Met Leu Ala Ile Ser Met Asp Thr Asp Lys Ile Ser Asn
1               5                   10                  15

Ser Phe Glu Asp Cys Lys Tyr Phe Gln Leu Val Leu Ala Ser Ala Gly
            20                  25                  30

Trp Thr Asn Thr Ile Phe Asn Asp Glu Ser Gly Lys Glu Glu Ile Val
        35                  40                  45

Lys Met Gly Val Asp Ala Ile Ile Cys Lys Asn Ile Ser Glu Glu Asn
    50                  55                  60

Tyr Lys Lys Phe Ser Lys Lys Ile Glu Ile Tyr His Ala Glu Gly Asp
65                  70                  75                  80

Asp Val Asp Lys Asn Ile Ser Leu Phe Ala Glu Gly Glu Leu Ser Lys
            85                  90                  95

Ile Ser Asn Pro
            100

<210> SEQ ID NO 129
<211> LENGTH: 87
<212> TYPE: PRT
<213> ORGANISM: Artificial Sequence
<220> FEATURE:
<223> OTHER INFORMATION: Synthetic

<400> SEQUENCE: 129

Gly Ile Val Asn Val Pro Asn Pro Asn Asn Thr Lys Phe Gln Glu Leu
1               5                   10                  15

```
Ala Arg Phe Ala Ile Gln Asp Tyr Asn Lys Lys Gln Asn Ala His Leu
            20                  25                  30

Glu Phe Val Glu Asn Leu Asn Val Lys Glu Gln Val Val Ala Gly Ile
        35                  40                  45

Met Tyr Tyr Ile Thr Leu Ala Ala Thr Asp Asp Ala Gly Lys Lys Lys
 50                  55                  60

Ile Tyr Lys Ala Lys Ile Trp Val Lys Glu Trp Glu Asp Phe Lys Lys
 65                  70                  75                  80

Val Val Glu Phe Lys Leu Val
                85

<210> SEQ ID NO 130
<211> LENGTH: 104
<212> TYPE: PRT
<213> ORGANISM: Artificial Sequence
<220> FEATURE:
<223> OTHER INFORMATION: Synthetic

<400> SEQUENCE: 130

Met Ile Asn Met Lys Val Ala Ile Ser Met Asp Val Asp Lys Ile Ser
 1               5                  10                  15

Asn Ser Phe Glu Asp Cys Lys Tyr Phe Leu Ile Val Arg Ile Asp Asp
            20                  25                  30

Asn Glu Val Lys Ser Thr Lys Val Ile Phe Asn Asp Glu Ser Gly Lys
        35                  40                  45

Lys Ser Ile Val Lys Glu Asn Val Asn Ala Ile Ile Cys Lys Asn Ile
 50                  55                  60

Ser Glu Glu Asn Tyr Lys Lys Phe Ser Lys Lys Ile Glu Ile Tyr His
 65                  70                  75                  80

Ala Glu Gly Asp Asp Val Asp Lys Asn Ile Ser Leu Phe Ile Glu Gly
            85                  90                  95

Glu Leu Ser Lys Ile Ser Asn Pro
            100

<210> SEQ ID NO 131
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa P or C
<220> FEATURE:
<221> NAME/KEY: MISC_FEATURE
<222> LOCATION: (40)..(40)
<223> OTHER INFORMATION: Xaa V or C

<400> SEQUENCE: 131

Gly Ile Val Asn Val Pro Asn Xaa Asn Thr Lys Phe Gln Gln Leu
 1               5                  10                  15

Ala Arg Ser Ala Ile Ala Asn Tyr Asn Asp Tyr Gln Asn Ala His Leu
            20                  25                  30

Glu Phe Val Glu Asn Leu Asn Xaa Lys Glu Gln Val Thr Gly Asp Ile
        35                  40                  45

Met Tyr Tyr Ile Thr Leu Ala Ala Thr Asp Asp Ala Gly Lys Lys Lys
 50                  55                  60

Ile Tyr Lys Ala Lys Ile Ala Val Val Asp Ser Ala Gly Trp Glu Gly
 65                  70                  75                  80
```

```
<210> SEQ ID NO 132
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 132

Gly Ile Val Asn Val Pro Asn Xaa Asn Asn Thr Lys Phe Gln Gln Leu
1               5                   10                  15

Ala Arg Tyr Ala Ile Ala Asn Tyr Asn Asp Tyr Gln Asn Ala His Leu
            20                  25                  30

Glu Phe Val Glu Asn Leu Asn Xaa Lys Glu Gln Val Thr Gly Asp Ile
        35                  40                  45

Met Tyr Tyr Ile Thr Leu Ala Ala Thr Asp Asp Ala Gly Lys Lys Lys
    50                  55                  60

Ile Tyr Lys Ala Lys Ile Ala Val Val Asp Ser Ala Gly Trp Glu Gly
65                  70                  75                  80

Val Thr Glu Phe Lys Leu Val
                85

<210> SEQ ID NO 133
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 133

Gly Ile Val Asn Val Pro Asn Xaa Asn Asn Thr Lys Phe Gln Gln Leu
1               5                   10                  15

Ala Arg Asn Ala Ile Ala Asn Tyr Asn Asp Tyr Gln Asn Ala His Leu
            20                  25                  30

Glu Phe Val Glu Asn Met Asn Xaa Lys Glu Gln Val Thr Gly Asp Ile
        35                  40                  45

Met Tyr Tyr Ile Thr Leu Ala Ala Thr Asp Asp Ala Gly Lys Lys Lys
    50                  55                  60

Ile Tyr Lys Ala Lys Ile Ala Val Val Asp Ser Ala Gly Trp Glu Gly
65                  70                  75                  80

Val Thr Glu Phe Lys Leu Val
                85

<210> SEQ ID NO 134
<211> LENGTH: 87
```

-continued

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is P or C
<220> FEATURE:
<221> NAME/KEY: MISC_FEATURE
<222> LOCATION: (40)..(40)
<223> OTHER INFORMATION: Xaa is V or C

<400> SEQUENCE: 134

Gly Ile Val Asn Val Pro Asn Xaa Asn Asn Thr Lys Phe Gln Gln Leu
1               5                   10                  15

Ala Arg Asn Ala Ile Ala Asn Tyr Asn Asp Tyr Gln Asn Ala His Leu
            20                  25                  30

Glu Phe Val Glu Asn Leu Asn Xaa Lys Glu Gln Val Thr Asp Asp Ile
        35                  40                  45

Met Tyr Tyr Ile Thr Leu Ala Ala Thr Asp Asp Ala Gly Lys Lys Lys
    50                  55                  60

Ile Tyr Lys Ala Lys Ile Ala Val Val Asp Ser Ala Gly Trp Glu Gly
65                  70                  75                  80

Val Thr Glu Phe Lys Leu Val
                85
```

We claim:

1. An isolated polypeptide comprising a polypeptide at least 90% identical over the full length of the amino acid sequence of SEQ ID NO:1 wherein the polypeptide does not comprise the amino acid sequence of SEQ ID NO: 129, and wherein amino acid sequence variability compared to SEQ ID NO:1 is limited to amino acid residues 1-17, 28-43, 49-69, and 83-87.

2. The isolated polypeptide of claim 1, comprising a polypeptide at least 90% identical over the full length of the amino acid sequence of SEQ ID NO:2.

3. The isolated polypeptide of claim 1, comprising a polypeptide at least 90% identical over the full length of the amino acid sequence of SEQ ID NO:3.

4. The isolated polypeptide of claim 1, wherein the polypeptide comprises the amino acid sequence selected from the group consisting of SEQ ID NOs:11-39, 95-97, 126, and 131-134.

5. The isolated polypeptide of claim 1, further comprising a tag.

6. The isolated polypeptide of claim 5, wherein the tag is selected from the group consisting of a detectable moiety and a therapeutic agent.

7. The isolated polypeptide of claim 1, wherein the polypeptide is attached to a solid support.

8. The isolated polypeptide of claim 1, comprising a polypeptide at least 95% identical over the full length of the amino acid sequence of SEQ ID NO:1.

9. The isolated polypeptide of claim 2, comprising a polypeptide at least 95% identical over the full length of the amino acid sequence of SEQ ID NO:2.

10. The isolated polypeptide of claim 3, comprising a polypeptide at least 95% identical over the full length of the amino acid sequence of SEQ ID NO:3.

11. The isolated polypeptide of claim 1, comprising the amino acid sequence of SEQ ID NO:1.

12. The isolated polypeptide of claim 2, comprising the amino acid sequence of SEQ ID NO:2.

13. The isolated polypeptide of claim 3, comprising the amino acid sequence of SEQ ID NO:3.

14. The isolated polypeptide of claim 2, further comprising a tag selected from the group consisting of a detectable moiety and a therapeutic agent.

15. The isolated polypeptide of claim 3, further comprising a tag selected from the group consisting of a detectable moiety and a therapeutic agent.

16. The isolated polypeptide of claim 4, further comprising a tag selected from the group consisting of a detectable moiety and a therapeutic agent.

17. A pharmaceutical composition comprising:
  (a) the polypeptide of claim 1; and
  (b) a pharmaceutically acceptable carrier.

18. An isolated polypeptide, wherein the polypeptide comprises a polypeptide at least 85% identical over the full length of the amino acid sequence selected from the group consisting of SEQ ID NOs:11-39, 95-97, 126, and 131-134.

19. The isolated polypeptide of claim 18, wherein the polypeptide comprises a polypeptide at least 90% identical over the full length of the amino acid sequence selected from the group consisting of SEQ ID NOs:11-39, 95-97, 126, and 131-134.

20. The isolated polypeptide of claim 18, wherein the polypeptide comprises a polypeptide at least 95% identical over the full length of the amino acid sequence selected from the group consisting of SEQ ID NOs:11-39, 95-97, 126, and 131-134.

* * * * *